(12) United States Patent
Baltzer et al.

(10) Patent No.: US 9,377,466 B2
(45) Date of Patent: Jun. 28, 2016

(54) COMPOUNDS AND METHODS

(75) Inventors: Lars Baltzer, Uppsala (SE); Adam Slosarczyk, Upssala (SE); Jonas Bergquist, Uppsala (SE); Anders Virtanen, Uppsala (SE)

(73) Assignee: Modpro AB, Uppsala (SE)

( * ) Notice: Subject to any disclaimer, the term of this patent is extended or adjusted under 35 U.S.C. 154(b) by 388 days.

(21) Appl. No.: 13/820,645

(22) PCT Filed: Sep. 6, 2011

(86) PCT No.: PCT/EP2011/065421
§ 371 (c)(1),
(2), (4) Date: Mar. 4, 2013

(87) PCT Pub. No.: WO2012/032068
PCT Pub. Date: Mar. 15, 2012

(65) Prior Publication Data
US 2013/0261013 A1    Oct. 3, 2013

Related U.S. Application Data

(60) Provisional application No. 61/382,171, filed on Sep. 13, 2010.

(30) Foreign Application Priority Data

Sep. 6, 2010  (SE) ........................................ 1000906
Sep. 13, 2010  (EP) ...................................... 10176360

(51) Int. Cl.
C40B 40/10    (2006.01)
G01N 33/68    (2006.01)
C12N 9/12    (2006.01)
C12N 9/18    (2006.01)
C12N 9/88    (2006.01)
C07K 14/00    (2006.01)
G01N 33/573    (2006.01)
A61K 38/00    (2006.01)

(52) U.S. Cl.
CPC .............. *G01N 33/68* (2013.01); *C07K 14/001* (2013.01); *C12N 9/1211* (2013.01); *C12N 9/18* (2013.01); *C12N 9/88* (2013.01); *G01N 33/573* (2013.01); *A61K 38/00* (2013.01); *C07K 2319/01* (2013.01); *C40B 40/10* (2013.01)

(58) Field of Classification Search
None
See application file for complete search history.

(56) References Cited

U.S. PATENT DOCUMENTS

2012/0202218 A1 *   8/2012   Liedberg et al. ............... 435/7.4

* cited by examiner

*Primary Examiner* — Christian Boesen
(74) *Attorney, Agent, or Firm* — Buchanan Ingersoll & Rooney PC

(57) ABSTRACT

A molecular tool for use in a method of providing a molecule that is capable of binding a target molecule based on a set of polypeptides. A polypeptide having a sequence selected from SEQ ID NOs 1-32. The polypeptide may be used in a method of screening for a ligand-polypeptide conjugate capable of binding a target molecule for the ligand. A ligand-polypeptide conjugate, useful e.g. in therapy.

13 Claims, 39 Drawing Sheets

| | | | |
|---|---|---|---|
| SEQ ID NO: 1 | 1-C15L8 | Ac-NEADLEAXIRHLAEXLEARGPEDAEQLAEQLARAFEAFARAG-COOH | -7 |
| SEQ ID NO: 2 | 2-C15L8 | Ac-NEADLEAXIRHLAEXLAARGPVDAAQLAEQLARAFEAFARAG-COOH | -4 |
| SEQ ID NO: 3 | 3-C15L8 | Ac-NAADLEAXIRHLAEXLAARGPVDAAQLAEQLARRFEAFARAG-CONH$_2$ | -1 |
| SEQ ID NO: 4 | 4-C15L8 | Ac-NAADLEAXIRHLREXLAARGPRDAAQLAEQLARRFERFARAG-CONH$_2$ | +2 |
| SEQ ID NO: 5 | 1-C10L17 | Ac-NAADLEAAIXHLAEALXERGPEDCEQLAEQLARAFEAFARAG-COOH | -7 |
| SEQ ID NO: 6 | 2-C10L17 | Ac-NAADLEAAIXHLAEALXARGPVDAAQLAEQLARAFEAFARAG-COOH | -4 |
| SEQ ID NO: 7 | 3-C10L17 | Ac-NAADLEARIXHLAERLXARGPVDAAQLAEQLARAFEAFARAG-CONH$_2$ | -1 |
| SEQ ID NO: 8 | 4-C10L17 | Ac-NAADLEARIXHLRERLXARGPRDAAQLAEQLARAFERFARAG-CONH$_2$ | +2 |
| SEQ ID NO: 9 | 1-C25L22 | Ac-NEADLEAAIRHLAEALEARGPXDAXQLAEQLARAFEAFERAG-COOH | -6 |
| SEQ ID NO: 10 | 2-C25L22 | Ac-NEADLEAAIRHLAEALAARGPXDAXQLAEQLARAFEAFARAG-COOH | -4 |
| SEQ ID NO: 11 | 3-C25L22 | Ac-NAADLEAAIRHLAERLAARGPXDAXQLAEQLARAFEAFARAG-CONH$_2$ | -1 |
| SEQ ID NO: 12 | 4-C25L22 | Ac-NAADLEARIRHLRERLAARGPKDAXQLAEQLARAFERFARAG-CONH$_2$ | +2 |
| SEQ ID NO: 13 | 1-C37L34 | Ac-NEADLEAAIRHLAERLEARGPADAAQLAEQLAAXFEXFARAG-COOH | -5 |
| SEQ ID NO: 14 | 2-C37L34 | Ac-NAADLEAAIRHLAERLAARGPVDAAQLAEQLAAXFEXFARAG-COOH | -3 |
| SEQ ID NO: 15 | 3-C37L34 | Ac-NAADLEAAIRHLAERLAARGPVDAAQLAEQLARXFEXFARAG-CONH$_2$ | -1 |
| SEQ ID NO: 16 | 4-C37L34 | Ac-NAADLEARIRHLRERLAARGPRDAAQLAEQLARXFEXFARAG-CONH$_2$ | +2 |

| SEQ ID NO | Name | Sequence | Charge |
|---|---|---|---|
| SEQ ID NO: 1 | 1-C15L8 | Ac-NEADLEAXIRHLAEXLEARGPEDAEQLAEQLARAFEAFARAG-COOH | -7 |
| SEQ ID NO: 2 | 2-C15L8 | Ac-NEADLEAXIRHLAEXLAARGPVDAAQLAEQLARAFEAFARAG-COOH | -4 |
| SEQ ID NO: 3 | 3-C15L8 | Ac-NAADLEAXIRHLAEXLAARGPVDAAQLAEQLARRFEAFARAG-CONH$_2$ | -1 |
| SEQ ID NO: 4 | 4-C15L8 | Ac-NAADLEAXIRHLREXLAARGPRDAAQLAEQLARRFERFARAG-CONH$_2$ | +2 |
| SEQ ID NO: 5 | 1-C10L17 | Ac-NEADLEAIXHLAEALXERGPEDCEQLAEQLARAFEAFARAG-COOH | -7 |
| SEQ ID NO: 6 | 2-C10L17 | Ac-NAADLEAIXHLAEALXARGPVDAAQLAEQLARAFEAFARAG-COOH | -4 |
| SEQ ID NO: 7 | 3-C10L17 | Ac-NAADLEARIXHLAERLXARGPVDAAQLAEQLARAFEAFARAG-CONH$_2$ | -1 |
| SEQ ID NO: 8 | 4-C10L17 | Ac-NAADLEARIXHLRERLXARGPRDAAQLAEQLARAFERFARAG-CONH$_2$ | +2 |
| SEQ ID NO: 9 | 1-C25L22 | Ac-NEADLEAAIRHLAEALEARGPXDAXQLAEQLARAFEAFERAG-COOH | -6 |
| SEQ ID NO: 10 | 2-C25L22 | Ac-NEADLEAAIRHLAEALAARGPXDAXQLAEQLARAFEAFARAG-COOH | -4 |
| SEQ ID NO: 11 | 3-C25L22 | Ac-NAADLEAAIRHLAERLAARGPXDAXQLARAFEAFARAG-CONH$_2$ | -1 |
| SEQ ID NO: 12 | 4-C25L22 | Ac-NAADLEARIRHLRERLAARGPKDAXQLAEQLARAFERFARAG-CONH$_2$ | +2 |
| SEQ ID NO: 13 | 1-C37L34 | Ac-NEADLEAAIRHLAERLEARGPADAAQLAEQLAAXFEXFARAG-COOH | -5 |
| SEQ ID NO: 14 | 2-C37L34 | Ac-NAADLEAAIRHLAERLAARGPVDAAQLAEQLAAXFEXFARAG-COOH | -3 |
| SEQ ID NO: 15 | 3-C37L34 | Ac-NAADLEAAIRHLAERLAARGPVDAAQLAEQLARXFEXFARAG-CONH$_2$ | -1 |
| SEQ ID NO: 16 | 4-C37L34 | Ac-NAADLEARIRHLRERLAARGPRDAAQLAEQLARXFEXFARAG-CONH$_2$ | +2 |

Fig. 1

FIG. 10
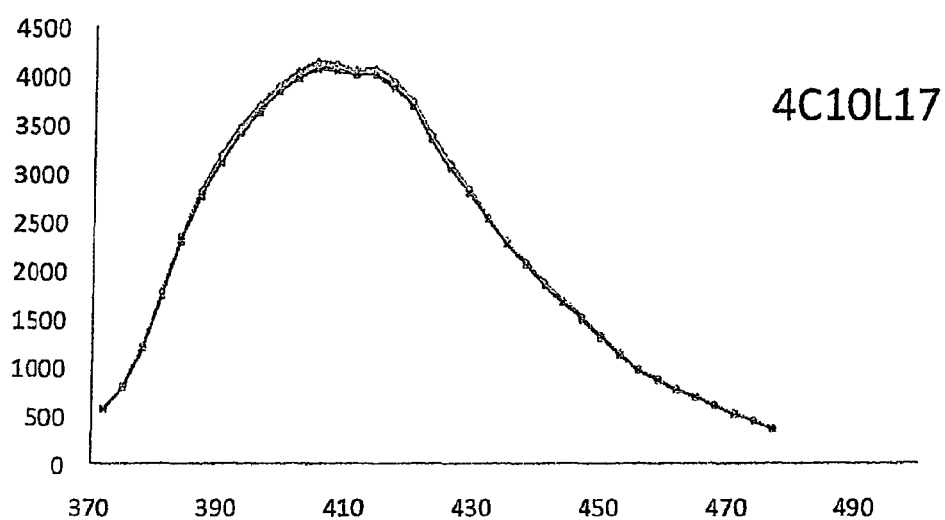
4C10L17
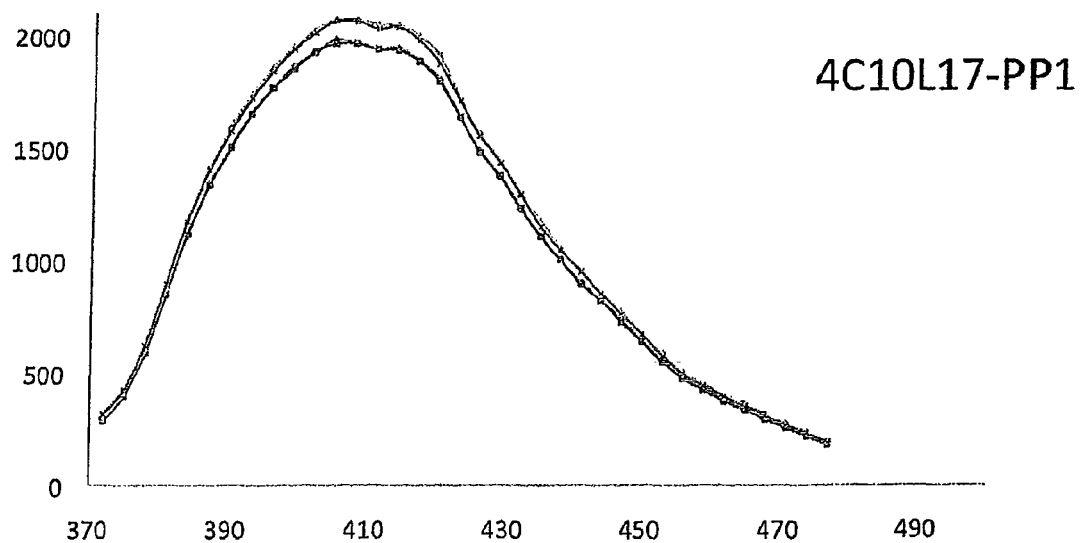
4C10L17-PP1

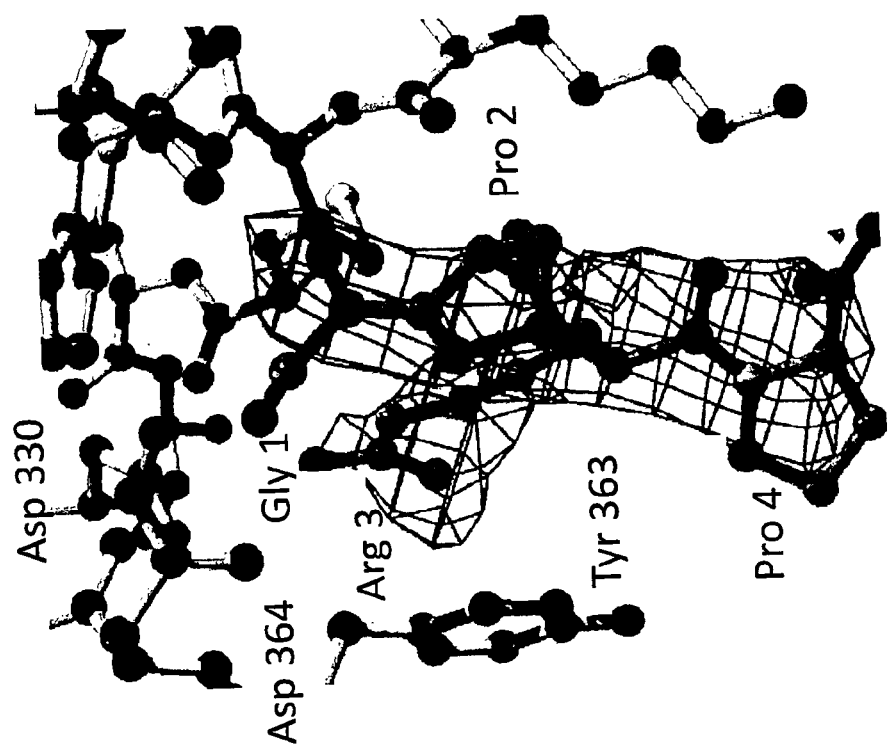
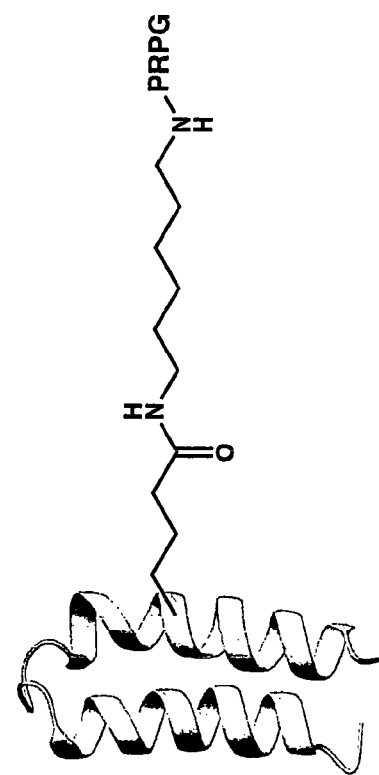
FIG. 31

1D15L8_GPRP
1D10L17_GPRP
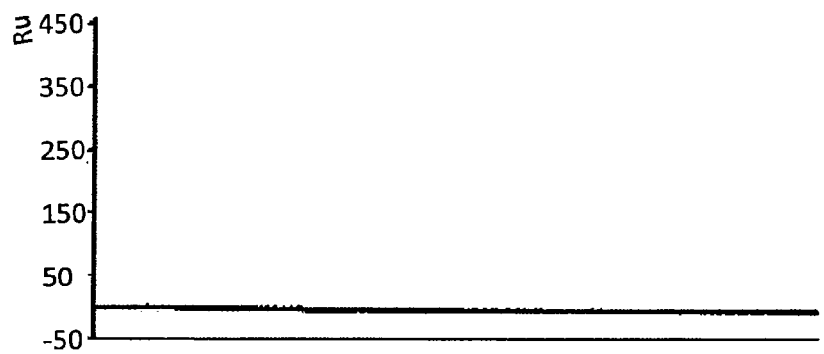
1D25L22_GPRP
1D37L34_GPRP
FIG. 32

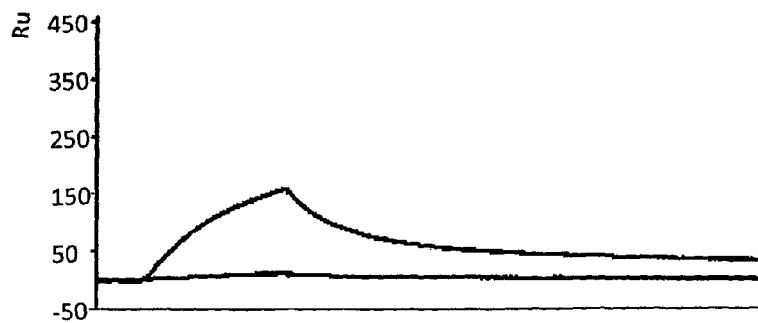
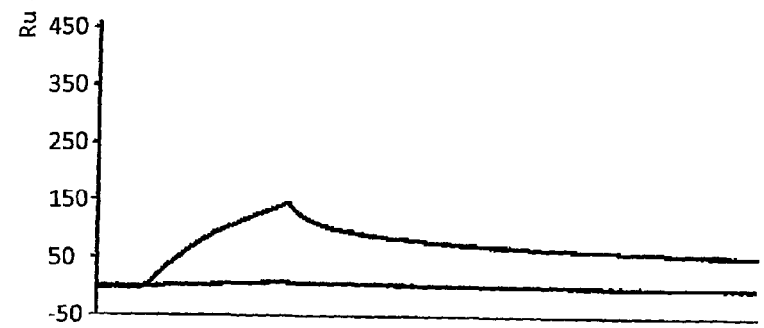
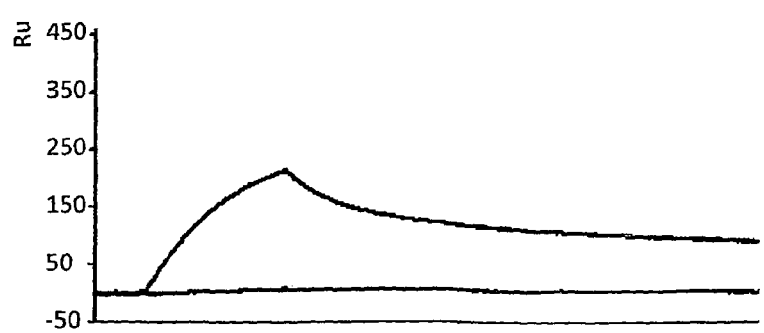
FIG. 32 cont.

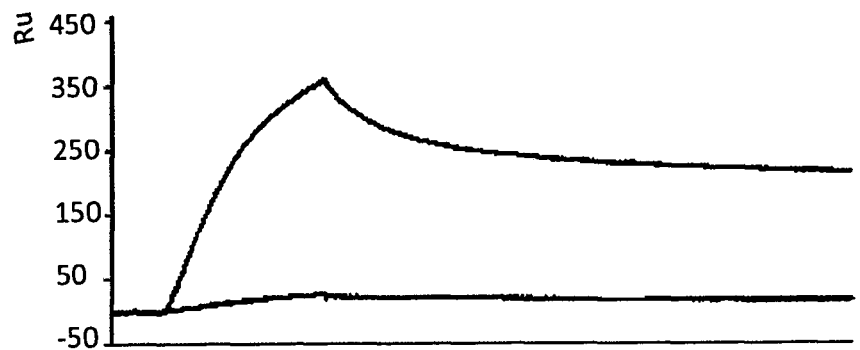
FIG. 32 cont.

SEQUENCE LISTING

```
<160> NUMBER OF SEQ ID NOS: 32

<210> SEQ ID NO 1
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylation
<220> FEATURE:
<221> NAME/KEY: MISC_FEATURE
<222> LOCATION: (8)..(8)
<223> OTHER INFORMATION: Ligand attachment site
<220> FEATURE:
<221> NAME/KEY: MISC_FEATURE
<222> LOCATION: (15)..(15)
<223> OTHER INFORMATION: Reporter attachment site

<400> SEQUENCE: 1

Asn Glu Ala Asp Leu Glu Ala Lys Ile Arg His Leu Ala Glu Lys Leu
1               5                   10                  15

Glu Ala Arg Gly Pro Glu Asp Ala Glu Gln Leu Ala Glu Gln Leu Ala
            20                  25                  30

Arg Ala Phe Glu Ala Phe Ala Arg Ala Gly
        35                  40

<210> SEQ ID NO 2
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylation
<220> FEATURE:
<221> NAME/KEY: MISC_FEATURE
<222> LOCATION: (8)..(8)
```

```
<223> OTHER INFORMATION: Ligand attachment site
<220> FEATURE:
<221> NAME/KEY: MISC_FEATURE
<222> LOCATION: (15)..(15)
<223> OTHER INFORMATION: Reporter attachment site

<400> SEQUENCE: 2

Asn Glu Ala Asp Leu Glu Ala Lys Ile Arg His Leu Ala Glu Lys Leu
1               5                   10                  15

Ala Ala Arg Gly Pro Val Asp Ala Ala Gln Leu Ala Glu Gln Leu Ala
            20                  25                  30

Arg Ala Phe Glu Ala Phe Ala Arg Ala Gly
        35                  40

<210> SEQ ID NO 3
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylation
<220> FEATURE:
<221> NAME/KEY: MISC_FEATURE
<222> LOCATION: (8)..(8)
<223> OTHER INFORMATION: Ligand attachment site
<220> FEATURE:
<221> NAME/KEY: MISC_FEATURE
<222> LOCATION: (15)..(15)
<223> OTHER INFORMATION: Reporter attachment site
<220> FEATURE:
<221> NAME/KEY: MOD_RES
<222> LOCATION: (42)..(42)
<223> OTHER INFORMATION: Amidation

<400> SEQUENCE: 3

Asn Ala Ala Asp Leu Glu Ala Lys Ile Arg His Leu Ala Glu Lys Leu
1               5                   10                  15

Ala Ala Arg Gly Pro Val Asp Ala Ala Gln Leu Ala Glu Gln Leu Ala
            20                  25                  30

Arg Arg Phe Glu Ala Phe Ala Arg Ala Gly
        35                  40

<210> SEQ ID NO 4
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylation
<220> FEATURE:
<221> NAME/KEY: MISC_FEATURE
<222> LOCATION: (8)..(8)
<223> OTHER INFORMATION: Ligand attachment site
<220> FEATURE:
<221> NAME/KEY: MISC_FEATURE
<222> LOCATION: (15)..(15)
<223> OTHER INFORMATION: Reporter attachment site
<220> FEATURE:
<221> NAME/KEY: MOD_RES
<222> LOCATION: (42)..(42)
<223> OTHER INFORMATION: Amidation

<400> SEQUENCE: 4

Asn Ala Ala Asp Leu Glu Ala Lys Ile Arg His Leu Arg Glu Lys Leu
```

```
                1               5                  10                 15
Ala Ala Arg Gly Pro Arg Asp Ala Ala Gln Leu Ala Glu Gln Leu Ala
                20                 25                 30
Arg Arg Phe Glu Arg Phe Ala Arg Ala Gly
            35                  40

<210> SEQ ID NO 5
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylation
<220> FEATURE:
<221> NAME/KEY: MISC_FEATURE
<222> LOCATION: (10)..(10)
<223> OTHER INFORMATION: Reporter attachment site
<220> FEATURE:
<221> NAME/KEY: MISC_FEATURE
<222> LOCATION: (17)..(17)
<223> OTHER INFORMATION: Ligand attachment site

<400> SEQUENCE: 5

Asn Ala Ala Asp Leu Glu Ala Ala Ile Lys His Leu Ala Glu Ala Leu
1               5                  10                 15
Lys Glu Arg Gly Pro Glu Asp Ala Glu Gln Leu Ala Glu Gln Leu Ala
                20                 25                 30
Arg Ala Phe Glu Ala Phe Ala Arg Ala Gly
            35                  40

<210> SEQ ID NO 6
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylation
<220> FEATURE:
<221> NAME/KEY: MISC_FEATURE
<222> LOCATION: (10)..(10)
<223> OTHER INFORMATION: Reporter attachment site
<220> FEATURE:
<221> NAME/KEY: MISC_FEATURE
<222> LOCATION: (17)..(17)
<223> OTHER INFORMATION: Ligand attachment site

<400> SEQUENCE: 6

Asn Ala Ala Asp Leu Glu Ala Ala Ile Lys His Leu Ala Glu Ala Leu
1               5                  10                 15
Lys Ala Arg Gly Pro Val Asp Ala Ala Gln Leu Ala Glu Gln Leu Ala
                20                 25                 30
Arg Ala Phe Glu Ala Phe Ala Arg Ala Gly
            35                  40

<210> SEQ ID NO 7
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
```

<222> LOCATION: (1)..(1)
<223> OTHER INFORMATION: Acylation
<220> FEATURE:
<221> NAME/KEY: MISC_FEATURE
<222> LOCATION: (10)..(10)
<223> OTHER INFORMATION: Reporter attachment site
<220> FEATURE:
<221> NAME/KEY: MISC_FEATURE
<222> LOCATION: (17)..(17)
<223> OTHER INFORMATION: Ligand attachment site
<220> FEATURE:
<221> NAME/KEY: MOD_RES
<222> LOCATION: (42)..(42)
<223> OTHER INFORMATION: Amidation

<400> SEQUENCE: 7

Asn Ala Ala Asp Leu Glu Ala Arg Ile Lys His Leu Ala Glu Arg Leu
1               5                   10                  15

Lys Ala Arg Gly Pro Val Asp Ala Ala Gln Leu Ala Glu Gln Leu Ala
            20                  25                  30

Arg Ala Phe Glu Ala Phe Ala Arg Ala Gly
        35                  40

<210> SEQ ID NO 8
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylation
<220> FEATURE:
<221> NAME/KEY: MISC_FEATURE
<222> LOCATION: (10)..(10)
<223> OTHER INFORMATION: Reporter attachment site
<220> FEATURE:
<221> NAME/KEY: MISC_FEATURE
<222> LOCATION: (17)..(17)
<223> OTHER INFORMATION: Ligand attachment site
<220> FEATURE:
<221> NAME/KEY: MOD_RES
<222> LOCATION: (42)..(42)
<223> OTHER INFORMATION: Amidation

<400> SEQUENCE: 8

Asn Ala Ala Asp Leu Glu Ala Arg Ile Lys His Leu Arg Glu Arg Leu
1               5                   10                  15

Lys Ala Arg Gly Pro Arg Asp Ala Ala Gln Leu Ala Glu Gln Leu Ala
            20                  25                  30

Arg Ala Phe Glu Arg Phe Ala Arg Ala Gly
        35                  40

<210> SEQ ID NO 9
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylation
<220> FEATURE:
<221> NAME/KEY: MISC_FEATURE
<222> LOCATION: (22)..(22)
<223> OTHER INFORMATION: Ligand attachment site
<220> FEATURE:
<221> NAME/KEY: MISC_FEATURE
<222> LOCATION: (25)..(25)

<223> OTHER INFORMATION: Reporter attachment site

<400> SEQUENCE: 9

Asn Glu Ala Asp Leu Glu Ala Ala Ile Arg His Leu Ala Glu Ala Leu
1               5                   10                  15

Glu Ala Arg Gly Pro Lys Asp Ala Lys Gln Leu Ala Glu Gln Leu Ala
            20                  25                  30

Arg Ala Phe Glu Ala Phe Glu Arg Ala Gly
        35                  40

<210> SEQ ID NO 10
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylation
<220> FEATURE:
<221> NAME/KEY: MISC_FEATURE
<222> LOCATION: (22)..(22)
<223> OTHER INFORMATION: Ligand attachment site
<220> FEATURE:
<221> NAME/KEY: MISC_FEATURE
<222> LOCATION: (25)..(25)
<223> OTHER INFORMATION: Reporter attachment site

<400> SEQUENCE: 10

Asn Glu Ala Asp Leu Glu Ala Ala Ile Arg His Leu Ala Glu Ala Leu
1               5                   10                  15

Ala Ala Arg Gly Pro Lys Asp Ala Lys Gln Leu Ala Glu Gln Leu Ala
            20                  25                  30

Arg Ala Phe Glu Ala Phe Ala Arg Ala Gly
        35                  40

<210> SEQ ID NO 11
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylation
<220> FEATURE:
<221> NAME/KEY: MISC_FEATURE
<222> LOCATION: (22)..(22)
<223> OTHER INFORMATION: Ligand attachment site
<220> FEATURE:
<221> NAME/KEY: MISC_FEATURE
<222> LOCATION: (25)..(25)
<223> OTHER INFORMATION: Reporter attachment site
<220> FEATURE:
<221> NAME/KEY: MOD_RES
<222> LOCATION: (42)..(42)
<223> OTHER INFORMATION: Amidation

<400> SEQUENCE: 11

Asn Ala Ala Asp Leu Glu Ala Ala Ile Arg His Leu Ala Glu Arg Leu
1               5                   10                  15

Ala Ala Arg Gly Pro Lys Asp Ala Lys Gln Leu Ala Glu Gln Leu Ala
            20                  25                  30

Arg Ala Phe Glu Ala Phe Ala Arg Ala Gly
        35                  40

```
<210> SEQ ID NO 12
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylation
<220> FEATURE:
<221> NAME/KEY: MISC_FEATURE
<222> LOCATION: (22)..(22)
<223> OTHER INFORMATION: Ligand attachment site
<220> FEATURE:
<221> NAME/KEY: MISC_FEATURE
<222> LOCATION: (25)..(25)
<223> OTHER INFORMATION: Reporter attachment site
<220> FEATURE:
<221> NAME/KEY: MOD_RES
<222> LOCATION: (42)..(42)
<223> OTHER INFORMATION: Amidation

<400> SEQUENCE: 12

Asn Ala Ala Asp Leu Glu Ala Arg Ile Arg His Leu Arg Glu Arg Leu
1               5                   10                  15

Ala Ala Arg Gly Pro Lys Asp Ala Lys Gln Leu Ala Glu Gln Leu Ala
            20                  25                  30

Arg Ala Phe Glu Arg Phe Ala Arg Ala Gly
        35                  40

<210> SEQ ID NO 13
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylation
<220> FEATURE:
<221> NAME/KEY: MISC_FEATURE
<222> LOCATION: (34)..(34)
<223> OTHER INFORMATION: Ligand attachment site
<220> FEATURE:
<221> NAME/KEY: MISC_FEATURE
<222> LOCATION: (37)..(37)
<223> OTHER INFORMATION: Reporter attachment site

<400> SEQUENCE: 13

Asn Glu Ala Asp Leu Glu Ala Ala Ile Arg His Leu Ala Glu Arg Leu
1               5                   10                  15

Glu Ala Arg Gly Pro Ala Asp Ala Ala Gln Leu Ala Glu Gln Leu Ala
            20                  25                  30

Ala Lys Phe Glu Lys Phe Ala Arg Ala Gly
        35                  40

<210> SEQ ID NO 14
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylation
<220> FEATURE:
<221> NAME/KEY: MISC_FEATURE
```

```
<222> LOCATION: (34)..(34)
<223> OTHER INFORMATION: Ligand attachment site
<220> FEATURE:
<221> NAME/KEY: MISC_FEATURE
<222> LOCATION: (37)..(37)
<223> OTHER INFORMATION: Reporter attachment site

<400> SEQUENCE: 14

Asn Ala Ala Asp Leu Glu Ala Ala Ile Arg His Leu Ala Glu Arg Leu
 1               5                  10                  15
Ala Ala Arg Gly Pro Val Asp Ala Ala Gln Leu Ala Glu Gln Leu Ala
            20                  25                  30
Ala Lys Phe Glu Lys Phe Ala Arg Ala Gly
        35                  40

<210> SEQ ID NO 15
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylation
<220> FEATURE:
<221> NAME/KEY: MISC_FEATURE
<222> LOCATION: (34)..(34)
<223> OTHER INFORMATION: Ligand attachment site
<220> FEATURE:
<221> NAME/KEY: MISC_FEATURE
<222> LOCATION: (37)..(37)
<223> OTHER INFORMATION: Reporter attachment site
<220> FEATURE:
<221> NAME/KEY: MOD_RES
<222> LOCATION: (42)..(42)
<223> OTHER INFORMATION: Amidation

<400> SEQUENCE: 15

Asn Ala Ala Asp Leu Glu Ala Ala Ile Arg His Leu Ala Glu Arg Leu
 1               5                  10                  15
Ala Ala Arg Gly Pro Val Asp Ala Ala Gln Leu Ala Glu Gln Leu Ala
            20                  25                  30
Arg Lys Phe Glu Lys Phe Ala Arg Ala Gly
        35                  40

<210> SEQ ID NO 16
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylation
<220> FEATURE:
<221> NAME/KEY: MISC_FEATURE
<222> LOCATION: (34)..(34)
<223> OTHER INFORMATION: Ligand attachment site
<220> FEATURE:
<221> NAME/KEY: MISC_FEATURE
<222> LOCATION: (37)..(37)
<223> OTHER INFORMATION: Reporter attachment site
<220> FEATURE:
<221> NAME/KEY: MOD_RES
<222> LOCATION: (42)..(42)
<223> OTHER INFORMATION: Amidation

<400> SEQUENCE: 16
```

-continued

Asn Ala Ala Asp Leu Glu Ala Arg Ile Arg His Leu Arg Glu Arg Leu
1               5                   10                  15

Ala Ala Arg Gly Pro Arg Asp Ala Gln Leu Ala Glu Gln Leu Ala
            20                  25                  30

Arg Lys Phe Glu Lys Phe Ala Arg Ala Gly
        35                  40

<210> SEQ ID NO 17
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (8)..(8)
<223> OTHER INFORMATION: Amino acid capable of forming amide bond with
      ligand
<220> FEATURE:
<221> NAME/KEY: VARIANT
<222> LOCATION: (15)..(15)
<223> OTHER INFORMATION: Amino acid capable of forming amide bond with
      reporter group

<400> SEQUENCE: 17

Asn Glu Ala Asp Leu Glu Ala Xaa Ile Arg His Leu Ala Glu Xaa Leu
1               5                   10                  15

Glu Ala Arg Gly Pro Glu Asp Ala Glu Gln Leu Ala Glu Gln Leu Ala
            20                  25                  30

Arg Ala Phe Glu Ala Phe Ala Arg Ala Gly
        35                  40

<210> SEQ ID NO 18
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (8)..(8)
<223> OTHER INFORMATION: Amino acid capable of forming amide bond with
      ligand
<220> FEATURE:
<221> NAME/KEY: VARIANT
<222> LOCATION: (15)..(15)
<223> OTHER INFORMATION: Amino acid capable of forming amide bond with
      reporter group

<400> SEQUENCE: 18

Asn Glu Ala Asp Leu Glu Ala Xaa Ile Arg His Leu Ala Glu Xaa Leu
1               5                   10                  15

Ala Ala Arg Gly Pro Val Asp Ala Gln Leu Ala Glu Gln Leu Ala
            20                  25                  30

Arg Ala Phe Glu Ala Phe Ala Arg Ala Gly
        35                  40

<210> SEQ ID NO 19
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (8)..(8)
<223> OTHER INFORMATION: Amino acid capable of forming amide bond with
      ligand -continued

```
<220> FEATURE:
<221> NAME/KEY: VARIANT
<222> LOCATION: (15)..(15)
<223> OTHER INFORMATION: Amino acid capable of forming amide bond with
      reporter group

<400> SEQUENCE: 19

Asn Ala Ala Asp Leu Glu Ala Xaa Ile Arg His Leu Ala Glu Xaa Leu
1               5                   10                  15

Ala Ala Arg Gly Pro Val Asp Ala Ala Gln Leu Ala Glu Gln Leu Ala
            20                  25                  30

Arg Arg Phe Glu Ala Phe Ala Arg Ala Gly
        35                  40

<210> SEQ ID NO 20
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (8)..(8)
<223> OTHER INFORMATION: Amino acid capable of forming amide bond with
      ligand
<220> FEATURE:
<221> NAME/KEY: VARIANT
<222> LOCATION: (15)..(15)
<223> OTHER INFORMATION: Amino acid capable of forming amide bond with
      reporter group

<400> SEQUENCE: 20

Asn Ala Ala Asp Leu Glu Ala Xaa Ile Arg His Leu Arg Glu Xaa Leu
1               5                   10                  15

Ala Ala Arg Gly Pro Arg Asp Ala Ala Gln Leu Ala Glu Gln Leu Ala
            20                  25                  30

Arg Arg Phe Glu Arg Phe Ala Arg Ala Gly
        35                  40

<210> SEQ ID NO 21
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (10)..(10)
<223> OTHER INFORMATION: Amino acid capable of forming amide bond with
      reporter group
<220> FEATURE:
<221> NAME/KEY: VARIANT
<222> LOCATION: (17)..(17)
<223> OTHER INFORMATION: Amino acid capable of forming amide bond with
      ligand

<400> SEQUENCE: 21

Asn Ala Ala Asp Leu Glu Ala Ala Ile Xaa His Leu Ala Glu Ala Leu
1               5                   10                  15

Xaa Glu Arg Gly Pro Glu Asp Cys Glu Gln Leu Ala Glu Gln Leu Ala
            20                  25                  30

Arg Ala Phe Glu Ala Phe Ala Arg Ala Gly
        35                  40

<210> SEQ ID NO 22
<211> LENGTH: 42
<212> TYPE: PRT
```

-continued

```
<213> ORGANISM: Artificial Sequence
<220> FEATURE:
<223> OTHER INFORMATION: Synthesized
<220> FEATURE:
<221> NAME/KEY: VARIANT
<222> LOCATION: (10)..(10)
<223> OTHER INFORMATION: Amino acid capable of forming amide bond with
      reporter group
<220> FEATURE:
<221> NAME/KEY: VARIANT
<222> LOCATION: (17)..(17)
<223> OTHER INFORMATION: Amino acid capable of forming amide bond with
      ligand

<400> SEQUENCE: 22

Asn Ala Ala Asp Leu Glu Ala Ala Ile Xaa His Leu Ala Glu Ala Leu
1               5                   10                  15

Xaa Ala Arg Gly Pro Val Asp Ala Ala Gln Leu Ala Glu Gln Leu Ala
            20                  25                  30

Arg Ala Phe Glu Ala Phe Ala Arg Ala Gly
        35                  40

<210> SEQ ID NO 23
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (10)..(10)
<223> OTHER INFORMATION: Amino acid capable of forming amide bond with
      reporter group
<220> FEATURE:
<221> NAME/KEY: VARIANT
<222> LOCATION: (17)..(17)
<223> OTHER INFORMATION: Amino acid capable of forming amide bond with
      ligand

<400> SEQUENCE: 23

Asn Ala Ala Asp Leu Glu Ala Arg Ile Xaa His Leu Ala Glu Arg Leu
1               5                   10                  15

Xaa Ala Arg Gly Pro Val Asp Ala Ala Gln Leu Ala Glu Gln Leu Ala
            20                  25                  30

Arg Ala Phe Glu Ala Phe Ala Arg Ala Gly
        35                  40

<210> SEQ ID NO 24
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (10)..(10)
<223> OTHER INFORMATION: Amino acid capable of forming amide bond with
      reporter group
<220> FEATURE:
<221> NAME/KEY: VARIANT
<222> LOCATION: (17)..(17)
<223> OTHER INFORMATION: Amino acid capable of forming amide bond with
      ligand

<400> SEQUENCE: 24

Asn Ala Ala Asp Leu Glu Ala Arg Ile Xaa His Leu Arg Glu Arg Leu
1               5                   10                  15

Xaa Ala Arg Gly Pro Arg Asp Ala Ala Gln Leu Ala Glu Gln Leu Ala
            20                  25                  30
```

Arg Ala Phe Glu Arg Phe Ala Arg Ala Gly
        35                  40

<210> SEQ ID NO 25
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (22)..(22)
<223> OTHER INFORMATION: Amino acid capable of forming amide bond with
      ligand
<220> FEATURE:
<221> NAME/KEY: VARIANT
<222> LOCATION: (25)..(25)
<223> OTHER INFORMATION: Amino acid capable of forming amide bond with
      reporter group

<400> SEQUENCE: 25

Asn Glu Ala Asp Leu Glu Ala Ala Ile Arg His Leu Ala Glu Ala Leu
1               5                   10                  15

Glu Ala Arg Gly Pro Xaa Asp Ala Xaa Gln Leu Ala Glu Gln Leu Ala
            20                  25                  30

Arg Ala Phe Glu Ala Phe Glu Arg Ala Gly
        35                  40

<210> SEQ ID NO 26
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (22)..(22)
<223> OTHER INFORMATION: Amino acid capable of forming amide bond with
      ligand
<220> FEATURE:
<221> NAME/KEY: VARIANT
<222> LOCATION: (25)..(25)
<223> OTHER INFORMATION: Amino acid capable of forming amide bond with
      reporter group

<400> SEQUENCE: 26

Asn Glu Ala Asp Leu Glu Ala Ala Ile Arg His Leu Ala Glu Ala Leu
1               5                   10                  15

Ala Ala Arg Gly Pro Xaa Asp Ala Xaa Gln Leu Ala Glu Gln Leu Ala
            20                  25                  30

Arg Ala Phe Glu Ala Phe Ala Arg Ala Gly
        35                  40

<210> SEQ ID NO 27
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (22)..(22)
<223> OTHER INFORMATION: Amino acid capable of forming amide bond with
      ligand
<220> FEATURE:
<221> NAME/KEY: VARIANT
<222> LOCATION: (25)..(25)
<223> OTHER INFORMATION: Amino acid capable of forming amide bond with
      reporter group

<400> SEQUENCE: 27

Asn Ala Ala Asp Leu Glu Ala Ala Ile Arg His Leu Ala Glu Arg Leu
1               5                   10                  15

Ala Ala Arg Gly Pro Xaa Asp Ala Xaa Gln Leu Ala Glu Gln Leu Ala
            20                  25                  30

Arg Ala Phe Glu Ala Phe Ala Arg Ala Gly
            35                  40

<210> SEQ ID NO 28
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (22)..(22)
<223> OTHER INFORMATION: Amino acid capable of forming amide bond with
      ligand
<220> FEATURE:
<221> NAME/KEY: VARIANT
<222> LOCATION: (25)..(25)
<223> OTHER INFORMATION: Amino acid capable of forming amide bond with
      reporter group

<400> SEQUENCE: 28

Asn Ala Ala Asp Leu Glu Ala Arg Ile Arg His Leu Arg Glu Arg Leu
1               5                   10                  15

Ala Ala Arg Gly Pro Xaa Asp Ala Xaa Gln Leu Ala Glu Gln Leu Ala
            20                  25                  30

Arg Ala Phe Glu Arg Phe Ala Arg Ala Gly
            35                  40

<210> SEQ ID NO 29
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (34)..(34)
<223> OTHER INFORMATION: Amino acid capable of forming amide bond with
      ligand
<220> FEATURE:
<221> NAME/KEY: VARIANT
<222> LOCATION: (37)..(37)
<223> OTHER INFORMATION: Amino acid capable of forming amide bond with
      reporter group

<400> SEQUENCE: 29

Asn Glu Ala Asp Leu Glu Ala Ala Ile Arg His Leu Ala Glu Arg Leu
1               5                   10                  15

Glu Ala Arg Gly Pro Ala Asp Ala Ala Gln Leu Ala Glu Gln Leu Ala
            20                  25                  30

Ala Xaa Phe Glu Xaa Phe Ala Arg Ala Gly
            35                  40

<210> SEQ ID NO 30
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: VARIANT

```
<222> LOCATION: (34)..(34)
<223> OTHER INFORMATION: Amino acid capable of forming amide bond with
      ligand
<220> FEATURE:
<221> NAME/KEY: VARIANT
<222> LOCATION: (37)..(37)
<223> OTHER INFORMATION: Amino acid capable of forming amide bond with
      reporter group

<400> SEQUENCE: 30

Asn Ala Ala Asp Leu Glu Ala Ala Ile Arg His Leu Ala Glu Arg Leu
1               5                   10                  15

Ala Ala Arg Gly Pro Val Asp Ala Ala Gln Leu Ala Glu Gln Leu Ala
            20                  25                  30

Ala Xaa Phe Glu Xaa Phe Ala Arg Ala Gly
        35                  40

<210> SEQ ID NO 31
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (34)..(34)
<223> OTHER INFORMATION: Amino acid capable of forming amide bond with
      ligand
<220> FEATURE:
<221> NAME/KEY: VARIANT
<222> LOCATION: (37)..(37)
<223> OTHER INFORMATION: Amino acid capable of forming amide bond with
      reporter group

<400> SEQUENCE: 31

Asn Ala Ala Asp Leu Glu Ala Ala Ile Arg His Leu Ala Glu Arg Leu
1               5                   10                  15

Ala Ala Arg Gly Pro Val Asp Ala Ala Gln Leu Ala Glu Gln Leu Ala
            20                  25                  30

Arg Xaa Phe Glu Xaa Phe Ala Arg Ala Gly
        35                  40

<210> SEQ ID NO 32
<211> LENGTH: 42
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (34)..(34)
<223> OTHER INFORMATION: Amino acid capable of forming amide bond with
      ligand
<220> FEATURE:
<221> NAME/KEY: VARIANT
<222> LOCATION: (37)..(37)
<223> OTHER INFORMATION: Amino acid capable of forming amide bond with
      reporter group

<400> SEQUENCE: 32

Asn Ala Ala Asp Leu Glu Ala Arg Ile Arg His Leu Arg Glu Arg Leu
1               5                   10                  15

Ala Ala Arg Gly Pro Arg Asp Ala Ala Gln Leu Ala Glu Gln Leu Ala
            20                  25                  30

Arg Xaa Phe Glu Xaa Phe Ala Arg Ala Gly
        35                  40
```

COMPOUNDS AND METHODS

CROSS-REFERENCE TO RELATED APPLICATIONS

This application is a U.S. National Stage patent application pursuant to 35 U.S.C. §371 of International Patent Application PCT/EP2011/065421, filed on Sep. 6, 2011, and published as WO 2012/032068 on Mar. 15, 2012, which claims priority to U.S. Provisional Patent Application Ser. No. 61/382,171, filed on Sep. 13, 2010, European Patent Application No. 10176360.5, filed on Sep. 13, 2010, and Swedish Application No. 1000906-6 filed on Sep. 6, 2010; the content of each is hereby expressly incorporated by reference in their entireties for all purposes.

FIELD OF THE INVENTION

The present invention relates to the field of biotechnology. More specifically the invention relates to the novel polypeptides and molecular tools based on these polypeptides as well as methods where such tools are used and products obtained using these tools.

BACKGROUND OF THE INVENTION

Some folded ligand-modified helix-loop-helix polypeptide scaffolds that connect the key biosensing events of recognition and reporting are described in WO 03/080653, which also teaches the use of said polypeptide scaffolds in bioanalytical/biosensor applications and in biosensors for determination of protein concentrations and/or protein affinities.

Also, different ligand-modified polypeptides have been previously described as capable of binding a number of specified target molecules. Thus, in WO 07/117,215 a polypeptide dimer is disclosed, to which at least one phosphocholine derivative is attached, whereby the polypeptide obtained shows a specific binding for C-reactive protein (CRP). Likewise, in the above-mentioned WO 03/080653 the binding of a ligand-polypeptide conjugate to human carbonic anhydrase II is disclosed.

SUMMARY OF THE INVENTION

The present inventors now have surprisingly found that by use of a set of polypeptides selected from as few as 16 different polypeptide sequences, polypeptide conjugate binders are obtainable having enhanced selectivity and/or affinity for a variety of target molecules.

Thus, by the set of polypeptides according to the invention a powerful tool is provided, permitting to obtain ligand-polypeptide conjugates as binders for a large variety of target molecules, which binders have substantially enhanced affinity and selectivity compared to the ligand per se.

A ligand-polypeptide conjugate obtainable by use of the tool of the invention comprises a ligand capable of binding to the target molecule attached to a polypeptide. It is a very advantageous feature of the invention that while the ligand per se (i.e. not attached to the polypeptide of the invention) may show only moderate affinity and/or selectivity for the target molecule, the conjugate molecule provided according to the invention advantageously will show a substantially enhanced affinity and/or selectivity.

It is a remarkable feature that the set of polypeptides of the invention may be used as a molecular tool of great versatility, permitting to find an optimum binder for a wide spectrum of target molecules.

Consequently, according to a first aspect of the invention a polypeptide having a sequence selected from SEQ ID NOs 1-32 is provided.

According to a further aspect, a plurality of polypeptides is provided comprising at least two different polypeptides according to the invention.

Furthermore, a molecular tool is provided, for use in a method of providing a molecule that is capable of binding a target molecule, said tool comprising a plurality of polypeptides according to any one or several of SEQ ID NOs 1-32, each polypeptide having a ligand capable of binding a target molecule attached by an amide bond to an amino acid capable of forming an amide bond with the ligand, said amino acid being in a position selected from positions 8, 17, 22, and 34 of the polypeptide sequence, and a reporter group, for detecting binding to a target molecule, attached by an amide bond to an amino acid capable of forming an amide bond with the reporter group, said amino acid being in a position selected from positions 15, 10, 25 and 37 of the polypeptide sequence.

By attaching a ligand for the target molecule to each member of the selected set of polypeptides and screening (e.g. in a high-throughput screening method) the obtained set of ligand-polypeptide conjugates for binding affinity and selectivity towards the conjugate molecule, an optimum ligand-polypeptide conjugate as binder for the target molecule may be identified. As will be shown herein, it is an advantageous feature of the invention that even using a moderate affinity and/or moderate selectivity ligand, the screening method will provide a binder having high affinity and/or selectivity for the target molecule or having an optimum combination of affinity and selectivity.

Therefore, according to another aspect, a method of screening for a ligand-polypeptide conjugate capable of binding a target molecule is provided, comprising providing at least one conjugate molecule comprising a polypeptide having a sequence selected from SEQ ID NOs 1-32, said polypeptide having a ligand for the target molecule attached by an amide bond to an amino acid capable of forming an amide bond with the ligand, said amino acid being at a position in the polypeptide sequence selected from positions 8, 17, 22, and 34, and said polypeptide having a reporter group attached by an amide bond to an amino acid capable of forming an amide bond with the reporter group, said amino acid being at a position in the polypeptide sequence selected from positions 15, 10, 25 and 37;

bringing the target molecule in contact with the conjugate molecule; and detecting a signal from the reporter group.

According to still a further aspect, a ligand-polypeptide conjugate is provided, comprising a polypeptide having a sequence selected from SEQ ID NOs 1-32, said polypeptide having a ligand for a target molecule attached by an amide bond to an amino acid capable of forming an amide bond with the ligand, said amino acid being in a position selected from positions 8, 17, 22, and 34 of the polypeptide sequence.

Also provided is a ligand-polypeptide conjugate as defined herein for use in therapy and a pharmaceutical composition comprising a ligand-polypeptide conjugate as defined herein.

Also provided is a ligand-polypeptide conjugate according to the invention, and diagnostic or therapeutic methods wherein such conjugate is used as well as a pharmaceutical composition or e.g. a diagnostic kit comprising a ligand-polypeptide conjugate according to the present invention.

Further aspects of the invention, as well as embodiments thereof, will be readily apparent from the following description and the appended claims.

BRIEF DESCRIPTION OF THE DRAWINGS

FIG. 1 is a one-letter code representation of a set of 16 polypeptides of the invention showing, at the left side of the sequences, the designation used herein for the polypeptide as well as the SEQ ID NO, and at the right side of the sequence, the net charge of the polypeptide. The lysine residue serving as site of attachment for ligand is written in bold.

FIG. 10. Titration with α-casein of polypeptide without PP1 attached (top) and by the tight binder 4-C10L17-PP1 in the absence of zinc ions (bottom). The addition of α-casein generates insignificant effects on fluorescence emission intensities. Both experiments show no or insignificant binding in the absence of fully assembled binder molecule.

(A) Lane 1. Positive control, α-casein. Lane 2. Extract from 500 nM solution of α-casein in 10 mM PBS buffer. (B) Lane 1. Positive control, α-casein. Lane 2. Extract from 500 nM solution of α-casein and 400 µM of phosphorylated peptide PhosPep1; Lane 3. Extract from 500 nM solution of α-casein and 40 µM of phosphorylated peptide PhosPep1; Lane 4. Extract from 100 nM solution of α-casein and 80 µM of phosphorylated peptide PhosPep1; Lane 5. Extract from 100 nM solution of α-casein and 8 µM of phosphorylated peptide PhosPep1; Lane 6. Negative control, extract from beads without binder from 500 nM α-casein and 400 µM of phosphorylated peptide PhosPep1. (C) Lane 1. Positive control, α-casein; Lane 2. Extract from 500 nM solution of α-casein, Lane 3. Extract from 500 nM solution of α-casein 80% dephosphorylated.

Figure 12:
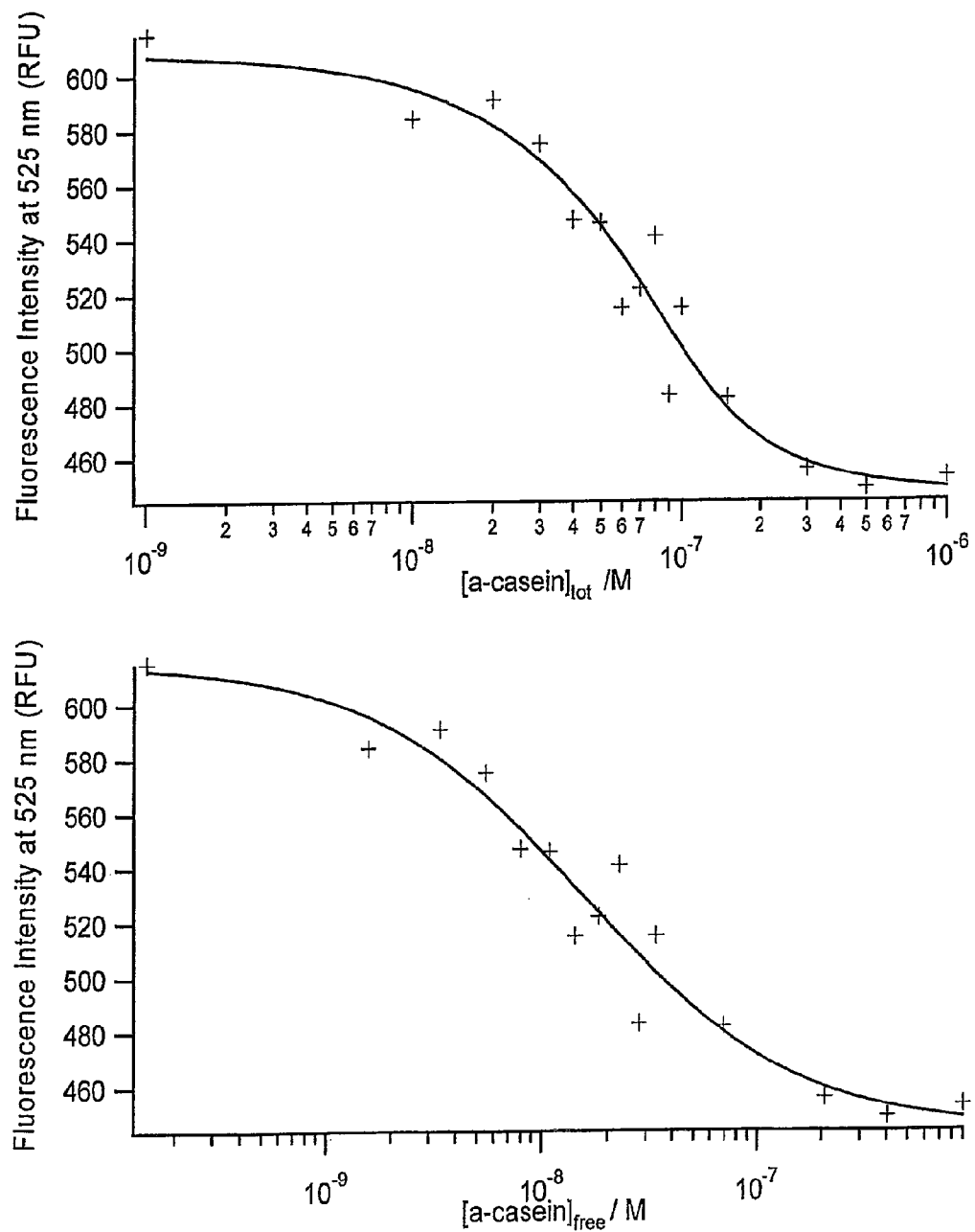

FIG. 12. Fluorescence intensities plotted against total concentration of α-casein (left) and free concentration of α-casein (right). A dissociation constant of 17 nM was obtained from the best fit to the experimental results of an equation describing the dissociation of a 1:1 complex.

Figure 13:
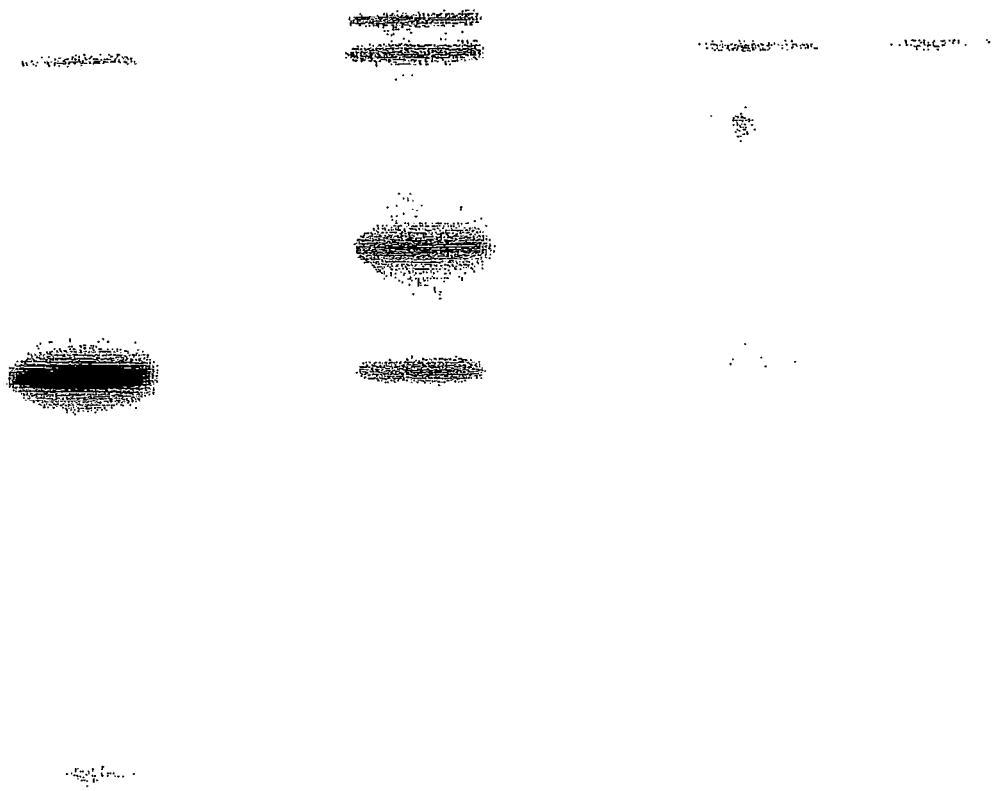

FIG. 13. SDS-PAGE of proteins extracted from protein mixture in pull-down experiment. The protein mixture contained lysozyme (15 kDa), phosphorylase B (97 kDa), β-galactosidase (116 kDa), α-casein and ovalbumin Lane 1: Extract by beads coated with 4-C15L8-PP1 covalently linked to Pluronic. Lane 2: Control. Extract by beads coated with Pluronic incubated in 500 nM solution of α-casein; Lane 3: 500 nM protein mixture; Lane 4: Extract by beads carrying 4-C15L8-PP1 lacking chelated $Zn^{2+}$ in 500 nM solution of α-casein; Lane 5: Extract by beads carrying 4-C15L8-PP1 lacking chelated $Zn^{2+}$ incubated in protein mixture; Lane 6: Extract by beads carrying 4-C15L8 peptide acetylated at Lys8 in protein mixture. Weak bands at the bottom of gel are binder molecule, MW 5 kD. 4-C15L8-PP1 specifically extracts α-casein from protein mixture.

Figure 14:
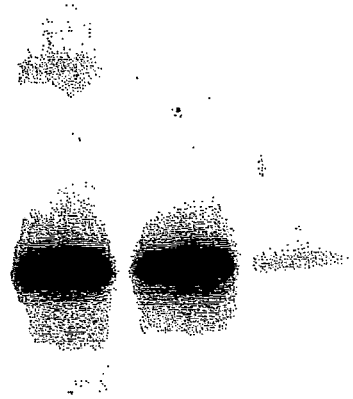

FIG. 14. Pull-down of β-casein by 4-C15L8-PP1 Lane 1. Positive control, β-casein. Lane 2: Extract from 100 nM solution of β-casein in 10 mM HEPES buffer with 150 mM NaCl at pH 7.2. Lane 3: Negative control. Extract by beads coated with Pluronic in 500 nM solution of β-casein.

Figure 15:
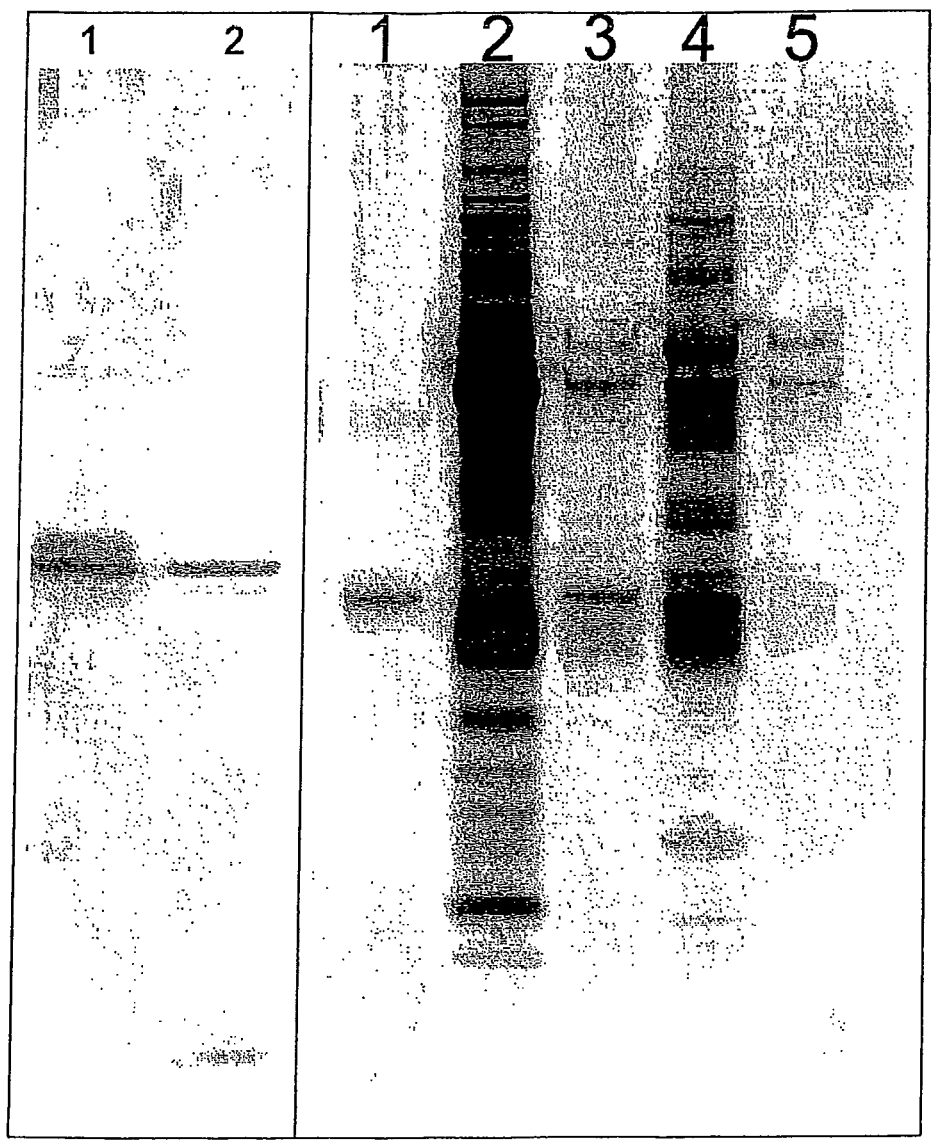

FIG. 15. Pull-down of α-casein by 4-C15L8-PP1 from milk and human serum. A) Lane 1. Positive control, α-casein. Lane 2. Extract from 10-fold diluted bovine milk. B) Lane 1. Positive control α-casein. Lane 2. Positive control human serum 100-fold diluted, spiked with α-casein to a concentration of 500 nM. Lane 3. Extract from human serum diluted 100-fold with buffer and spiked with 500 nM α-casein. Lane 4. Extract from neat human serum spiked with 500 nM α-casein. Lane 5. Extract from 100-fold diluted human serum spiked with 500 nM α-casein by beads coated only with Pluronic.

Figure 16:
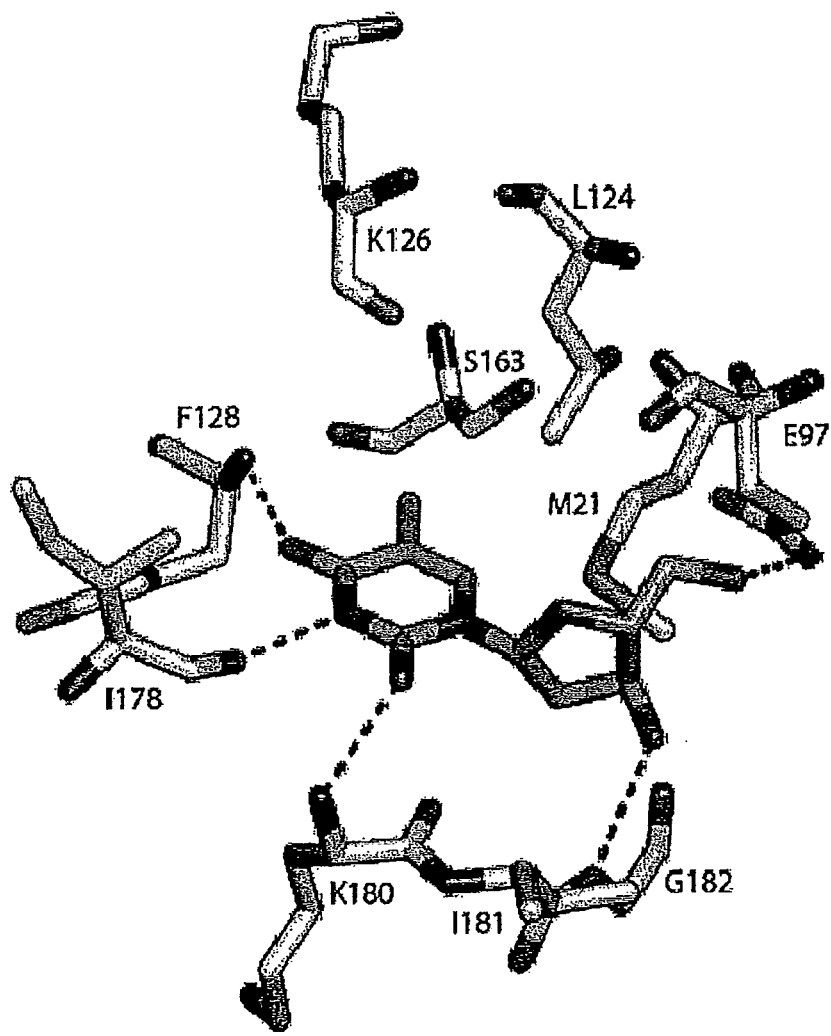

FIG. 16 shows a stick representation of the interaction between thymidine and TK from *Ureaplasma urealyticum*.

Figure 17:
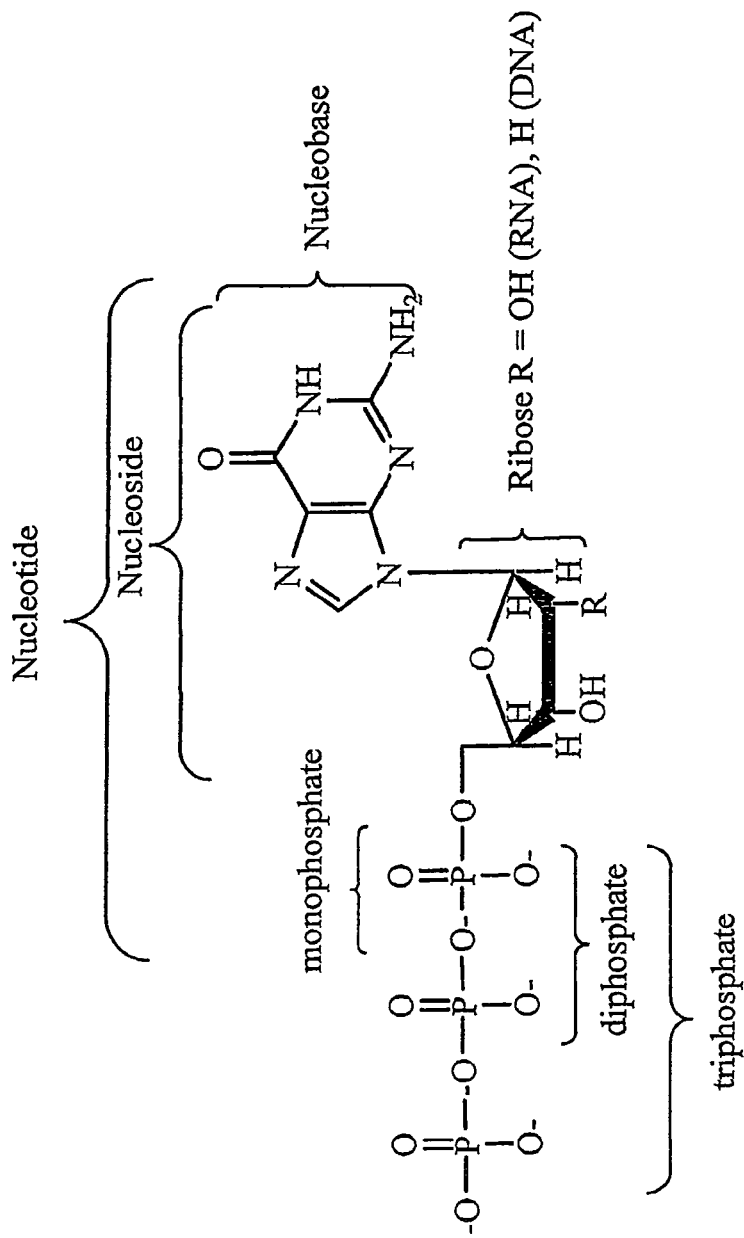

FIG. 17 shows the composition of nucleotide and nucleotide mono-, di-, and triphosphates. Here the nucleobase is guanine.

Figure 18:
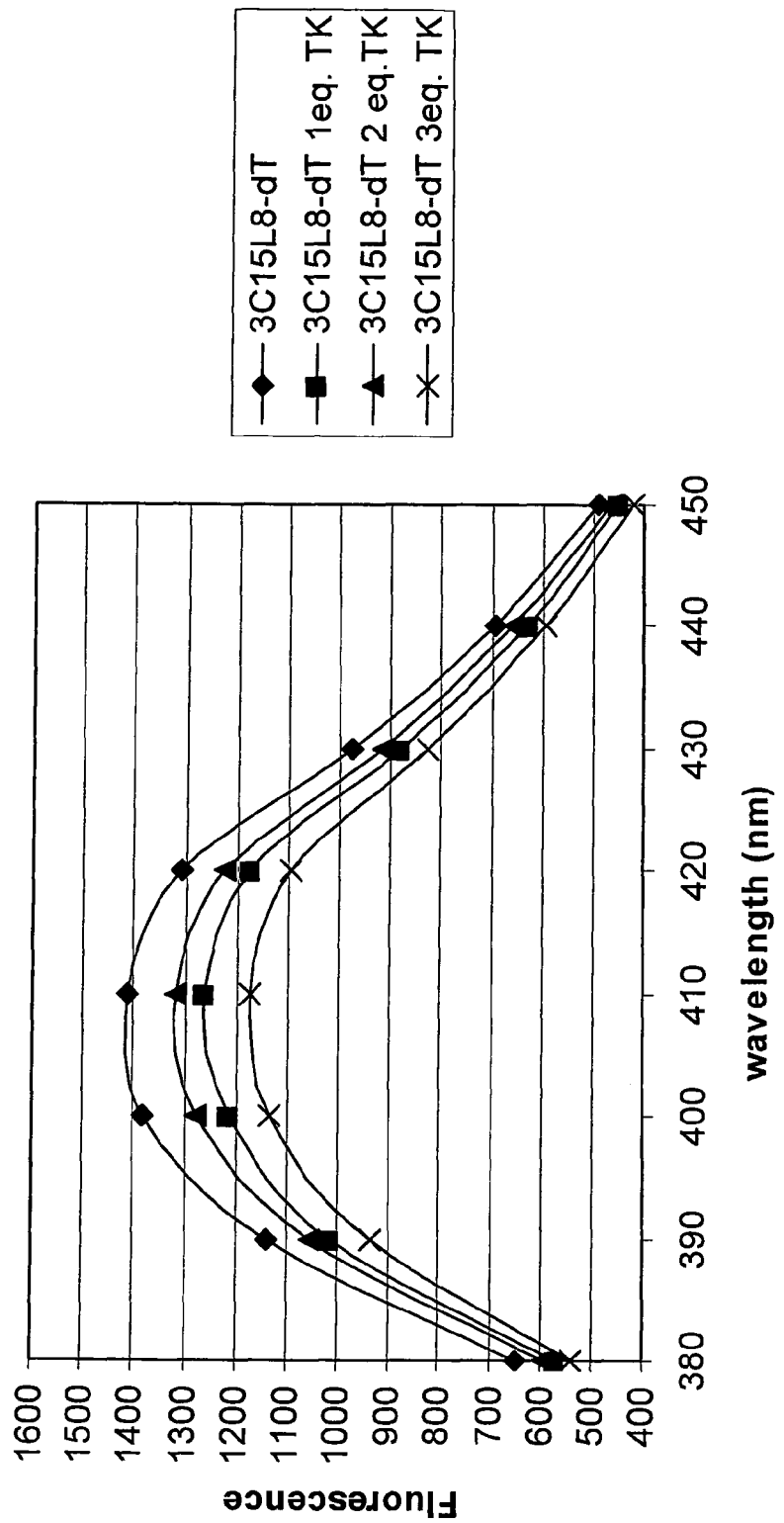

FIG. 18. Fluorescence spectrum for 3-C15L8-dT in buffer A (without ATP) after 45 min. Data points correspond to mean value of four separate measurements.

Figure 19:
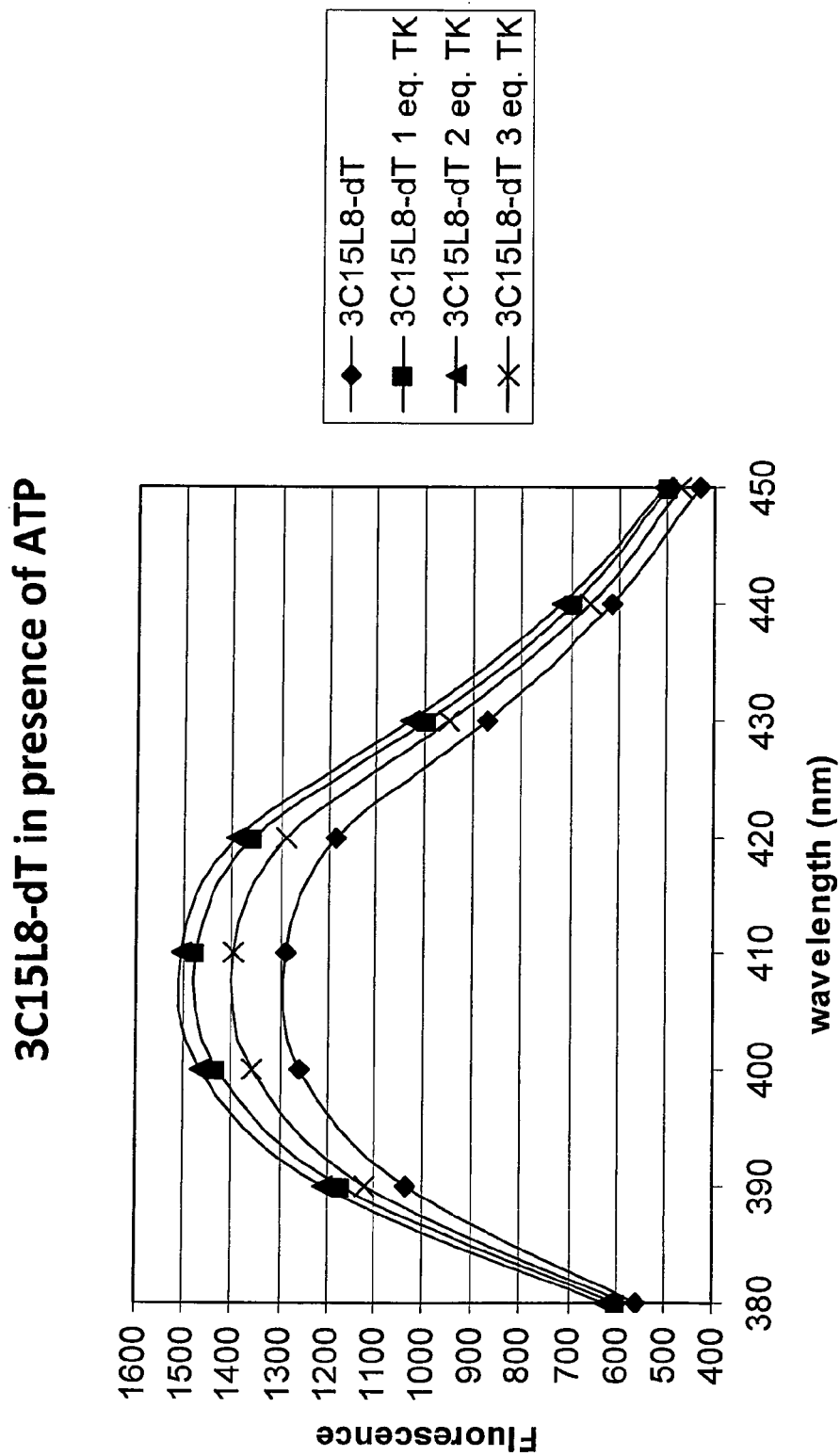

FIG. 19. Fluorescence spectrum for 3-C15L8-dT in buffer B (with ATP) after 45 min. Data points correspond to mean value of four separate measurements.

Figure 20:
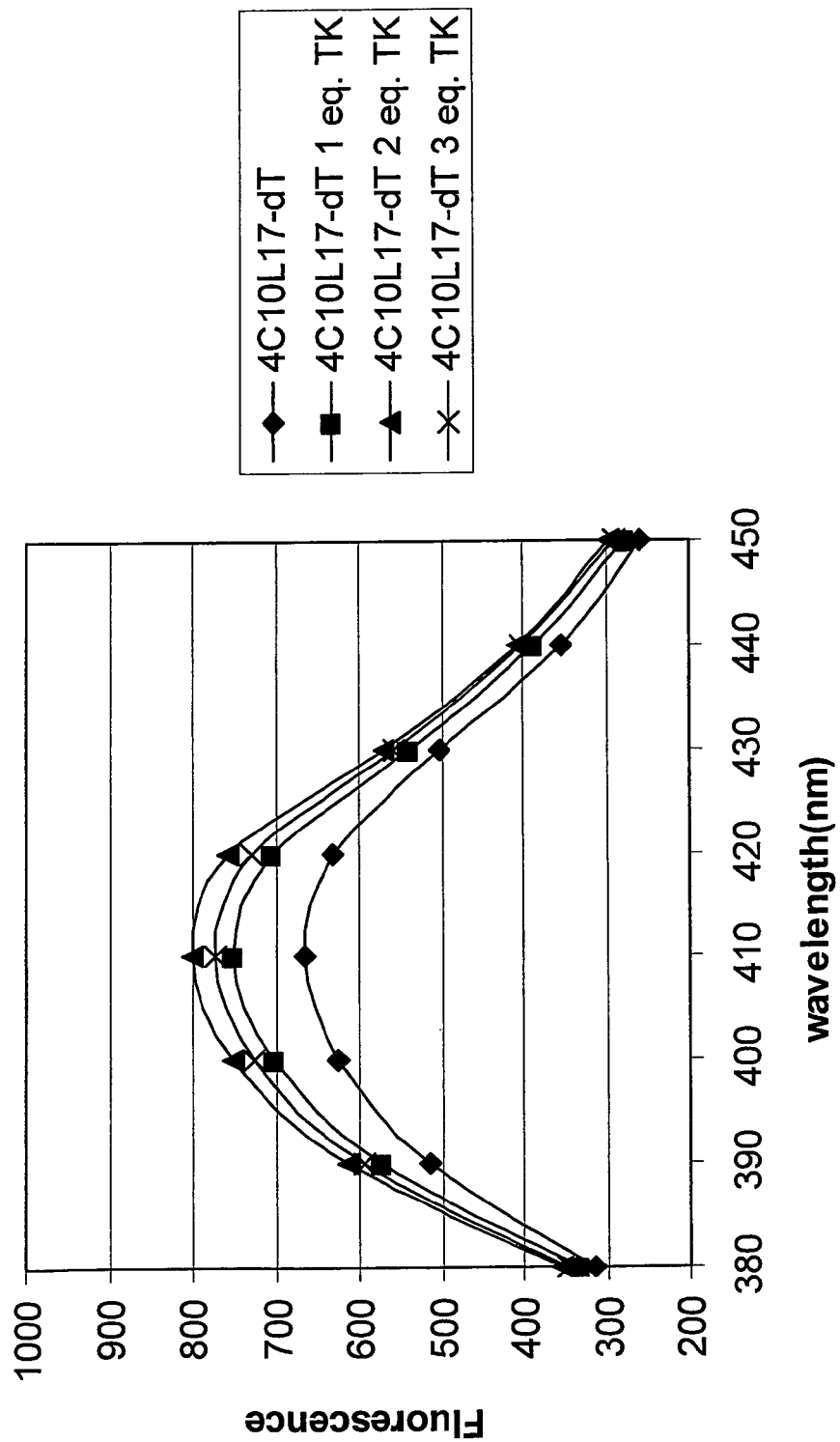

FIG. 20. Fluorescence spectrum for 4-C10L17-dT in buffer A (without ATP) after 45 min. Data points correspond to mean value of four separate measurements.

Figure 21:
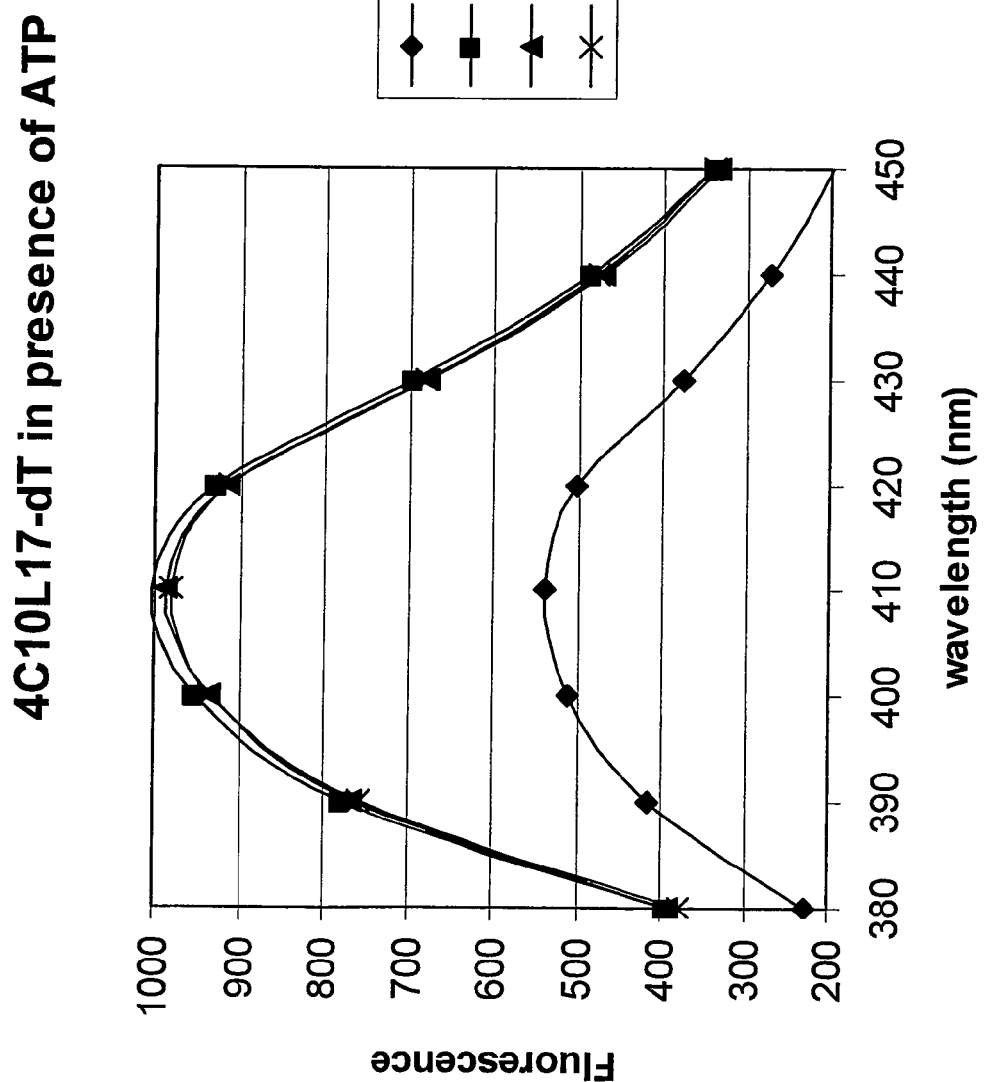

FIG. 21. Fluorescence spectrum for 4-C10L17-dT in buffer B (with ATP) after 45 min. Data points correspond to mean value of four separate measurements.

Figure 22:
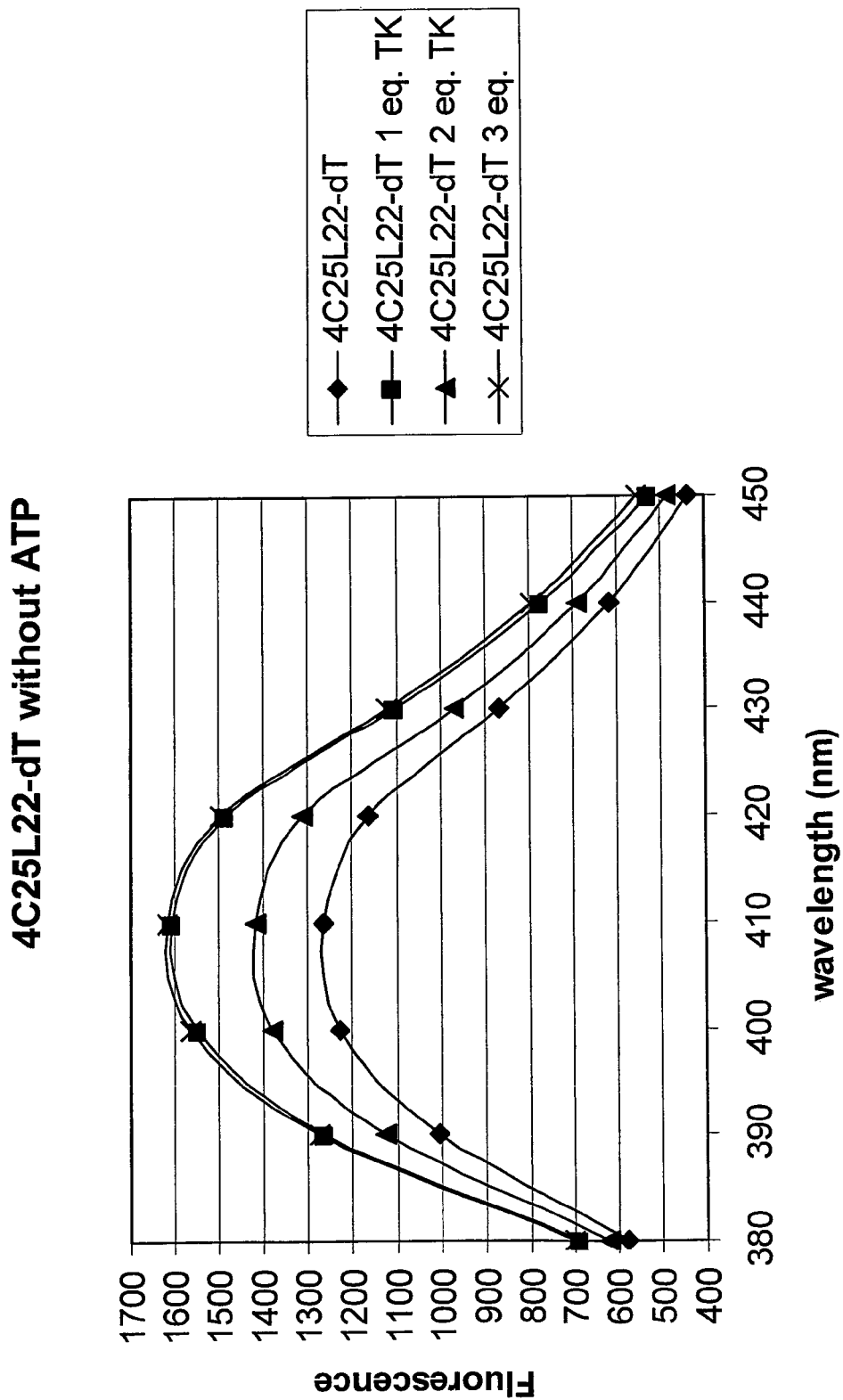

FIG. 22. Fluorescence spectrum for 4-C25L22-dT in buffer A (without ATP) after 45 min. Data points correspond to mean value of four separate measurements.

Figure 23:
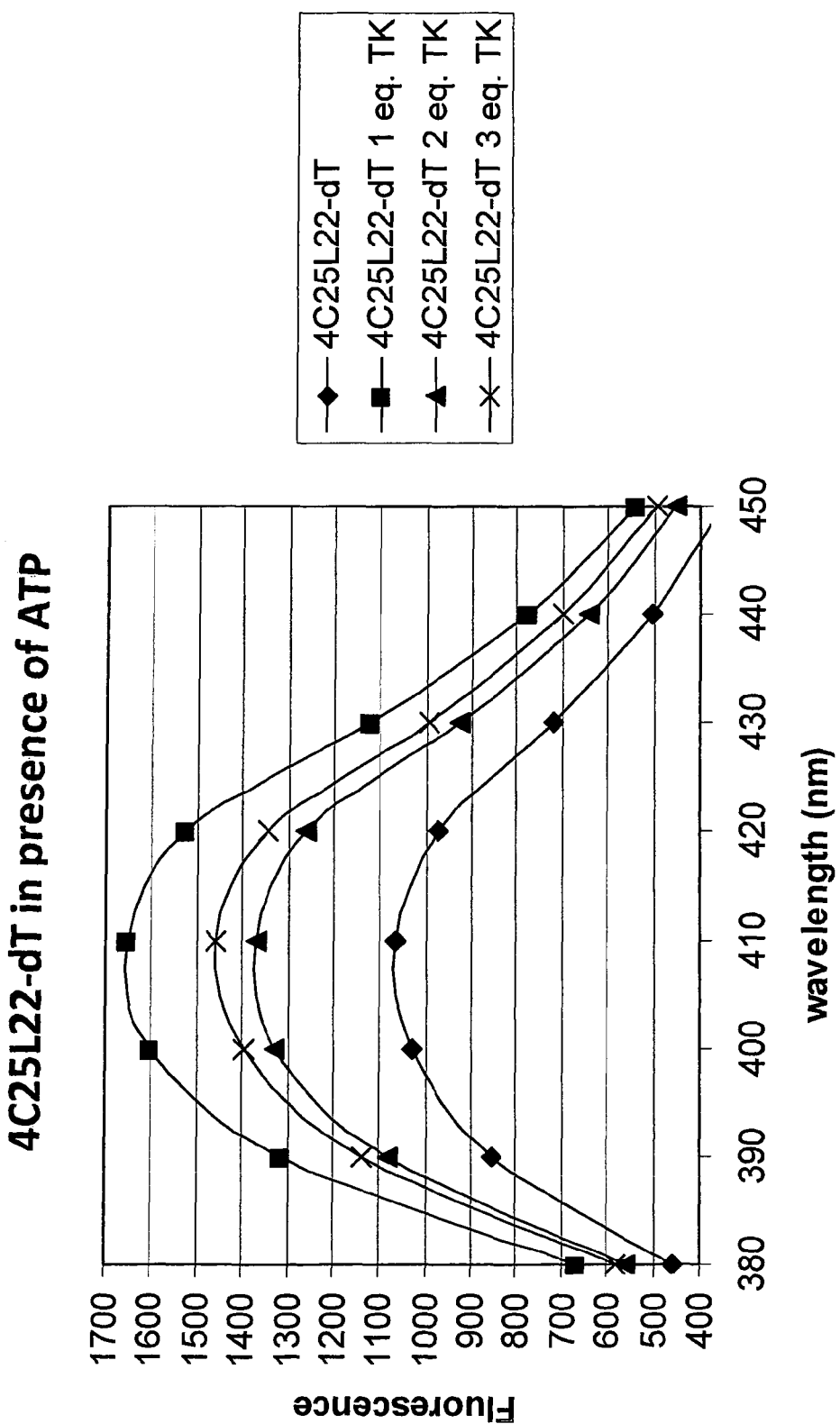

FIG. 23. Fluorescence spectrum for 4-C25L22-dT in buffer B (with ATP) after 45 min. Data points correspond to mean value of four separate measurements.

Figure 24:
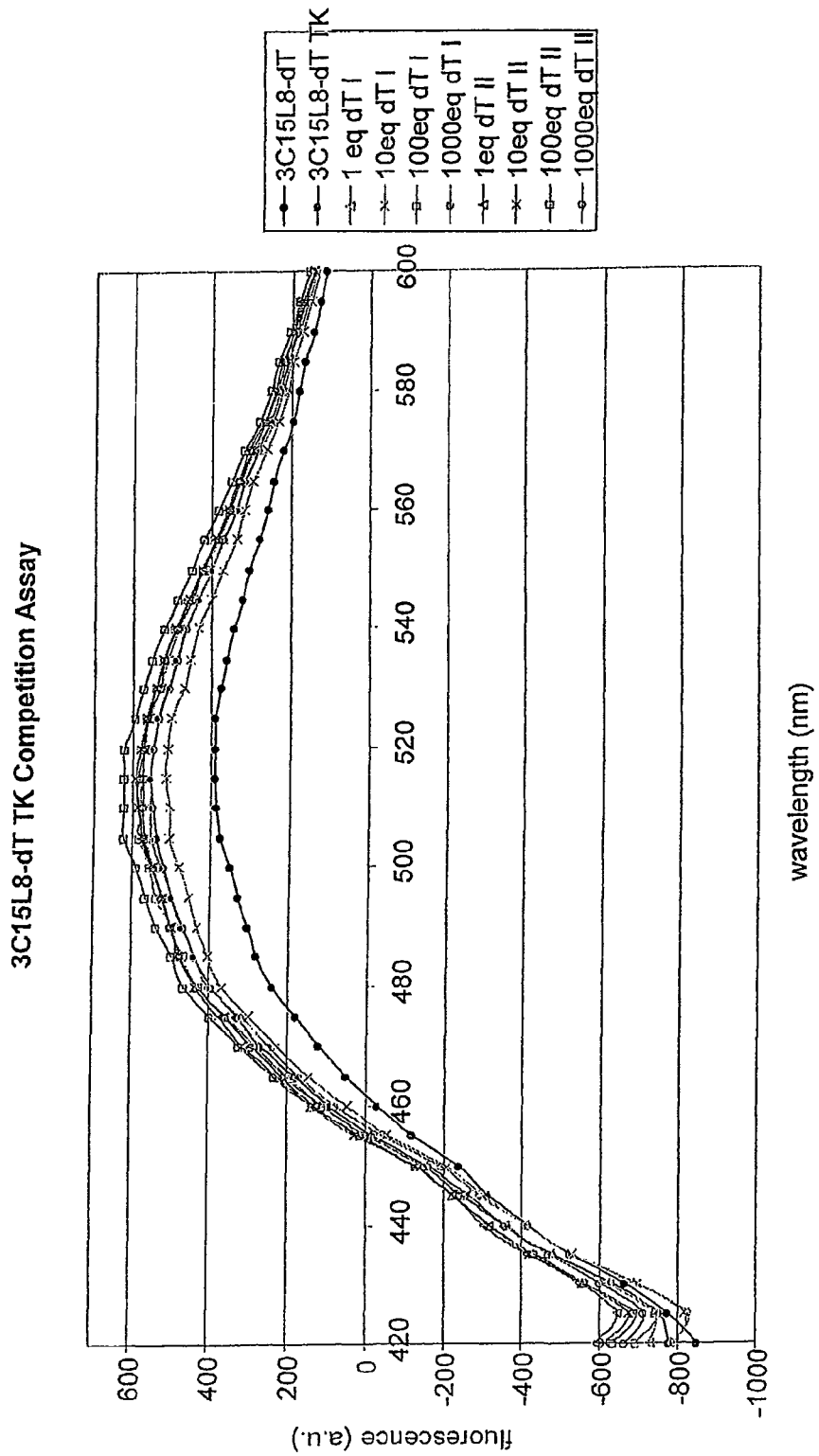

FIG. 24. 3-C15L8-dT fluorescence spectrum of competition assays with dT on TK in 20 mM Tris buffer and at 2 µM peptide concentration. Data points correspond to an averaged value of three separate measurements.

Figure 2:
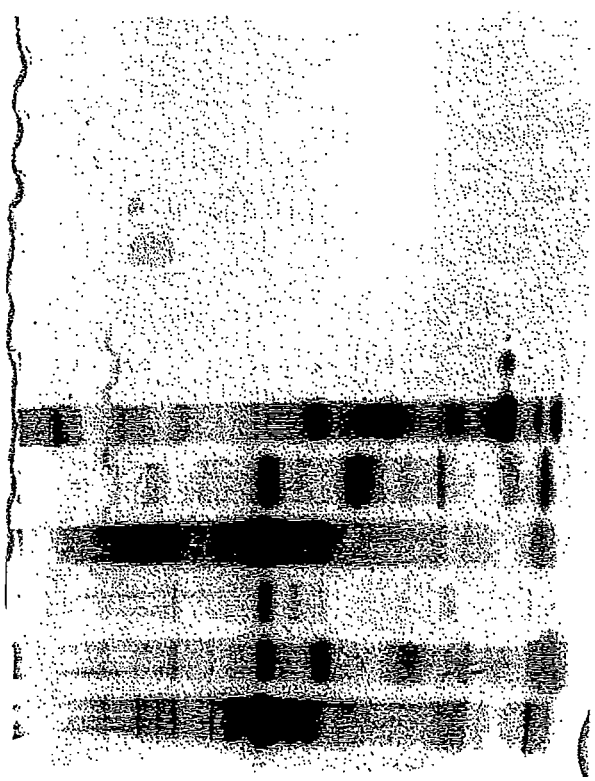
FIG. 2 shows an electrophoresis gel obtained in Example 1, from left; 1. CSF (10× diluted), 2. Proteins captured from CSF by PS-F108-4-C10L17-Ac, 3. Unspecific uptake by particles with Pluronic F108, 4. hAChE (Sigma), 5. MW standard (97 (very weak), 65, 40, 30, 20.1, 14.4 kDa), 6. Prestained MW standard.
Figure 25:
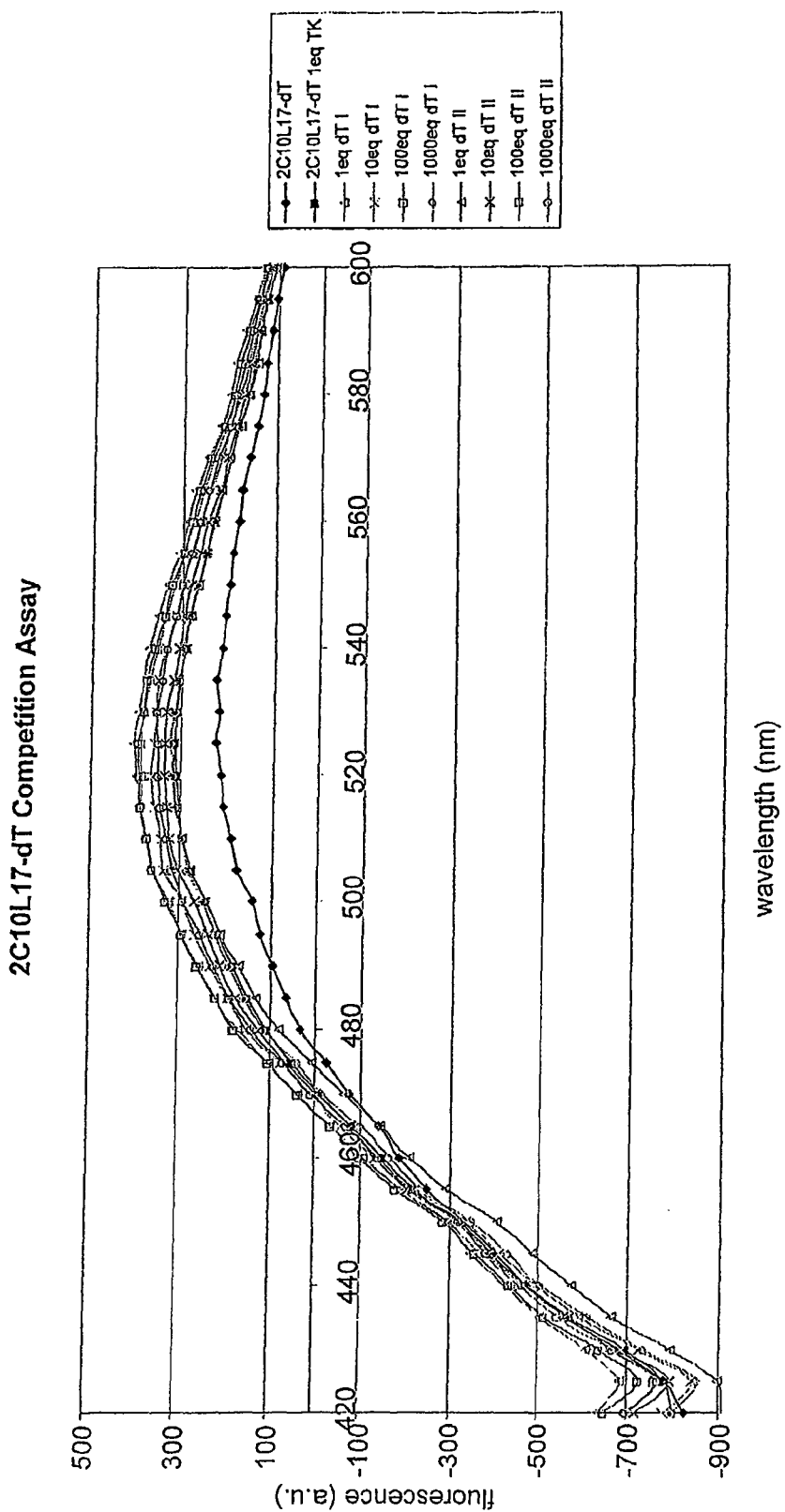

FIG. 25 2-C10L17-dT fluorescence spectrum of competition assays with dT on TK in 20 mM Tris buffer and at 2 µM peptide concentration. Data points correspond to an averaged value of three separate measurements.

Figure 4:
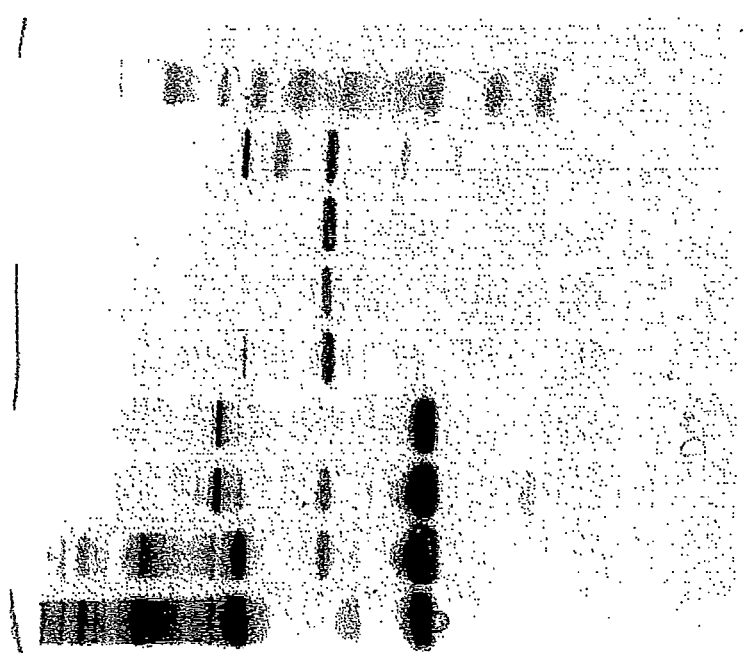
FIG. 4 shows silver stained electrophoretic gel showing proteins extracted from lysed blood in Example 2. From left to right 1: Proteins from serum diluted 500 times. 2. Proteins from lysed blood diluted 500 times. 3. Proteins captured by binder 3-C15L8-B. 4. Proteins captured by 4-C37L34-B. 5. Mixture of commercially available HCAI and HCAII. 6. HCAI. 7. HCAII. 8. MW standard (top to bottom 97, 65, 40, 30, 20.1 and 14.4 kDa). 9. Prestained MW standard. The bands were cut out and in-gel tryptic digestion followed by MALDI-TOF-MS analysis, displaying the origin of the bands. The band at 70 kDa contains HSA, the band at 30 kDA contains both HCAI and HCAII, and the band at 20 kDa contains fragments from hemoglobin. The bands at 70 kDa is present in all samples and are due to unspecific interaction of HSA and the beads, the hemoglobin band originates from clotted hemoglobin fragments, which are following the beads throughout the centrifugations.
Figure 26:
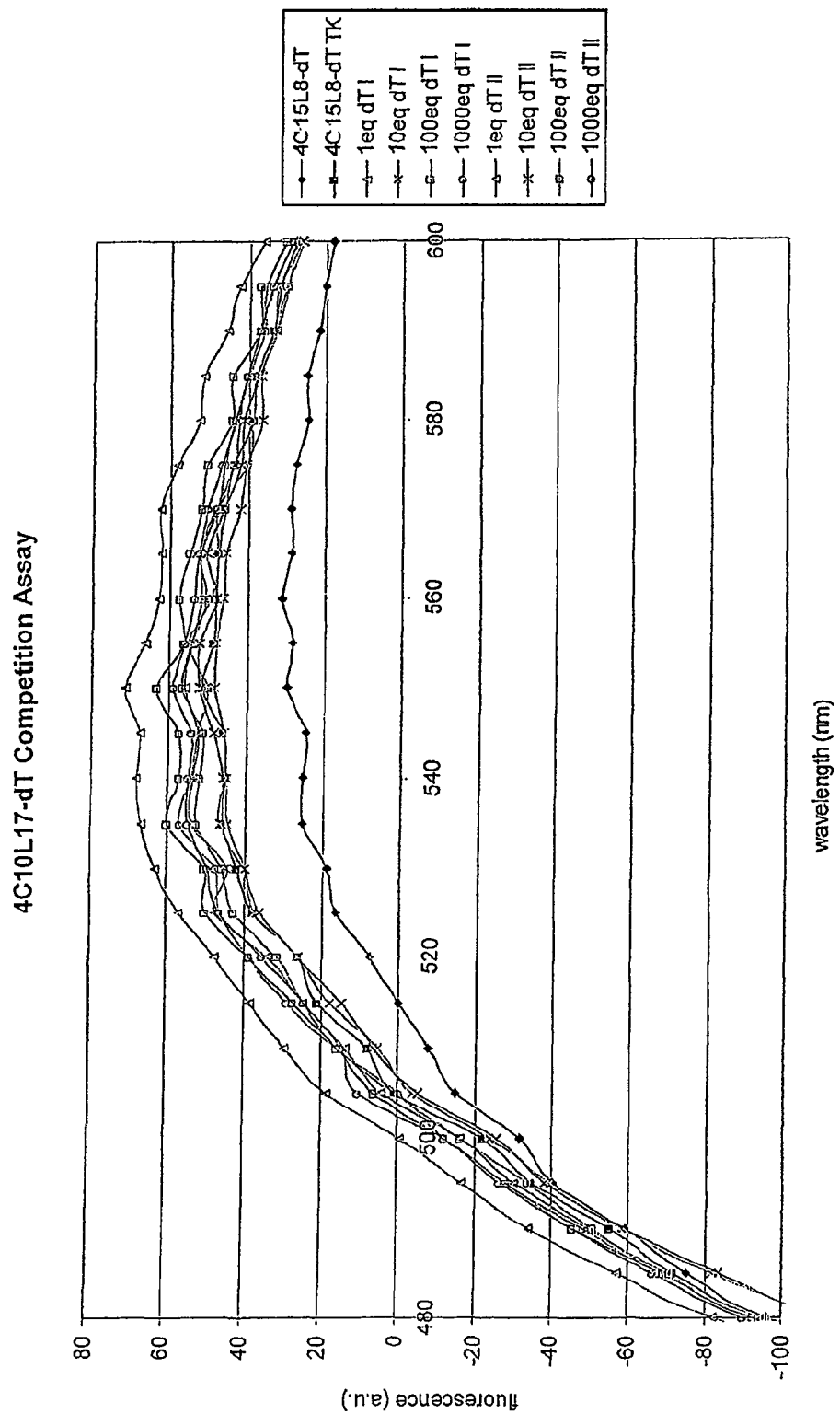

FIG. 26 4-C10L17-dT fluorescence spectrum of competition assays with dT on TK in 20 mM Tris buffer and at 2 µM peptide concentration. Data points correspond to an averaged value of three separate measurements. Data points from 420-475 nm are omitted for better clarity of the figure.

Figure 3:
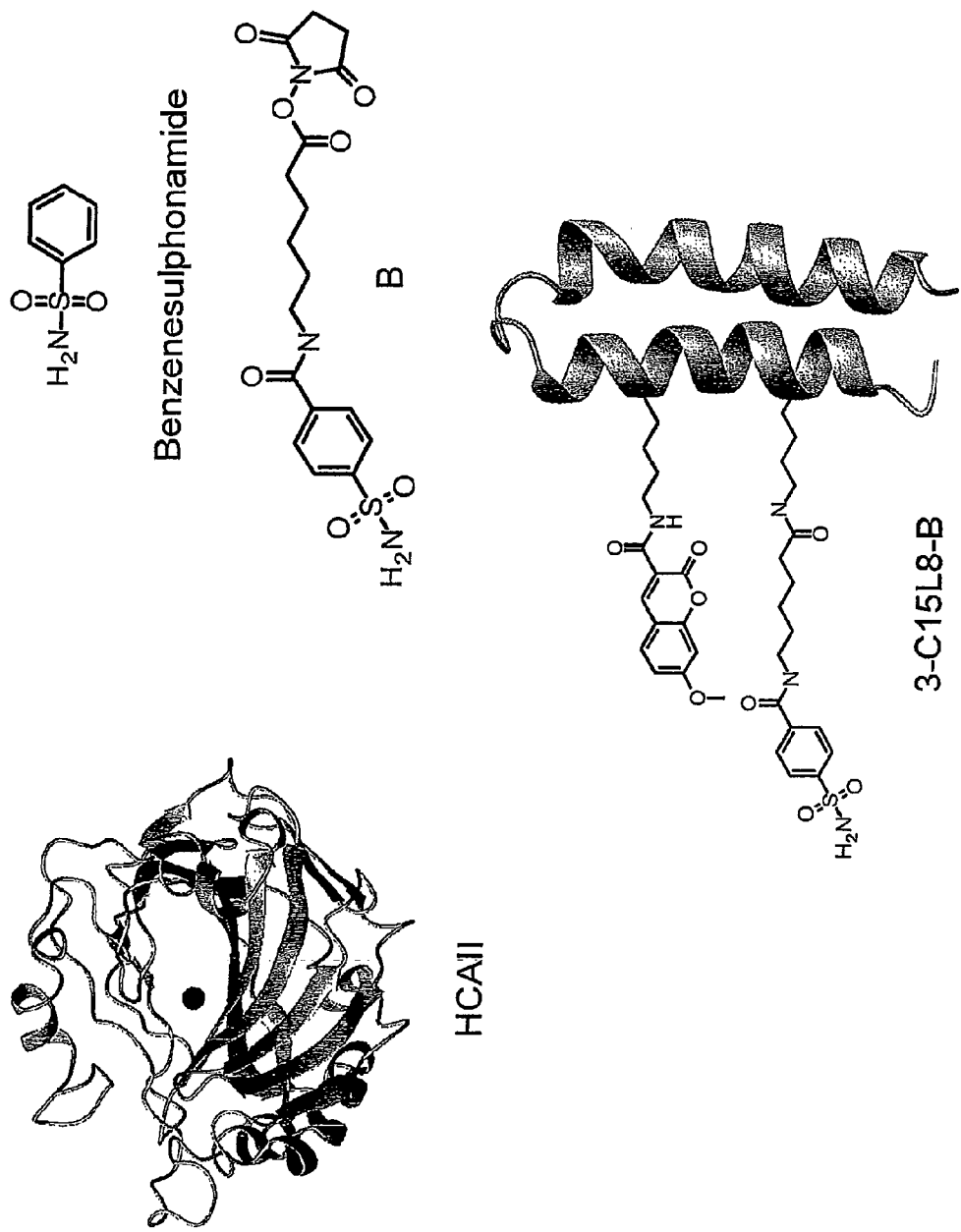
FIG. 3 shows a ribbon band illustration of human carbonic anhydrase II (HCAII), used as target molecule in Example 2, with the $Zn^{2+}$ ion visible as a black circle in the active site of the enzyme. Also shown are the ligand L, which here is benzenesulphonamide, a known inhibitor of HCAII; an active ester derivative of the ligand L attached to a spacer arm; and a polypeptide of the invention (3-C15L8) to which the spacer arm carrying L is attached in position 8 and to which also a fluorophore as a reporter group is attached in position 15.
Figure 27:
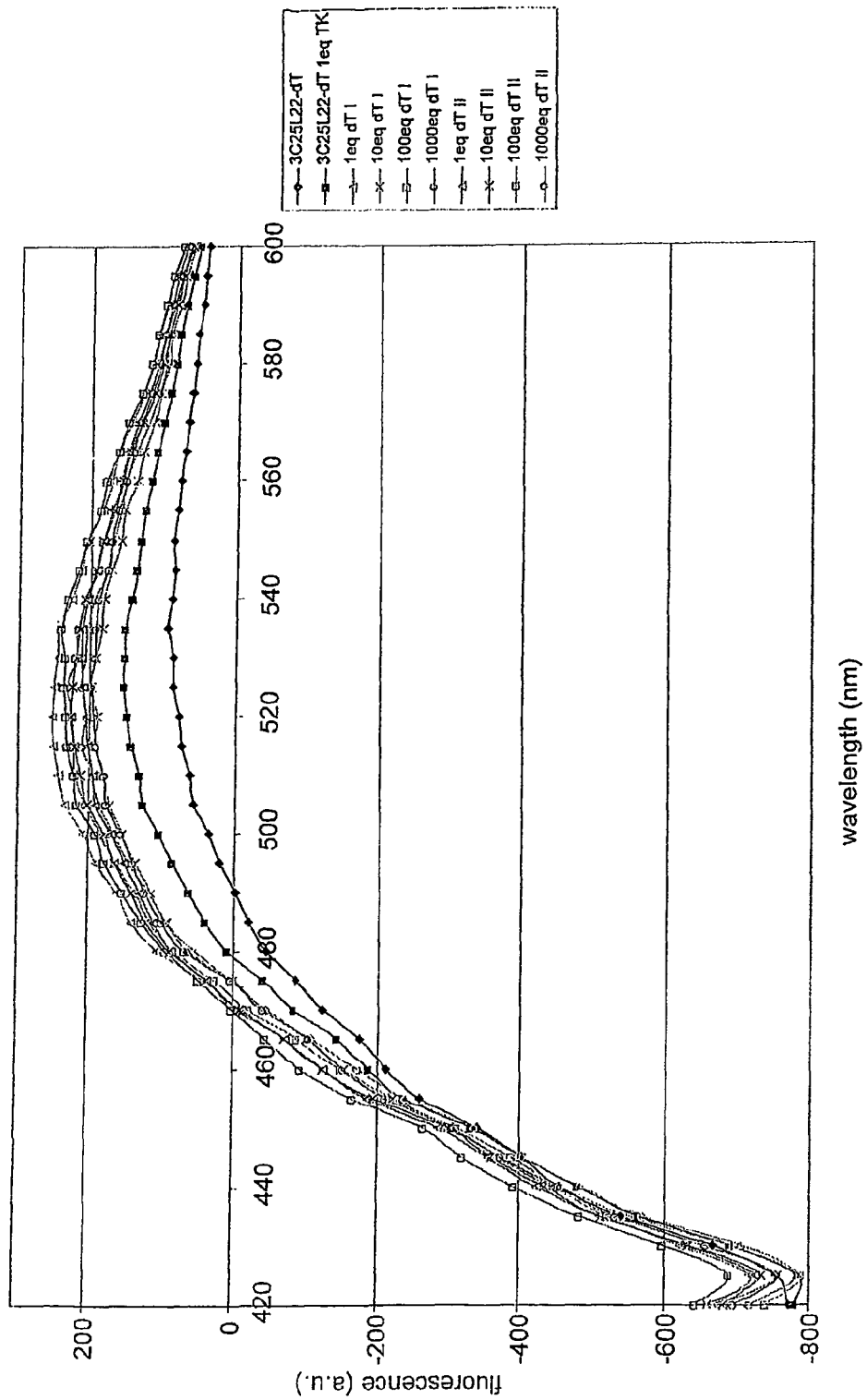

FIG. 27 3-C25L22-dT fluorescence spectrum of competition assays with dT on TK in 20 mM Tris buffer and at 2 µM peptide concentration. Data points correspond to an averaged value of three separate measurement.

Figure 28:
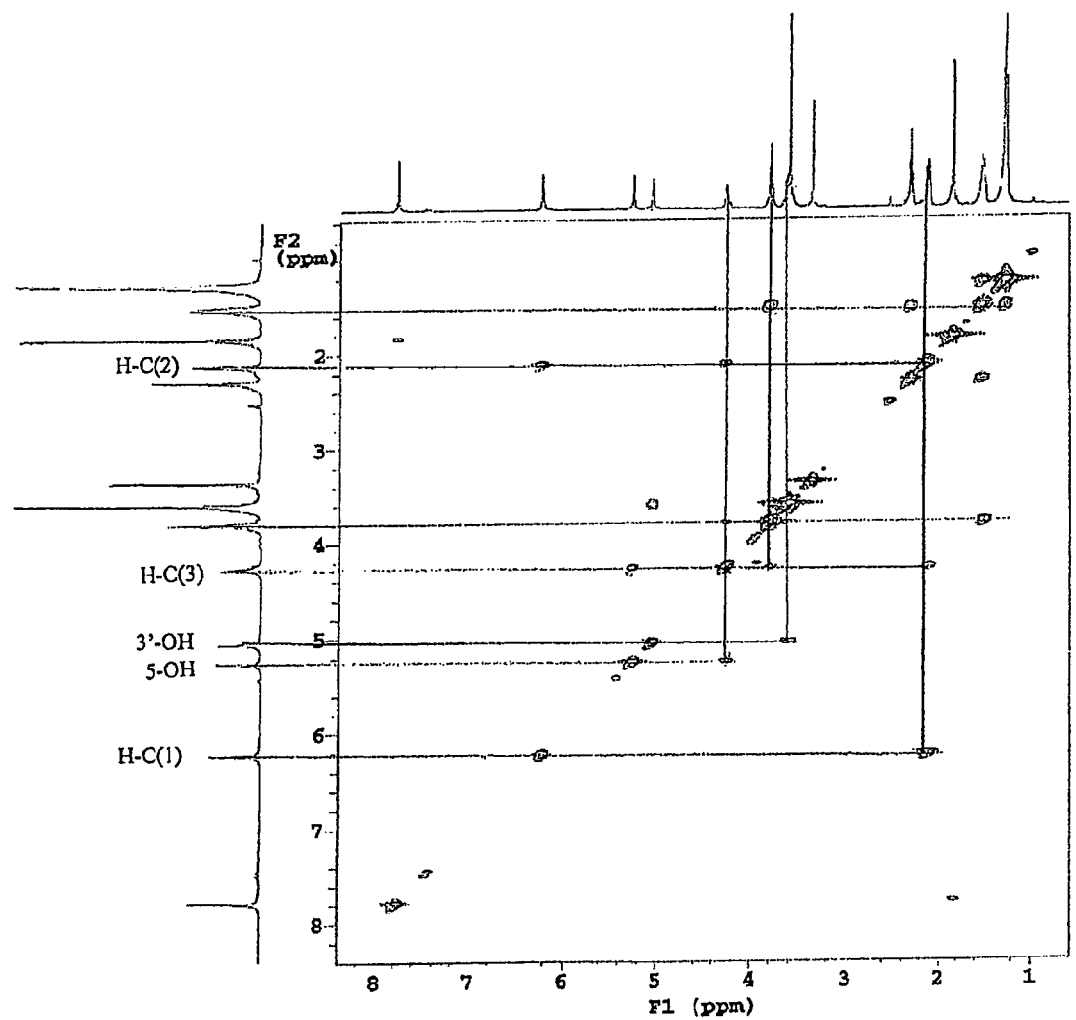

FIG. 28 1H/1H-COSY in DMSO-d6 of 19.

Figure 29:
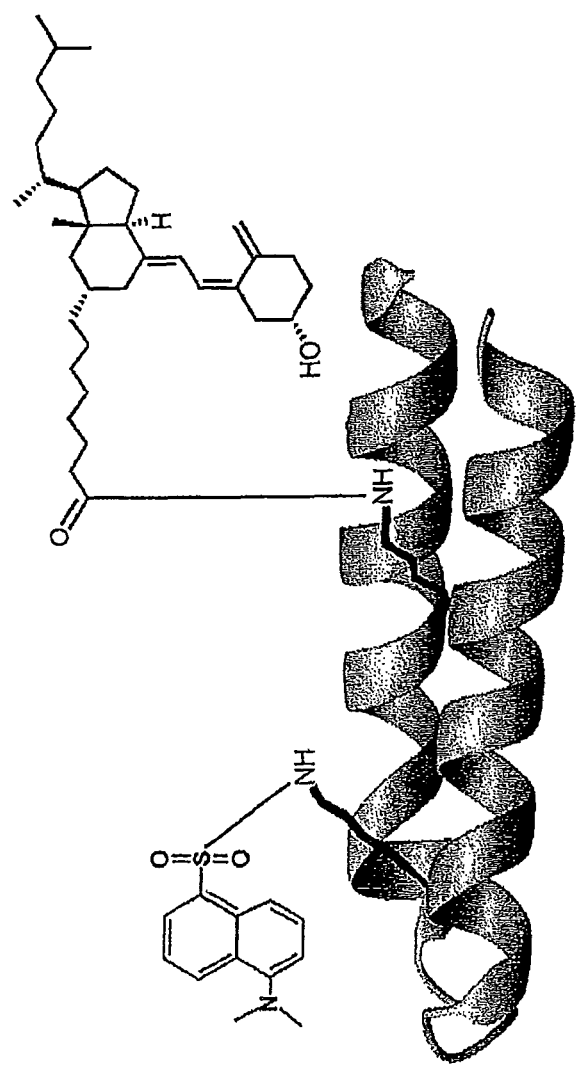

FIG. 29 shows an illustration of a binder molecule for vitamin D binding protein. Small molecule ligand is attached via 8 carbon spacer to side chain of lysine residue in the peptide sequence. A dansyl fluorophor is incorporated for purposes of quantification, and for fluorescence titration of affinity for the protein.

Figure 30:
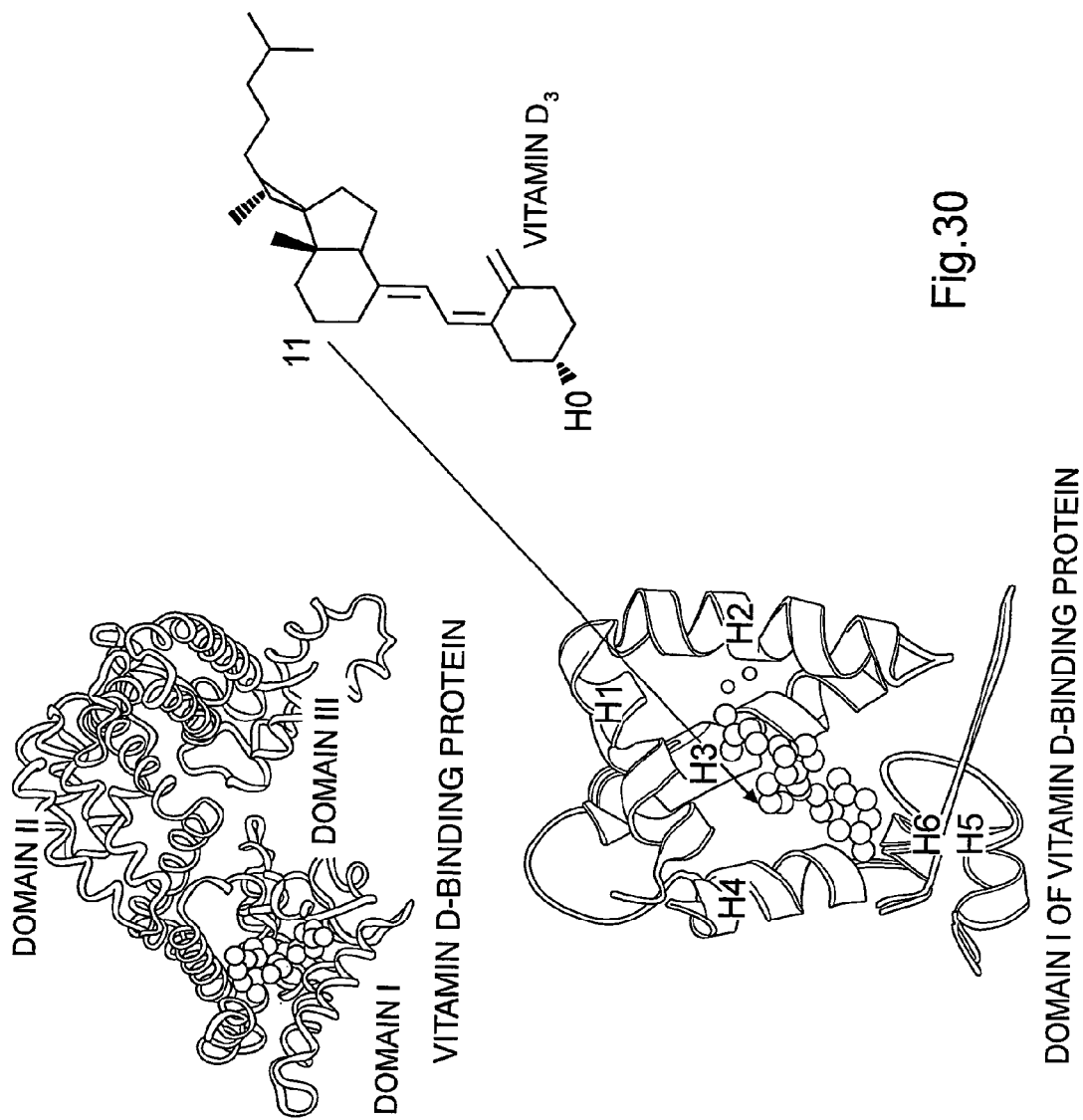

FIG. 30 shows an illustration of design concept. Crystal structure of vitamin D complexed by vitamin D binding protein shows that carbon 11 of vitamin D is exposed. The spacer was therefore covalently linked to carbon 11.

FIG. 31 is an illustration of principles for showing detail from crystal structure of GPRP complexed by D-dimer where N-terminal glycine residue is critical for binding. GPRP is linked to side chain of lysine residue in polypeptide sequence via 6-carbon spacer attached to C-terminal Pro. N-terminal of polypeptide is acetylated and no other lysine residue is present in sequence, ensuring specific reaction of GPRP active ester.

Figure 32:
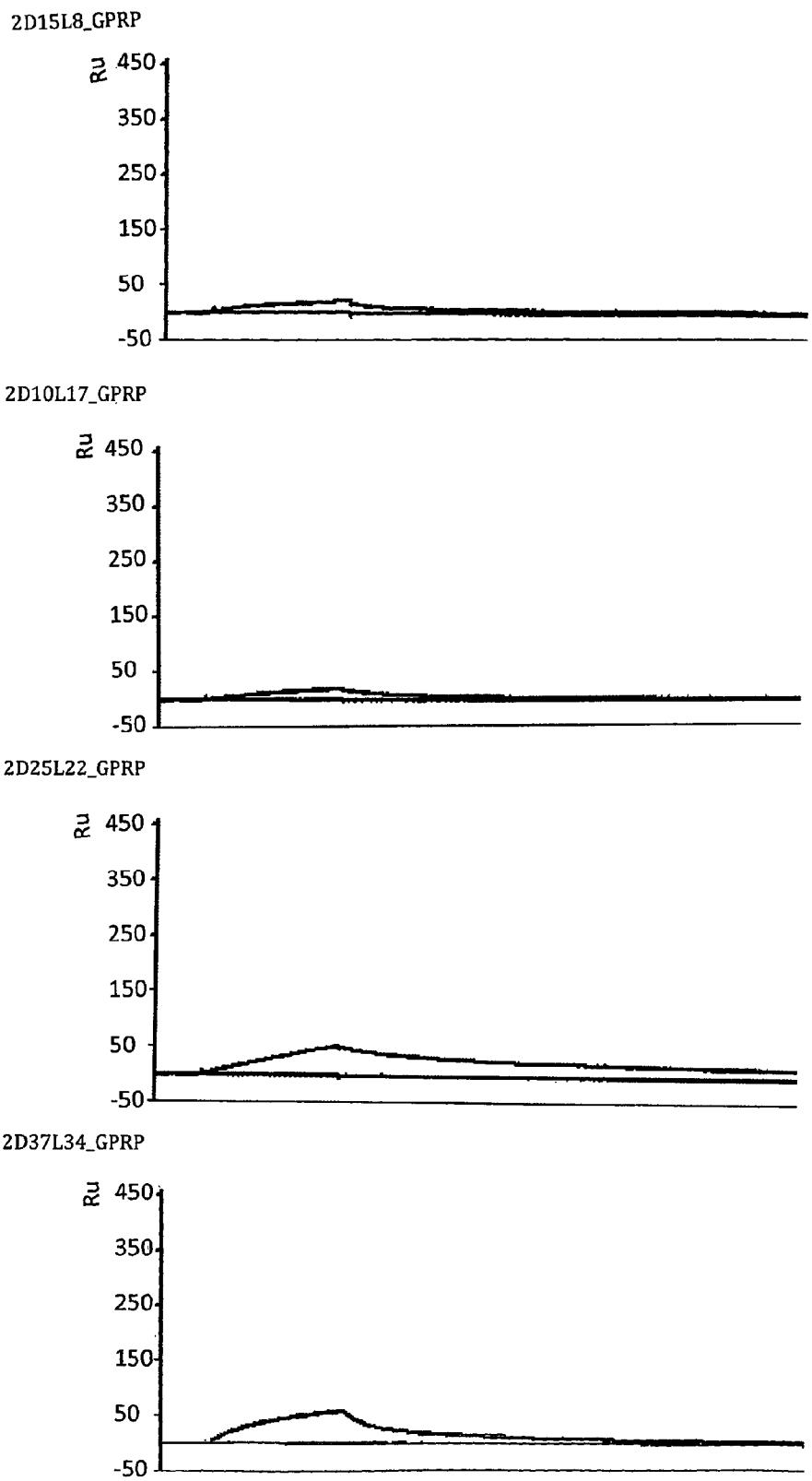

FIG. 32 Panel of sensorgrams obtained from screening binders for the D-dimer using binders at concentrations of only 1 nM, 10 nM and 100 nM. The injection time was 3 minutes and the clearance time was 10 minutes.

Figure 33:
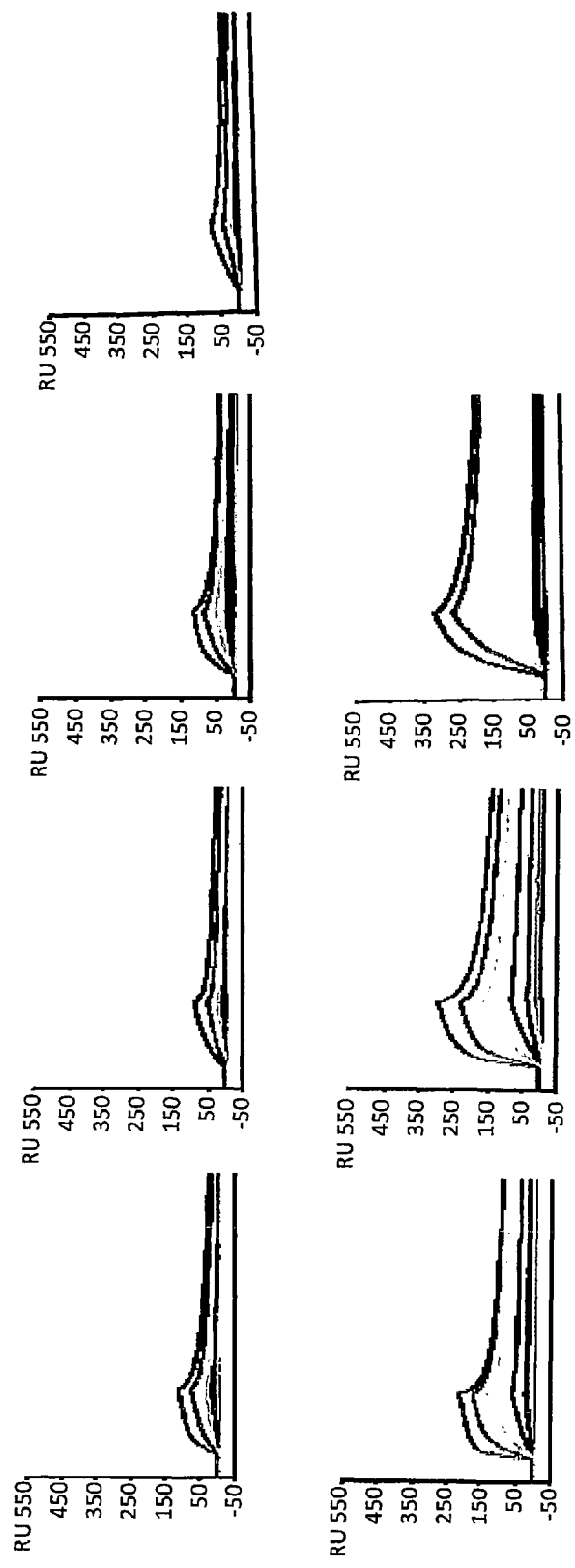
Figure 33:
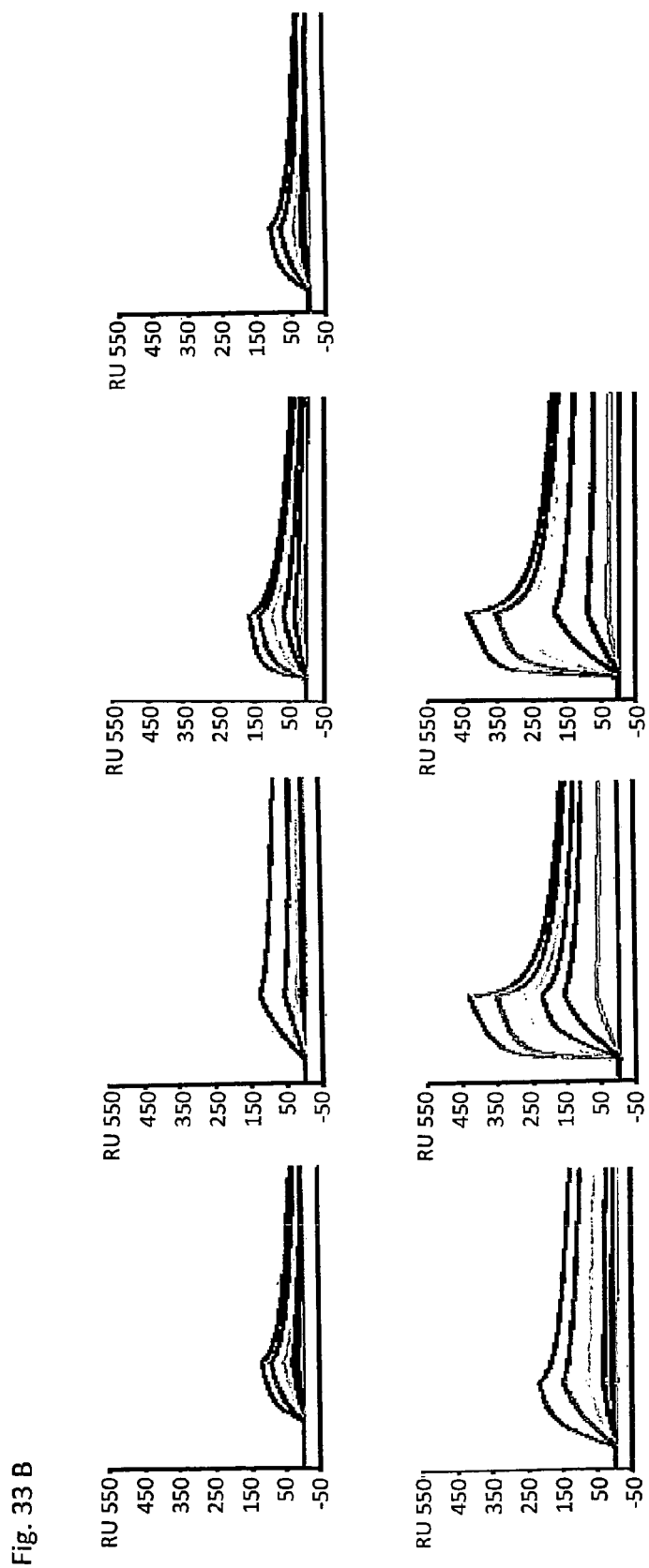

FIG. 33(A and B) Panels of sensorgrams showing binding of seven best binders to immobilized D-dimer in HBS-EP buffer at pH 7.4. Panel A shows seven best monomeric binders. Panel B shows corresponding binders dimerised by bifunctional linker with PEG spacer. Panel A top row from left to right 3-D15L8-GPRP, 3-D10L17-GPRP, 3-D25L22-GPRP, 3-D37L34-GPRP. Panel A bottom row 4-D15L8-GPRP, 4-D10L17-GPRP, 4-D25L22-GPRP. Panel B same binders but dimerised by linker. Scales of axes are identical for direct comparison of uptake between binders. The injection time was 3 minutes and the clearance time was 10 minutes.

Figure 34:
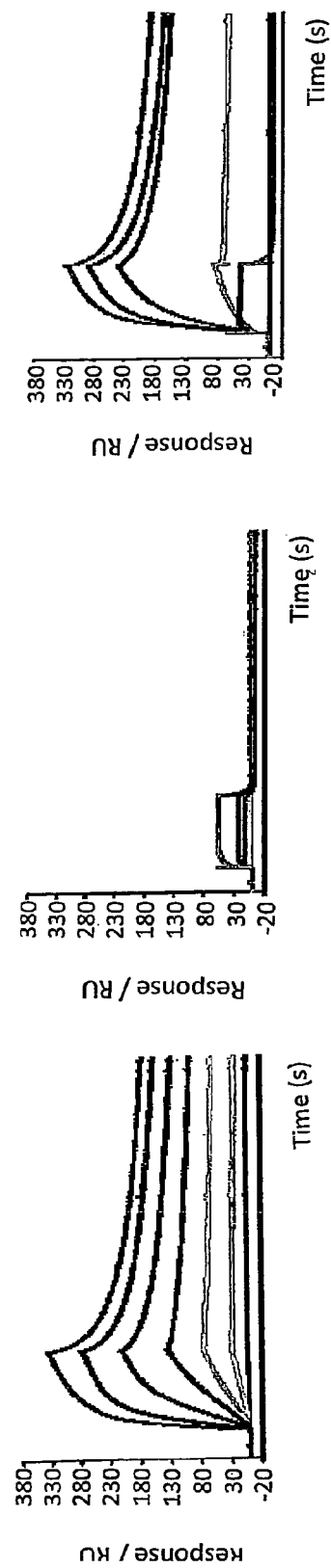

FIG. 34 shows a panel of sensorgrams showing GPRP inhibition of D-dimer binding by 4-D10L17-GPRP. Left sensorgram, binding of immobilized D-dimer by 4-D10L17-GPRP in running buffer at pH 7.4 and 0 nM, 5 nM, 10 nM, 20 nM, 40 nM, 80 nM and 160 nM concentrations of binder. Middle sensorgram, binding of immobilized D-dimer by GPRP in running buffer at pH 7.4 and 0 µM, 1 µM, 10 µM, 100 µM and 1 mM concentrations. Right sensorgram, binding of immobilized D-dimer by 4-D10L17-GPRP in 0 nM, 5 nM, 10 nM, 20 nM, 40 nM, 80 nM and 160 nM concentrations in competition with GPRP in. Scales of axes are identical for direct comparison of uptake between binders. The injection time was 3 minutes and the clearance time was 10 minutes.

Figure 35:
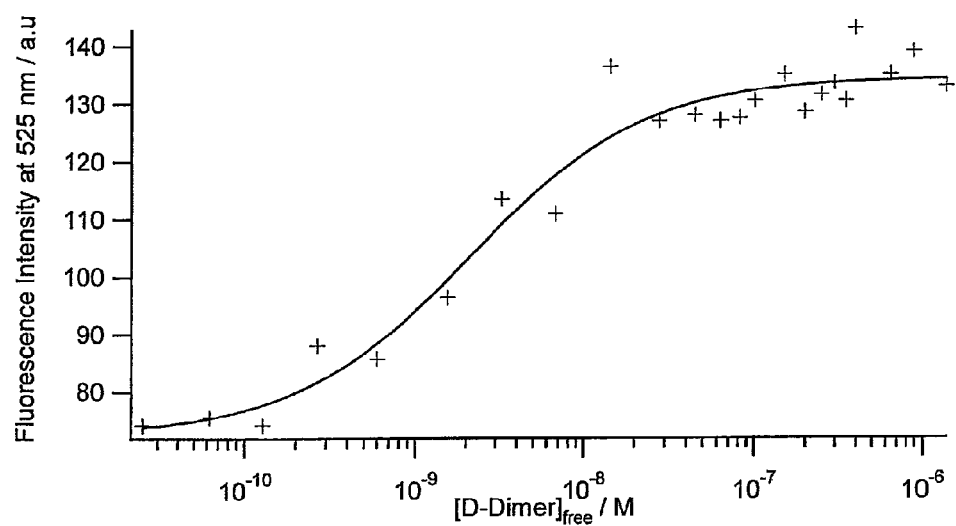

FIG. 35 shows titration curve of 4-C15L8-GPRP with the D-dimer protein in phosphate buffered saline at pH 7.5. The best fit of an equation describing the dissociation of a 1:1 complex to the experimental data give a dissociation constant Kd of 3 nM.

Figure 36:
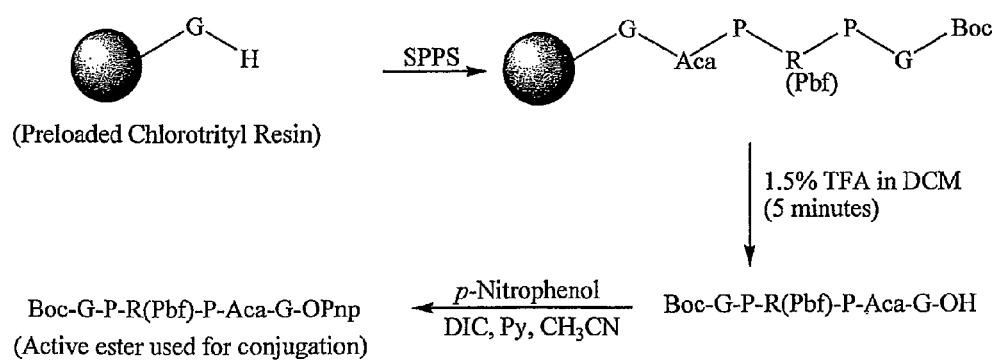

FIG. 36 illustrates the synthesis of the GPRP ligand with a spacer.

DETAILED DESCRIPTION OF THE INVENTION

For the purpose of the present invention, both the IUPAC tree-letter code and the IUPAC one-letter code for amino acids are used and are as follows:

| Amino Acid | 3-Letter Code | 1-Letter Code |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The Polypeptides of the Invention

In some embodiments, the polypeptides of the present invention have the sequences according to any one of SEQ ID NOs. 17-32, optionally having one or both terminals protected by a suitable protecting group.

In some embodiments of the invention, the polypeptides of the present invention have the sequences according to any one of SEQ ID NOs. 1-16.

In one embodiment, the set of polypeptides of the invention is selected from

```
1-C15L8:
                                         (SEQ ID NO: 1)
NEADLEAKIRHLAEKLEARGPEDAEQLAEQLARAFEAFARAG;

2-C15L8:
                                         (SEQ ID NO: 2)
NEADLEAKIRHLAEKLAARGPVDAAQLAEQLARAFEAFARAG;

3-C15L8:
                                         (SEQ ID NO: 3)
NAADLEAKIRHLAEKLAARGPVDAAQLAEQLARRFEAFARAG;

4-C15L8:
                                         (SEQ ID NO: 4)
NAADLEAKIRHLREKLAARGPRDAAQLAEQLARRFERFARAG;

1-C10L17:
                                         (SEQ ID NO: 5)
NAADLEAAIKHLAEALKERGPEDCEQLAEQLARAFEAFARAG;

2-C10L17:
                                         (SEQ ID NO: 6)
NAADLEAAIKHLAEALKARGPVDAAQLAEQLARAFEAFARAG;

3-C10L17:
                                         (SEQ ID NO: 7)
NAADLEARIKHLAERLKARGPVDAAQLAEQLARAFEAFARAG;

4-C10L17:
                                         (SEQ ID NO: 8)
NAADLEARIKHLRERLKARGPRDAAQLAEQLARAFERFARAG;

1-C25L22:
                                         (SEQ ID NO: 9)
NEADLEAAIRHLAEALEARGPKDAKQLAEQLARAFEAFERAG;

2-C25L22:
                                         (SEQ ID NO: 10)
NEADLEAAIRHLAEALAARGPKDAKQLAEQLARAFEAFARAG

3-C25L22:
                                         (SEQ ID NO: 11)
NAADLEAAIRHLAERLAARGPKDAKQLAEQLARAFEAFARAG;

4-C25L22 :
                                         (SEQ ID NO: 12)
NAADLEARIRHLRERLAARGPKDAKQLAEQLARAFERFARAG;

1-C37L34:
                                         (SEQ ID NO: 13)
NEADLEAAIRHLAERLEARGPADAAQLAEQLAAKFEKFARAG;

2-C37L34:
                                         (SEQ ID NO: 14)
NAADLEAAIRHLAERLAARGPVDAAQLAEQLAAKFEKFARAG;

3-C37L34:
                                         (SEQ ID NO: 15)
NAADLEAAIRHLAERLAARGPVDAAQLAEQLARKFEKFARAG;
and 4-C37L34:
                                         (SEQ ID NO: 16)
NAADLEARIRHLRERLAARGPRDAAQLAEQLARKFEKFARAG;
``` or any C-terminal amidation product or N-terminal acylation product of any of these.

Each one of polypeptides of the invention has been designed to fold into two amphiphilic helices connected by a short loop. The amino acids of the polypeptides have been selected based on their propensity for helix or loop formation. Furthermore, residues capable of salt bridge formation, N- and C-terminal capping and stabilization of the helical dipoles have been introduced to stabilise the helical segments. Extensive studies by NMR and CD spectroscopy and by analytical ultracentrifugation have established that a family of closely related polypeptide sequences folds into helix-loop-helix motifs that dimerize to form antiparallel four-helix bundles with molten-globule-like properties. The mean residue ellipticities of the unconjugated sequences in the 16-membered set have been reported previously to be well in the range of similar sequences that form helix-loop-helix dimers. CD and NMR spectroscopic studies have clarified that polypeptide conjugates designed to bind human Carbonic Anhydrase II have properties typical of molten globule like helix-loop-helix dimers. Based on the similarity with several sequences shown previously to form helix-loop-helix dimers with molten globule like properties it is assumed that the polypeptide of the present invention also form similar folds.

The variability of the inventive polypeptides focuses mainly on two variables, charge distribution and site of attachment of ligand. In one embodiment, the polypeptides of the invention have the sequences shown in FIG. 1. In the polypeptides shown in FIG. 1 the total charge of the polypeptides varies from −7 to +2, and the varied residues are all in positions exposed to solvent. The residues for attachment of ligand, e.g. lysine residues (in bold in FIG. 1), are in positions 8, 17, 22 and 34. The polypeptides form a helix-loop-helix secondary structure (helix I-loop-helix II) and the attachment of ligand at the indicated positions allow incorporation in the beginning of helix I, at the end of helix I, in the loop and in the middle of helix II, respectively. Four different total charges for each site of attachment of ligand and four sites of ligand attachment give a total of sixteen sequences.

The bulk of the binding energy in the peptide-protein interaction is expected to arise from hydrophobic interactions between hydrophobic residues on the protein surface and the hydrophobic face of the folded helices whereas charge-charge interactions are expected to provide selectivity.

Some of the amino acids of the polypeptides may be varied i.e. to provide sites for attachment to a solid carrier. For example, an Ala, e.g. in an Ala in position 24 or 25 or in any other of the available sites may be replaced by a Cys, so as to enable attachment by disulfide bond formation to a suitable surface material, e.g. one having reactive disulfide groups that react with free thiol functions, or by attachment e.g. to a gold surface. The Cys also may be used as site of attachment for further functional groups, if desired, e.g. a further reporter group, e.g. by use of maleimide-thiol coupling chemistry, as well-known to the person of ordinary skill in the art.

As noted herein above, N- and C-terminal capping of the polypeptides preferably is used. However, such capping, while being preferable should not be construed as an absolute requirement. N-terminal and C-terminal protection also may be achieved by use of other protecting groups, as well-known to the person of ordinary skill in the art. Thus, examples of N-terminal protecting groups include any acyl group besides the acetyl group, e.g. a C2-C6 alkoxycarbonyl group. Furthermore, the protecting group also may be e.g. an alkoxy carbonyl or aryloxy carbonyl group, e.g. a C2-C6 alkoxycarbonyl group or a phenoxy or benzyloxy carbonyl group. The carboxyl group at the C-terminus besides being protected by amidation, i.e. as a primary, secondary or tertiary amide, also can be protected e.g. by esterification i.e. as an optionally substituted alkyl or aryl ester. Other protective groups and protection methods of any group in the polypeptides of the invention may easily come into the mind of the person of ordinary skill in the art, and may be found in literature, e.g. in "Greene's Protective Groups in Organic Synthesis", by Peter G. M. Wuts and Theodora W. Greene, 4$^{th}$ edition, 2007, ed. John Wiley and Sons, the teachings of which are incorporated herein by reference.

In some embodiments, the polypeptides of the invention also comprise any polypeptide according to SEQ ID NOs. 1-32, e.g. according to SEQ ID NOs 1-16, or SEQ ID NOs 17-32, but containing a Cys instead of an Ala, in particular a Cys in position 24.

In some embodiments, some of the amino acids in the polypeptides of the invention may be derivatized e.g. by reacting with protecting groups or be replaced by amino acids having similar chemical and/or structural properties (i.e. conservative substitution), which may be either naturally occurring or non-naturally occurring amino acids.

For example, in some embodiments it may be necessary to protect amino acids of the polypeptides before derivatizing selected amide-bond forming residues with ligand and/or reporter group, respectively.

As is well-known, naturally occurring amino acids may be classified into different groups based on the chemical and/or structural properties of their side chain, i.e. the aliphatic amino acids Gly, Ala, Val, Leu, and Ile; the amino acids with hydroxyl or sulfur-containing side chains Ser, Cys, Thr, and Met; the aromatic amino acids Phe, Tyr, Thr and His (though His may also be classified as a basic amino acid); the basic amino acids Lys and Arg (and His) and the acidic amino acids and their amides Glu, Asp, Gln and Asn. Thus, in some embodiments, any amino acid of the polypeptides according to any one of the SEQ ID NOs. 1-32 may be replaced by conservative substitution, i.e. by replacing it with an amino acid that has similar chemical and/or structural properties, e.g. belonging to the same group as outlined herein above.

Furthermore, there exist a multitude of non-naturally occurring amino acids that may be classified into the abovementioned groups, and many of such amino acids are commercially available. For example, alanine (2-aminopropanoic acid) may be replaced by 2-methylalanine (2-amino-2-methylpropanoic acid); leucine (2-amino-4-methylpentanoic acid) may be replaced by norleucine (2-aminohexanoic acid) or by tert-leucine (2-amino-3,3-dimethylbutyric acid) etc.

In some embodiments, the leucine in positions 5, 16 and 27, respectively, in the 3- and 4-series is replaced by norleucine.

When replacing one or more amino acids of the polypeptides with other amino acids (natural or non-natural), the total net charge of the polypeptide preferably is retained. In some embodiments, though, the total net charged also may allowed to vary.

The amino acid serving as attachment for ligand (i.e. position 8, 17, 22 and 34, respectively) and for reporter group (i.e. amino acid in position 10, 15, 25 and 37, respectively), should be selected so as to be able to form an amide bond with ligand and reporter group, respectively. As such, said amino acids preferably should comprise a pendant group (the residue not involved in forming the polypeptide chain, or "amino acid residue") having a primary amine functionality. The amino acid may be natural or non-natural.

In order for the amino acid serving as attachment site to be able to form an amide bond with the ligand or reporter group, respectively, the reporter or ligand group preferably should be derivatized by forming an active ester thereof, as will be discussed herein below.

Having regard to the above, in a polypeptide according to any one of the SEQ ID NOs. 1-16, it is contemplated that any lysine may be replaced by any suitable homologue or derivative, provided, if the lysine is serving as a ligand or reporter attachment site, that the ability of forming a bond with an active ester of the ligand or reporter is retained. For example, lysine (2,6-diaminohexanoic acid) may be replaced by ornithine (2,5-diaminopentanoic acid), or by 2,4-diaminobutyric acid or by any other carbon chain homologue of these, e.g. having a branched chain.

Furthermore, in some embodiments, any amino acid of the polypeptides according to any one of the SEQ ID NOs. 1-32 may be replaced by any modified amino acid having similar chemical and/or structural properties.

In some embodiments, the polypeptides of the invention may comprise amino acids that have been modified by incorporation of protecting groups, as well-known to the person of ordinary skill in the art, cf. also. "Greene's Protective Groups in Organic Synthesis" supra. For example, at the time of conjugation of active ester of ligand protective groups suitably are used so that only the lysine to which the ligand is to be attached is accessible.

The amide-bond forming amino acids in positions 8, 10, 15, 17, 22, 25, 34 and 37 preferably are lysines. However, in some embodiments, any one of the positions 8, 10, 15, 17, 22, 25, 34 and 37, to which ligands and reporter groups respectively are attached, may be occupied by any equivalent amino acid or amino acid analogue or modified amino acid, provided that this amino acid or amino acid analogue enables attachment of the selected ligand and reporter group. Thus, for example, the amide forming amino acid may equally well be ornithine or 2,4-diamino butyric acid or any carbon chain homologue of these, e.g. having a branched chain.

In some embodiments, when referring to a polypeptide according to any one of the SEQ ID NOs 1-32, this also includes any of the variants of these as obtained by the any of the above-mentioned substitutions or modifications.

In some embodiments, the polypeptide of the invention is in the form of a dimer. In this case, the dimer may comprises two of the polypeptides according to any one of the SEQ ID NOs 1-32, e.g. two polypeptides according to any one of the SEQ ID NOs 1-16, or any variant of these as discussed herein above. The polypeptides of the dimer may be bonded to each other either via non-covalent bonds, such as may form spontaneously in a solution of the polypeptides of the invention, or may be covalently bonded to each other e.g. by one or several disulfide bonds.

The Molecular Tool

As mentioned herein above, according to one aspect a molecular tool is provided, comprising a plurality of the polypeptides defined herein above. For example, a set of polypeptides of the invention may comprise 16 helix-loop-helix polypeptides as defined herein above, e.g. sixteen 42-amino acids polypeptides having amino acids permitting to attach ligand in positions 8, 17, 22 or 34, and reporter groups in positions 10, 15, 25 and 37, respectively and having total charges generally varying from negative, e.g. −7, to positive, e.g. +2. Examples of such polypeptides are provided in the Sequence Listing, but the skilled person will be well capable of preparing modified variants of these polypeptides, e.g. by conservative substitutions of one or several of the amino acids of these polypeptides, or by chemical modifications of the amino acids of the polypeptides. Furthermore, it should be realized that subsets of the 16 polypeptides according to the invention may be used, or even larger sets, e.g. sets comprising additional polypeptides. All these variants are considered to be within the scope of the present invention.

In one embodiment, the molecular tool comprises a set of polypeptides having sequences according to SEQ ID NOs 1-32.

In one embodiment, the molecular tool comprises a set of polypeptides having sequences according to SEQ ID NOs 1-16.

In some embodiments, the molecular tool comprises a set of polypeptides having sequences according to SEQ ID NOs 17-32.

In other embodiments, the molecular tool comprises a set of set of polypeptides having sequences according to FIG. 1.

In some other embodiments, the molecular tool comprises a set of polypeptides selected from SEQ ID NOs 1-32, but wherein leucine in position 5, 16 and 27, respectively, of the 3- and 4-series have been replaced by norleucine (one-letter code: J).

In still other embodiments, the molecular tool comprises a set of polypeptides selected from SEQ ID NOs 1-16, but wherein leucine in position 5, 16 and 27, respectively, of the 3- and 4-series have been replaced by norleucine (one-letter code: J).

In still other embodiments, the molecular tool comprises a set of polypeptides selected from SEQ ID NOs 1-32, wherein either one or both polypeptide terminals carry protecting groups.

Thus, according to one embodiment, the molecular tool comprises a set of polypeptides

```
1-C15L8:
                                        (SEQ ID NO: 1)
NEADLEAKIRHLAEKLEARGPEDAEQLAEQLARAFEAFARAG;

2-C15L8:
                                        (SEQ ID NO: 2)
NEADLEAKIRHLAEKLAARGPVDAAQLAEQLARAFEAFARAG;

3-C15L8:
                                        (SEQ ID NO: 3)
NAADLEAKIRHLAEKLAARGPVDAAQLAEQLARRFEAFARAG;

4-C15L8:
                                        (SEQ ID NO: 4)
NAADLEAKIRHLREKLAARGPRDAAQLAEQLARRFERFARAG;

1-C10L17:
                                        (SEQ ID NO: 5)
NAADLEAAIKHLAEALKERGPEDCEQLAEQLARAFEAFARAG;

2-C10L17:
                                        (SEQ ID NO: 6)
NAADLEAAIKHLAEALKARGPVDAAQLAEQLARAFEAFARAG;

3-C10L17:
                                        (SEQ ID NO: 7)
NAADLEARIKHLAERLKARGPVDAAQLAEQLARAFEAFARAG;

4-C10L17:
                                        (SEQ ID NO: 8)
NAADLEARIKHLRERLKARGPRDAAQLAEQLARAFERFARAG;

1-C25L22:
                                        (SEQ ID NO: 9)
NEADLEAAIRHLAEALEARGPKDAKQLAEQLARAFEAFERAG;

2-C25L22:
                                        (SEQ ID NO: 10)
NEADLEAAIRHLAEALAARGPKDAKQLAEQLARAFEAFARAG

3-C25L22:
                                        (SEQ ID NO: 11)
NAADLEAAIRHLAERLAARGPKDAKQLAEQLARAFEAFARAG;

4-C25L22:
                                        (SEQ ID NO: 12)
NAADLEARIRHLRERLAARGPKDAKQLAEQLARAFERFARAG;

1-C37L34:
                                        (SEQ ID NO: 13)
NEADLEAAIRHLAERLEARGPADAAQLAEQLAAKFEKFARAG;

2-C37L34:
                                        (SEQ ID NO: 14)
NAADLEAAIRHLAERLAARGPVDAAQLAEQLAAKFEKFARAG;

3-C37L34:
                                        (SEQ ID NO: 15)
NAADLEAAIRHLAERLAARGPVDAAQLAEQLARKFEKFARAG;
and 4-C37L34:
                                        (SEQ ID NO: 16)
NAADLEARIRHLRERLAARGPRDAAQLAEQLARKFEKFARAG;
``` or any C-terminal amidation product or N-terminal acylation product of any of these.

The set of polypeptides preferably comprises 2-16 different polypeptides, e.g. 2, 3, 4, 5, 6, 7, 8, 9, 10, 11, 12, 13, 14, 15, or 16 different polypeptides. For example, the set comprises polypeptides having sequences of at least 2 different SEQ ID NOs selected from any one of the SEQ ID NOs 1-32, e.g. 1-16.

For example, a suitable set may comprise polypeptides of at least 3 different SEQ ID NOs, or at least 4 different SEQ ID NOs, e.g. at least 5 different SEQ ID NOs, at least 6 different SEQ ID NOs, at least 7 different SEQ ID NOs, at least 8 different SEQ ID NOs, at least 9 different SEQ ID NOs, at least 10 different SEQ ID NOs, at least 11 different SEQ ID NOs, at least 12 different SEQ ID NOs, at least 13 different SEQ ID NOs, at least 14 different SEQ ID NOs, or at least 15 different SEQ ID NOs. In some preferable embodiments, the set comprises polypeptides according to 16 SEQ ID NOs, e.g. SEQ ID NOs 1-16 or SEQ ID NOs 17-32.

It is preferable to use a tool comprising at least 16 polypeptides (having 4 different sites of ligand incorporation and 4 different charges for each site of ligand incorporation). The reason is that it is very hard, not to say impossible, to predict which polypeptide that, in combination with a given ligand, will give rise to the optimum binding affinity and selectivity. Consequently, using as a molecular tool a set of polypeptides based on all 16 sequences of the Sequence Listing, is likely to give the best result. However, it also is contemplated as possible to use a subset of polypeptides based on only some of the sequences, or even to include further polypeptides, e.g. obtained by varying the amino acids by conservative substitution.

In some embodiments, the set comprises polypeptides all having the same electric charge in the amino acid sequence (cf. FIG. 1), while in others, the set comprises polypeptides some of which have different charges. In still other embodiments, the set comprises polypeptides which all have different charges, e.g. polypeptides of different charge but same ligand attachment position in the amino acid sequence.

The small molecule ligand is attached at the side chains of lysine residues in positions 8, 17, 22 and 34. The underlying design principle is that for optimum selectivity and affinity the small molecule and the polypeptide must contribute cooperatively to binding. The ligand may be attached to the polypeptide via a spacer, the function of which is to allow the polypeptide scaffold to find a shape and charge complementary binding site in close proximity to the binding site of the small molecule warhead. Thus, the selection of spacer generally is an important aspect of binder development.

Examples of spacers that may be used are given in the Examples in relation to specific ligands, but these spacers may be used also with other ligands. Other spacer molecules that may be used will easily come to the mind of the person skilled in the art. For example, the spacer may be an aliphatic chain of 1-12 carbon atoms, which may optionally be substituted with hydrophilic groups to enhance solubility. In some cases, the spacer may have to be even longer than 12 carbon atoms, in which case this may give rise solubility problems. To mitigate such problems, one or several polar groups may be introduced into the backbone of the spacer or substituted onto the spacer backbone.

The ligand (optionally including a spacer), as well as the reporter group, may be attached to the polypeptide by bringing the polypeptide into contact with an active ester of the ligand (optionally including a spacer) and reporter, respectively. An active ester derivative of a ligand L (or reporter R) has the general formula (I)

Q-COOR$^1$         (I)

wherein Q is ligand L or reporter R and R$^1$ is a leaving group with a pe$_a$ of about 6-8, e.g. nitrophenyl.

In case the ligand L is attached to the polypeptide through a spacer, the active ester derivate may be represented by formula (I')

L-X—COOR$^1$         (I')

wherein X represents the spacer. For example, in case X is an aliphatic chain of 1-12 carbon atoms, the active ester derivative may represented by formula (I')

L-(CH$_2$)$_n$—COOR$^1$         (I')

wherein n is an integer of from 1 to 12.

An example of synthesis of active esters wherein n is 4, 6 or 11 and R$^1$ is p-nitro-phenyl has been described in WO 07/117, 215, the contents of which is incorporated herein in its entirety.

The reporter group is attached at the side chains of amide forming residues, e.g. lysine residues, in positions 10, 15, 25 and 37 and generally is a group that, when attached to the polypeptide or the polypeptide conjugate, is capable of giving rise to a detectable signal indicative of a binding interaction between the target molecule and the polypeptide or the polypeptide conjugate, respectively. Preferred examples of reporter groups are fluorescent probes such as dansyl, coumarin, fluorescein, rhodamine and Oregon Green derivatives. The reporter group may also be an enzyme such as phosphoenolpyruvate kinase. The reporter group may be attached to the amide forming residue according to the supplier's instructions or by other conventional methods, e.g. as an active ester derivative The 42-amino acids polypeptides thus may be classified as follows:

| Polypeptide name | Ligand attachment site | Reporter attachment site |
|---|---|---|
| C10L17 | 17 | 10 |
| C15L8 | 8 | 15 |
| C25L22 | 22 | 25 |
| C37L34 | 34 | 37 |

According to one aspect of the invention, there is provided a method of screening for a ligand-polypeptide conjugate capable of binding a target molecule, comprising providing at least one conjugate molecule comprising a polypeptide having a sequence selected from SEQ ID NOs 1-32, said polypeptide having a ligand for the target molecule attached by an amide bond to an amino acid capable of forming an amide bond with the ligand, said amino acid being at a position in the polypeptide sequence selected from positions 8, 17, 22, and 34, and said polypeptide having a reporter group attached by an amide bond to an amino acid capable of forming an amide bond with the reporter group, said amino acid being at a position in the polypeptide sequence selected from positions 15, 10, 25 and 37;

bringing the target molecule in contact with the conjugate molecule; and detecting a signal from the reporter group.

The polypeptides for use in the inventive method are as described herein above. For example, the amino acid capable of forming an amide bond with ligand or reporter group preferably comprises a primary amine functionality (i.e. —NH$_2$) and in some embodiments, said amino acid is selected from lysine, ornithine or 2,4-diaminobutyric acid.

Thus, in one embodiment, the screening method comprises providing at least one conjugate molecule comprising a polypeptide having a sequence selected from SEQ ID NOs 1-16, said polypeptide having a ligand for the target molecule attached to a lysine at a position selected from positions 8, 17, 22, and 34, and said polypeptide having a reporter group attached to a lysine at a position selected from positions 15, 10, 25 and 37;

bringing the target molecule in contact with the conjugate molecule; and detecting a signal from the reporter group.

One embodiment of the invention comprises providing a set of conjugate molecules obtained by attaching a ligand for a target molecule and a reporter for detecting binding to the target molecule to each one of the polypeptides of a set of polypeptides according to the invention so as to obtain the corresponding set of ligand-reporter-polypeptide conjugates, bringing the target molecule into contact with each one of the ligand-reporter-polypeptide conjugates, and detecting a signal from the reporter group.

According to a further aspect, the invention relates to the product obtained by screening for a ligand-polypeptide conjugate capable of binding a target molecule with enhanced affinity and selectivity, compared to the ligand when not attached to the polypeptide. This product e.g. may be the ligand-polypeptide conjugate, or the ligand-polypeptide conjugate additionally comprising one or more other groups, e.g. a reporter group, a group allowing the polypeptide to be attached to a solid carrier, etc. Several examples of ligand-polypeptide conjugate as products obtained by the screening method of the invention are provided herein below and these products, as well as possible variants thereof, e.g. obtained by conservative substitution of amino acids of the polypeptides of the conjugates, are all within the scope of the present invention.

The ligand-polypeptide according to the invention will have numerous applications in the biotechnological and pharmaceutical field. According to one aspect, the use of a ligand-polypeptide according to the invention in therapy is provided. For example, according to one aspect the invention provides a ligand-polypeptide conjugate according to the invention for use in a method of diagnosis. According to another aspect, the invention provides a ligand-polypeptide conjugate according to the invention for use in an in vivo-imaging method.

Some examples of ligand-polypeptide conjugates of the invention are provided herein below, but the skilled person will realize that due to the versatility of the molecular tool of the invention, the field of application is extremely broad and it will be possible to develop high-affinity, high-selectivity binders for numerous proteins of medical interest, e.g. various enzymes and receptors known or suspected to be involved in pathological conditions.

The ligand-polypeptide conjugates provided by the invention are not only limited to those that may be of use in therapy. Rather, the ligand-polypeptide conjugates of the invention may be useful in any number of biotechnological applications, such as in forensic methods or in protein purification, e.g. large-scale (industrial scale) protein purification.

EXAMPLES

Example 1

In Example 1, human Acetylcholine esterase, hAChE, was used as the target molecule.

The hAChE hydrolyses acetylcholine to form choline in a reaction that is crucial for the transmission of nerve signals and therefore a target in chemical warfare. Nerve gases such as Sarin, Soman and VX act by inhibiting hAChE and reducing the activity to an extent where the exposed person is severely injured or killed (Evison, D., Hinsley, D. and P. Rice. British Medical Journal. 2002, 324, 332-335. Marrs, T. Pharmacy. Ther. 1993, 58, 51-66). Furthermore, hAChE is an important drug target as the loss of acetylcholine plays a role in Alzheimer's disease (Talesa, V. N. Mechanisms of Ageing and Development 2001, 122, 1961-1969. Perry, E. K.; Tomlinson, B. E.; Blessed, G.; Bergmann, K.; Gibson, P. H.; Perry, R. H. British Medical Journal, 1978, 2, 1457-1459. Perry, E. K.; Perry, R. H.; Blessed, G.; Tomlinson, B. E. Neuropathology and Applied Neurobiology 1978, 4, 273-277), and the inhibition of hAChE reduces the symptoms (Polinsky R. J. Clin. Ther. 1998, 20, 4, 634-647). Selective high-affinity binders for hAChE are therefore of considerable interest in a number of biomedical applications.

Results and Discussion
Design and Synthesis.

The use of active site inhibitors in binder design is attractive as small organic molecules with moderate affinity and good selectivity for target enzymes are often available, especially for established and validated proteins. In the case of hAChE there are several reported inhibitors in the literature (Mooser, G.; Sigman, D. S. Biochemistry 1974, 13, 2299-2307; Taylor, P.; Lappi, S. Biochemistry, 1975, 14, 1989-1997; Nolte, H.-J.; Rosenberry, T. L.; Neumann, E. Biochemistry, 1980, 19, 3705-3711) and 9-aminoacridine, a known inhibitor with a reported affinity in the range of 30-100 nM (Steinberg, G. M.; Mednick, M. L.; Maddox, J.; Rice, R.: Cramer, J. J Med Chem 1975, 18, 1056-1061. Radic, Z., Taylor, P. Biol. Chem. 2001, 276, 4622-4633, 2001) was selected. A binder for hAChE based on an active site inhibitor, however, presents special problems as the active site of hAChE is located in a 20 Å deep cavity (Sussman, J. L.; Harel, M.; Frolow, F.; Oefner, C.; Goldman, A.; Toker, L.; Silman, I. Science 1991, 253, 872-9. Shafferman A.; Kronman C.; Flashner Y.; Leitner; Grosfeld H.; Ordentlich A.; Gazes H.; Cohen S.; Ariel N.; Barak D.; Hare M.; Silman I.; Sussman J. L.; Vela B. J. Biol. Chem. 1992, 267, 17640-17648). The conjugation of an inhibitor for hAChE to a polypeptide scaffold thus requires a spacer of comparable length to enable simultaneous binding of the active site inhibitor and the polypeptide to their unique binding epitopes. The design of the polypeptide conjugate therefore included selecting a suitable spacer and a suitable site of attachment of the spacer to the ligand. An aliphatic spacer would be expected to bind well in the cavity that leads to the active site due to hydrophobic interactions, but the hydrophobicity of a 20 Å aliphatic chain also raises concerns about solubility. Also, the entropic advantage of combining the scaffold and the inhibitor may not be as large as for a shorter spacer.

A set of 16 polypeptide sequences of the invention (FIG. 1) was used. The total charge of each polypeptide varied in four steps between −7 to +2 and the varied residues were all in positions exposed to solvent. The lysine residues used for attachment of ligands were in positions 8, 17, 22 and 34, to allow incorporation in the beginning of helix I, at the end of helix I, in the loop and in the middle of helix II, respectively.

Each polypeptide was decorated with a reporter group, viz. a coumarin probe, by conjugating 7 methoxycoumarin-3-carboxylic acid to the side chain of a selectively deprotected lysine residue, i.e. the lysine residue in position 10, 15, 25 and 37, respectively. The fluorophor enabled measurement of binding to the target molecule, as the fluorescence intensity was affected by the change in molecular environment upon binding to the protein.

The 9-aminoacridine ligand is a well studied active site inhibitor (Shafferman A.; Kronman C.; Flashner Y.; Leitner; Grosfeld H.; Ordentlich A.; Gazes H; Cohen S.; Ariel N.; Barak D.; Hare M.; Silman I.; Sussman J. L.; Vela B. J. Biol. Chem. 1992, 267, 17640-17648. Olofsson, S.; Johansson, G.; Baltzer, L. J. Chem. Soc., Perkin Trans. 2 1995, 2047-56. Olofsson, S.; Baltzer, L. Fold. Des. 1996, 1, 347-356. Andersson, L.; Stenhagen, G.; Baltzer, L. J. Org. Chem. 1998, 63, 1366-1367. Broo, K. S.; Brive, L.; Ahlberg, P.; Baltzer, L. J. Am. Chem. Soc. 1997, 119, 11362-11372). Inspection of the crystal structure of hAChE revealed that the active site is buried deep in the protein in a 20 Å deep pocket (Dupre, D. J.; Robinson, F. A. J. Chem. Soc. 1945, 549-51). Consequently, the spacer would have to be able to accommodate a polypeptide that could bind an epitope on the protein surface and an acridine residue that could bind in the active site, at a distance of 20 Å from each other. Such a spacer would preferably be aliphatic, if only target affinity was taken into consideration. However, an aliphatic spacer of more than fifteen methylene groups is hydrophobic to a level where it causes solubility problems, in synthesis as well as in polypeptide conjugation, and an alternative way of constructing such a long spacer with improved solubility properties would be to prepare it in two segments with a polar group in the middle.

A high-resolution structure of a complex between a polypeptide conjugate binder and a protein is not yet available, and the exact interactions that control binding can only be guessed at. Although, intuitively the inhibitor would be expected to bind in the active site, an assumption that has been verified in the cases of human Carbonic Anhydrase II (Perry, E. K.; Tomlinson, B. E.; Blessed, G.; Bergmann, K.; Gibson, P. H.; Perry, R. H. British Medical Journal, 1978, 2, 1457-1459) and the C-reactive protein (Talesa, V. N. Mechanisms of Ageing and Development 2001, 122, 1961-1969), the interactions between the polypeptide and the protein remain hypothetical. The conjugate binds tightly only if the spacer is compatible with simultaneous binding of polypeptide and warhead without forcing the spacer into high-energy conformations or dislocating the warhead in the active site. Due to the difficulty of predicting accurately the binding epitope for the polypeptide scaffold the spacer strategy would have to allow for some flexibility in size. Spacers for conjugation to the polypeptides were prepared by synthesizing all four combinations of 6-aminohexanoic acid and 8-aminooctanoic acid (Scheme 1).

In addition to providing three different spacer lengths, two different positions of the intermediary amide group of the spacer were also obtained. Although it was expected that the shortest spacer would give the highest selectivity all four spacers were synthesized as it was impossible to predict the optimal spacer length from the crystal structure of hAChE and because they could be of interest in future applications. In order to facilitate rapid and site-specific conjugation of the ligands to the polypeptides the sequences consist of only one free lysine residue and the ligands were prepared as activated esters.

The ligand-spacer combinations 9, 10, 11 and 12 were synthesized as shown in Scheme 1.

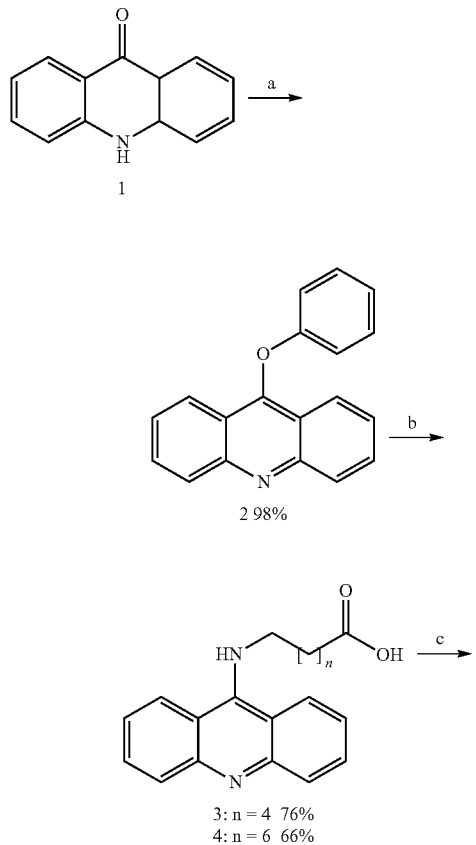

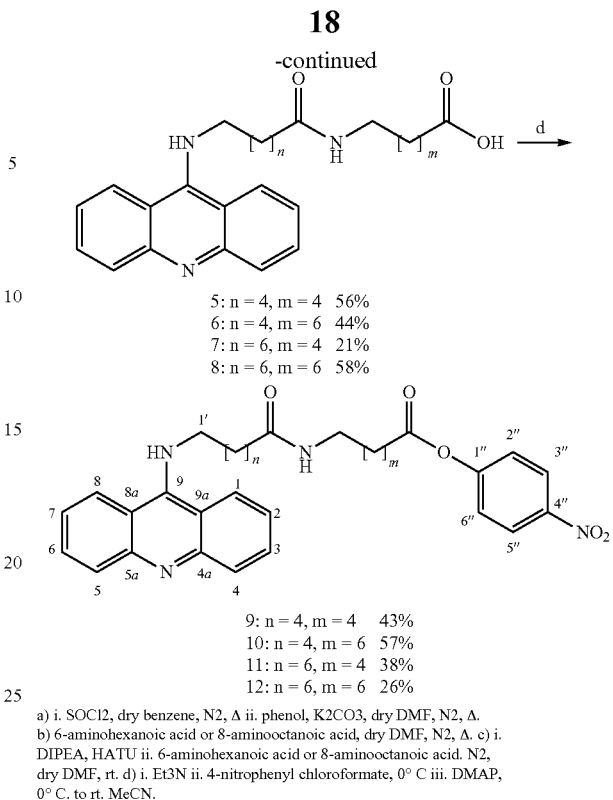

a) i. SOCl2, dry benzene, N2, Δ ii. phenol, K2CO3, dry DMF, N2, Δ.
b) 6-aminohexanoic acid or 8-aminooctanoic acid, dry DMF, N2, Δ. c) i. DIPEA, HATU ii. 6-aminohexanoic acid or 8-aminooctanoic acid. N2, dry DMF, rt. d) i. Et3N ii. 4-nitrophenyl chloroformate, 0° C iii. DMAP, 0° C. to rt. MeCN.

With reference to Scheme 1,9-Phenoxyacridine (2) was synthesized as reported in the literature (Dupre, D. J.; Robinson, F. A. J. Chem. Soc. 1945, 549-51. Ghaneolhosseini, H.; Tjarks, W.; Sjöberg, S. Tetrahedron 1998, 54, 3877-3884) by forming 9-chloroacridine in situ, followed by an aromatic nucleophilic substitution with phenol. 9-Phenoxyacridine (2) was reacted with 6-aminohexanoic acid or 8-aminooctanoic acid to form 3 or 4, respectively. HATU was the most effective coupling reagent between 6-aminohexanoic acid or 8-aminooctanoic acid to the carboxylic acid functionality in 3 or 4 to give compounds 5, 6, 7 and 8. The carboxylic acids were preactivated by stirring the corresponding acid with HATU and DIPEA for approximately 1 h. 1.1-1.5 equiv. HATU was the best compromise to minimize unreacted starting material and the coupling of a second amine. The acids 5, 6, 7 and 8 were activated as their p-nitrophenol esters using a literature method used for other carboxylic acids (Gagnon, P.; Huang, X.; Therrien, E.; Keillor, J. W. Tetrahedron Lett. 2002, 43, 7717-7719). In order to minimize ester hydrolysis the product containing fractions were directly frozen in N$_2$(l) after the HPLC purification and the solvent was subsequently removed by lyophilization.

Thus, the following ligand-spacer moieties were attached to the lysines of the polypeptides:

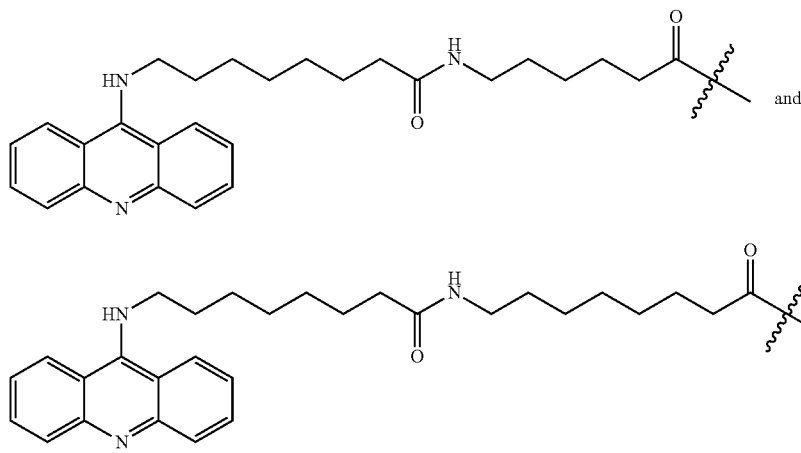

The Identification and Affinity of Polypeptide Conjugate Binders for hAChE.

The active ester 9 was coupled to each member of the set of sixteen polypeptides according to the invention, and the affinity of each one for hAChE was estimated in a screening procedure. Each polypeptide binder candidate was dissolved in 50 mM sodium phosphate buffer at pH 7.0 and dispensed into 9 wells of a microtiter plate to give final concentrations of 500 nM after the addition of protein. Aliquots of hAChE from a stock solution were added to three wells to give final protein concentrations of 500 nM, and to three more wells to give final protein concentrations of 1000 nM. In short, each binder was titrated in three steps, and each measurement was carried out in triplicate. The binders for which the addition of one equivalent of protein gave rise to a significant difference in intensity in comparison to that of the binder without protein, and the intensity in the presence of a second equivalent of protein did not give rise to any further change in intensity, were assumed to be more than 90% complexed after the first addition of protein. Under that assumption a dissociation constant, $K_d$, of 10 nM or less can be estimated, and a binder that fulfilled these criteria was considered a "hit". The polypeptide 4-C10L17-Ac (4-C10L17 acylated at the C-terminal) was chosen for further evaluation of selectivity in this screening procedure and the conjugation of the polypeptide to 9-aminoacridine was shown to have given rise to a binder with an affinity that was higher than that of the small molecule. The fluorescence intensities were measured at 298K using a microtitre plate reader with excitation at 350 nm and emission at 420 nm.

The selectivity of 4-C10L17-Ac was determined by monitoring the capturing of hAChE from cerebrospinal fluid (CSF) obtained from Uppsala University hospital. CSF represents a complex biological milieu with several other proteins in high concentration and one of considerable interest with regards to future applications. The selected binder was resynthesized with an acetamidomethyl-(Acm-) protected Cys residue in position 24, instead of an Ala in this position, and attached to polystyrene nanoparticles coated with Pluronic® F108-PDS by disulfide bond formation after Acm deprotection. The coating material forms monolayers of PEG equipped with activated disulfide groups that spontaneously react with free thiols under the release of 2-mercaptopyridine. The functionalized nanoparticles were incubated in CSF for 1 hour and centrifuged after which the supernatant was removed. The particles were washed three times by incubation in buffer followed by centrifugation and removal of the supernatant. After the washing steps the particles were analyzed by ELISA and gel electrophoresis. For the SDS-PAGE analysis the binder was cleaved from the particles using dithiothreitol and separated from the particles by centrifugation. The supernatant was applied to the electrophoresis gel. Unfortunately the band from hAChE could not be separated from that of human serum albumin (HSA) which is present in high concentration and is adsorbed non-specifically to the polystyrene beads (FIG. 2). HSA adsorption is demonstrated by SDS-PAGE in a control experiment where the non-functionalized beads were incubated with the same patient CSF as described for the binder conjugates and treated in an identical manner.

The capture of hAChE by 4-C10L17-Ac was also analyzed by a nanoparticle ELISA based on luminescence. In the ELISA experiments aliquots of the washed particles were incubated with a polyclonal antibody directed against hAChE, which had been pre-conjugated to horse radish peroxidase. After three washing steps the substrate luminol was added and the resulting luminescent signal recorded. As a reference, particles without binder were incubated in CSF from the same patient and treated identically as the particles with binder. Particles conjugated to binders captured hAChE according to the sandwich ELISA and it was demonstrated that 4-C10L17-Ac could selectively extract hAChE from CSF, in competition with all proteins found in CSF, (FIG. 2). A signal was also obtained from the supernatant from the reference particles, although much weaker than that of the functionalized beads. The background signal may be due to the high level of antibody conjugate used that can be difficult to remove completely. The results show that hAChE was selectively extracted from CSF collected from a patient, and that the binder 4-C10L17-Ac has a high affinity and selectivity in a measurement situation where there is considerable competition from high-concentration proteins such as HSA and all other proteins in CSF.

Conclusion.

The conjugation of 9-aminoacridine to each member of a set of polypeptide scaffolds has made it possible to obtain a binder, 4-C10L17-Ac, with high affinity and selectivity for hAChE. The properties are comparable to those of antibodies although the size is only 1/30 of that of IgY. The results show that it is possible to use small molecule inhibitors for enzymes with buried binding pockets for binder development.

Experimental General Purified human Acetyl cholinesterase was purchased from Sigma Aldrich.

$^1$H NMR spectra were recorded in CDCl$_3$ (7.26 ppm), CD$_3$OD (3.31 ppm), CD$_3$CN:D$_2$O 9:1 (1.94 ppm), acetone-d$_6$ (2.05 ppm) or DMSO-d$_6$ (2.50 ppm) on a Varian Unity Inova 500 spectrometer operating at 499.9 MHz. $^{13}$C NMR spectra were recorded in CDCl$_3$ (77.0 ppm), CD$_3$OD (49.0 ppm), CD$_3$CN:D$_2$O 9:1 (1.32 ppm), acetone-d$_6$ (29.84 ppm) or DMSO-d$_6$ (39.52 ppm) on a Varian Unity 400 spectrometer operating at 100.6 MHz. All spectra were recorded at 25° C. The numbering used in assignment of NMR spectra is shown in Scheme 2. Merck silica gel 60 (230-400 mesh) was used for flash chromatography. TLC was performed using Merck Silica 60 F$_{254}$ gel. TLC or analytical HPLC-MS-ELSD was used to monitor the reactions. Analytical reversed phase HPLC-MS-ELSD was conducted on a Gilson equipped with a Finnigan AQA Thermoquest and a SEDEX 85 LT-ELSD. A Phenomenex Gemini C18 column (5 µm, 110 Å, 150×3.0 mm) and H$_2$O+0.1% HCO$_2$H/MeCN+0.1% HCO$_2$H was used as mobile phase for the analytical HPLC using a flow of 1 mL/min. Preparative reversed phase HPLC was conducted on a Gilson using Phenomenex Luna C8 column (5 µm, 100 Å, 250×30.0 mm). H$_2$O+0.05% HCO$_2$H/MeCN+0.05% HCO$_2$H or H$_2$O+0.1% TFA/MeCN+0.1% TFA was used as mobile phase for the preparative HPLC using a flow of 30 mL/min. For freeze-drying a Heto Lyolab 3000 was used. DMF and benzene were dried using standard methods (Perrin, D. D.; Armarego, W. L. F. Purification of Laboratory Chemicals; 3 ed.; Pergamon Press: Oxford, 1992).

Synthesis of Ligands

9-Phenoxyacridine (2)

Dry benzene (450 mL) was added to 1.50 g acridone (1 equiv.) under N$_2$-atmosphere. SOCl$_2$ (3.37 mL, 6 equiv.) was added and the reaction mixture was refluxed over night followed by removal of solvent by evaporation. Dry DMF (75 mL), phenol (2.17 g, 3 equiv.) and K$_2$CO$_3$ (4.26 g, 3 equiv.) were added under N$_2$. The reaction was stirred at 60° C. for 3.5 days. After filtration and evaporation the crude product was purified using flash chromatography (CH$_2$Cl$_2$ to CH$_2$Cl$_2$:Et$_2$O, 6:1) giving 2.04 g of 2, 98% yield. $^1$H NMR (CDCl$_3$): 8.28 (5+4, br ddd, J=8.9, 1.1, 0.8 Hz, 2H), 8.11 (8+1, ddd, J=8.7, 1.3, 0.8 Hz, 2H), 7.79 (6+3, ddd, J=8.9, 6.6, 1.3 Hz, 2H), 7.47 (7+2, ddd, J=8.7, 6.6, 1.1 Hz, 2H), 7.28 (2'+4', m, 2H), 7.06 (3', m, 1H), 6.86 (1'+5', m, 2H). 3.40 (6, m, 2H).

6-(9'-acridinylamino)hexanoic acid (3)

9-Phenoxyacridine (2) (0.099 g, 1 equiv.) dissolved in 15 mL dry DMF was added to 6-aminohexanoic acid (0.617 g, 12 equiv.) dissolved in 50 mL dry DMF under N$_2$. The reaction mixture was heated at 70° C. for 2 days and at 100° C. for 1 day. After cooling to room temperature (rt) the solvent was evaporated. The crude product was purified by RP-HPLC using MeCN/H$_2$O+0.1% TFA, 35 min gradient from 25 to 30% MeCN, giving 0.148 g 3 with a yield of 76%. $^1$H NMR (CD$_3$OD): 8.34 (8+1, br ddd, J=8.3, 1.2, >0.9 Hz, 2H), 7.84 (6+3, ddd, 8.4, 6.9, 1.2 Hz, 2H), 7.68 (5+4, br ddd, 8.4, 0.9, <0.9 Hz, 2H), 7.45 (7+2, ddd, J=8.3, 6.9, 0.9 Hz, 2H), 4.03 (1', br t, 2H), 2.32 (5', t, J=7.3 Hz, 2H), 1.95 (2', qui, J=7.3 Hz, 2H), 1.68 (4', qui, J=7.3 Hz, 2H), 1.50 (3', qui, J=7.3 Hz, 2H).

$^{13}$C NMR (DMSO-d$_6$): 175.0, 157.7, 139.6, 135.5, 123.8, 118.7, 112.3, 48.9, 33.8, 28.9, 26.1, 24.4.

8-(9'-acridinylamino)octanoic acid (4)

9-Phenoxyacridine (2) (0.218 g, 1 equiv.) dissolved in 25 mL dry DMF was added to 8-aminooctanoic acid (1.580 g, 12 equiv.) dissolved in 25 mL dry DMF under N$_2$. The reaction mixture was heated at 100° C. for 2 days. After cooling to rt the solvent was evaporated. The crude product was purified by flash chromatography using CH$_2$Cl$_2$:MeOH:HCl 6:1:0.007, giving 0.271 g 4 with a yield of 66%. $^1$H NMR (CD$_3$OD): 8.46 (8+1, ddd, J=8.8, 1.3, 0.6 Hz, 2H), 7.92 (6+3, ddd, J=8.6, 6.9, 1.3 Hz, 2H), 7.79 (5+4, ddd, J=8.6, 1.2, 0.6 Hz, 2H), 7.53 (7+2, ddd, J=8.8, 6.9, 1.2 Hz, 2H), 4.11 (1', br t, 2H), 2.26 (7', t, J=7.4 Hz., 2H), 1.98 (2', m, 2H), 1.58 (6', m, 2H), 1.47 (3', m, 2H), 1.44-1.31 (4'+5', m, 4H). $^{13}$C NMR (CD$_3$OD): 177.5, 159.4, 141.0, 136.3, 124.9, 119.5, 113.7, 50.4, 34.8, 30.5, 30.0, 29.9, 27.6, 25.9.

6-[6'-(9"-acridinylamino)hexanoylamido]hexanoic acid (5)

6-('9-acridinylamino)hexanoic acid (3) (0.026 g, 1 equiv.) was dissolved in 6 mL dry DMF under N$_2$. DIPEA (68 µL, 8 equiv.) and HATU (0.029 g, 1.5 equiv.) were added and the reaction mixture was stirred at rt for ~1 h. 6-Aminohexanoic acid (0.013 g, 2 equiv.) was added and the reaction mixture stirred for additional 18 h. H$_2$O (2 mL) was added followed by removal of the solvent by evaporation. The crude product was purified by RP-HPLC using MeCN/H$_2$O+0.05% HCO$_2$H, 30 min gradient from 15 to 18% MeCN, giving 11.4 mg 5 with a yield of 56%. $^1$H NMR (CD$_3$CN:D$_2$O 9:1): 8.35 (8+1, ddd, J=8.6, 1.2, 0.6 Hz, 2H), 7.89 (6+3, ddd, J=8.5, 6.9, 1.2 Hz, 2H), 7.75 (5+4, ddd, J=8.5, 1.1, 0.6 Hz, 2H), 7.49 (7+2, ddd, J=8.6, 6.9, 1.1 Hz, 2H), 4.04 (1', br t, 2H), 3.04 (7', t, J=6.9 Hz, 2H), 2.36 (11', br m, 2H), 2.12 (5', t, J=7.3 Hz, 2H), 1.91 (2', m (partially under solvent), 2H), 1.59 (4', qui, J=7.3 Hz, 2H), 1.50 (10', br m, 2H), 1.44-1.32 (3'+8', m, 4H), 1.23 (9', br m, 2H). $^{13}$C NMR (CD$_3$CN:D$_2$O 9:1): 175.3, 159.2, 140.9, 136.3, 126.5, 124.8, 119.6, 113.5, 50.1, 39.9, 36.6, 29.9, 29.7, 27.2, 26.9, 26.0.

8-[6'-(9"-acridinylamino)hexanoylamido]octanoic acid (6)

6-('9-acridinylamino)hexanoic acid (3) (0.022 g, 1 equiv.) was dissolved in 6 mL dry DMF under N$_2$. DIPEA (5 6 µL, 8 equiv.) and HATU (0.02 4 g, 1.5 equiv.) were added and the reaction mixture was stirred at rt for ~1 h. 8-Aminooctanoic acid (0.013 g, 2 equiv.) was added and the reaction mixture stirred for additional 18 h. H$_2$O (1 mL) was added followed by removal of the solvent by evaporation. The crude product was purified by RP-HPLC using MeCN/H$_2$O+0.1% TFA, 30 min gradient from 25 to 40% MeCN, giving 12 mg 6 with a yield of 44%. $^1$H NMR (CD$_3$CN:D$_2$O 9:1): 8.36 (8+1, ddd, J=8.7, 1.2, 0.6 Hz, 2H), 7.90 (6+3, ddd, J=8.6, 6.9, 1.2 Hz, 2H), 7.76 (5+4, ddd, J=8.6, 1.2, 0.6 Hz, 2H), 7.50 (7+2, ddd, J=8.7, 6.9, 1.2 Hz, 2H), 4.04 (1', br t, 2H), 3.04 (7', t, J=7.0 Hz, 2H), 2.20 (13', t, J=7.3 Hz, 2H), 2.13 (5', t, J=7.3 Hz, 2H), 1.91 (2', m, 2H), 1.60 (4', m, 2H), 1.47 (12', m, 2H), 1.40 (3', m, 2H), 1.35 (8', m, 2H), 1.25-1.16 (11'+10'+9', m, 6H). $^{13}$C NMR (CD$_3$CN:D$_2$O 9:1): 177.1, 175.3, 159.3, 140.8, 136.4, 126.5, 124.9, 119.6, 113.3, 50.1, 40.0, 36.6, 34.7, 29.93, 29.90, 29.6, 29.5, 27.3, 26.9, 26.0, 25.6.

6-[8'-(9"-acridinylamino)octanoylamido]hexanoic acid (7)

8-('9-acridinylamino)octanoic acid (4) (0.029 g, 1 equiv.) was dissolved in 17 mL dry DMF under $N_2$. DIPEA (71 µL, 8 equiv.) and HATU (0.025 g, 1.1 equiv.) were added and the reaction mixture was stirred at rt for ~1 h. 8-Aminohexanoic acid (0.015 g, 2 equiv.) was added and the reaction mixture stirred for additional 3 h. $H_2O$ (2 mL) was added followed by removal of the solvent by evaporation. The crude product was purified by RP-HPLC using MeCN/$H_2O$+0.1% TFA, 30 min isocratic 30% MeCN, giving 7.3 mg 7 with a yield of 21%. $^1H$ NMR ($CD_3CN:D_2O$ 9:1): 8.36 (8+1, ddd, J=8.7, 1.2, 0.5 Hz, 2H), 7.90 (6+3, ddd, J=8.6, 6.9, 1.2 Hz, 2H), 7.76 (5+4, ddd, J=8.6, 1.2, 0.5 Hz, 2H), 7.50 (7+2, ddd, J=8.7, 6.9, 1.2 Hz, 2H), 4.04 (1', br t, 2H), 3.06 (9', t, J=7.0 Hz, 2H), 2.23 (13', t, J=7.4 Hz, 2H), 2.07 (7', t, J=7.4 Hz, 2H), 1.89 (2', m, 2H), 1.55-1.45 (12'+6', m, 4H), 1.44-1.36 (10'+3', m, 4H), 1.32 (4', m, 2H), 1.29-1.19 (11'+5', m, 4H). $^{13}C$ NMR ($CD_3CN:D_2O$ 9:1): 177.0, 175.5, 159.3, 140.7, 136.4, 126.4, 124.9, 119.6, 113.5, 50.2, 39.8, 36.9, 34.6, 30.2, 29.7, 29.6, 29.4, 27.2, 27.0, 26.4, 25.3.

8-[8'-(9"-acridinylamino)octanoylamido]octanoic acid (8)

The TFA salt was removed by adding $K_2CO_3$ (0.015 g, 2 equiv.) to 4 (0.012 g, 1 equiv.) dissolved in ~5 mL MeOH followed by stirring for 5 min. The precipitate was filtered off and the solvent was removed by evaporation. Dry DMF (25 mL) was added under $N_2$. DIPEA (32 µL, 5 equiv.) and HATU (0.022 g, 1.5 equiv.) were added and the reaction mixture was stirred at rt for ~1 h. 8-Aminooctanoic acid (0.013 g, 2 equiv.) was added and the reaction mixture stirred for additional 3 h. $H_2O$ (2 mL) was added followed by removal of the solvent by evaporation. The crude product was purified by RP-HPLC using MeCN/$H_2O$+0.1% TFA, 30 min gradient from 30 to 40% MeCN, giving 8.9 mg 8 with a yield of 58%. $^1H$ NMR ($CD_3OD$): 8.52 (2×$HCO_2H$, br s, 2H), 8.50 (8+1, ddd, J=8.7, 1.2, 0.6 Hz, 2H), 7.96 (6+3, ddd, J=8.6, 6.9, 1.2 Hz, 2H), 7.82 (5+4, ddd, J=8.6, 1.2, 0.6 Hz, 2H), 7.57 (7+2, ddd, J=8.7, 6.9, 1.2 Hz, 2H), 4.15 (1', br t, 2H), 3.13 (9', t, J=7.0 Hz, 2H), 3.22 (15', t, J=7.5 Hz, 2H), 2.16 (7', t, J=7.3 Hz, 2H), 1.98 (2', m, 2H), 1.63-1.53 (6'+14', m, 4H), 1.53-1.38 (3'+12'+10'+4', m, 8H), 1.38-1.28 (5'+11'+13', m, 6H). $^{13}C$ NMR ($CD_3OD$): 179.0, 176.0, 159.6, 141.4, 136.3, 126.6, 124.9, 119.7, 114.0, 50.5, 40.3, 37.2, 37.0, 30.6, 30.4, 30.3, 30.1, 29.94, 29.90, 27.8, 27.7, 26.8, 26.4.

6-[6'-(9"-acridinylamino)hexanoylamido]hexanoic acid p-nitrophenyl ester (9)

5 (11.4 mg, 1 equiv.) was dissolved in ~10 mL MeCN followed by addition of $Et_3N$ (4.15 µL, 1.1 eq). The reaction mixture was cooled to 0° C. 4-nitrophenyl chloroformate (6.2 mg, 1.1 equiv.) was added, after stirring for 5 min DMAP (0.7 mg, 0.2 equiv.) was added and the cooling bath was removed. The reaction was stirred at rt for 3.5 h. The reaction mixture was filtered through a plug of glass wool and directly injected on RP-HPLC using MeCN/$H_2O$+0.05% $HCO_2H$, 30 min gradient from 25 to 35% MeCN. Fractions containing product was directly freezed in $N_2$ (l) after elution, the solvent was removed by lyophilization giving 6.3 mg 9 with a yield of 43%. $^1H$ NMR (acetone-$d_6$): 8.35-8.27 (8+1+3"+5", m, 4H), 7.76-7.60 (5+4+amide+6+3, m, 5H), 7.42 (2"+6", m, 2H), 7.30 (7+2, br ddd, J=8.7, 6.6, <0.9 Hz, 2H), 3.82 (1', br t, J=Hz, 2H), 3.01 (7', m, 2H), 2.60 (11', t, J=7.4 Hz, 2H), 2.02 (5', t, J=7.4 Hz, 2H), 1.74 (2', m, 2H), 1.62 (10', m, 2H), 1.51 (4', m, 2H), 1.39 (8', m, 2H), 1.36-1.28 (9'+3", m, 2H). $^{13}C$ NMR (acetone-$d_6$): 171.8, 171.1, 155.4, 152.3, 145.0, 130.4, 125.3, 125.1, 123.2, 121.6, 50.2, 38.0, 35.4, 33.4, 30.6, 28.8, 26.2, 25.7, 25.1, 23.8. 5a+4a, 8a+9a not found due to broadened resonances and low signal-to-noise in $^{13}C$ NMR spectrum.

8-[6'-(9"-acridinylamino)hexanoylamido]octanoic acid p-nitrophenyl ester (10)

The TFA salt was removed by adding $K_2CO_3$ (2.6 mg, 2 equiv.) to 6 (6.6 mg, 1 equiv.) dissolved in ~5 mL MeOH followed by stirring for 5 min. The precipitate was filtered off and the solvent was removed by evaporation. MeCN (~10 mL) was added to the flask followed by addition of $Et_3N$ (1.5 µL, 1.1 eq). The reaction mixture was cooled to 0° C. 4-nitrophenyl chloroformate (2.7 mg, 1.1 equiv.) was added, after stirring for 5 min DMAP (0.4 mg, 0.2 equiv.) was added and the cooling bath was removed. The reaction was stirred at rt for 4 h. The reaction mixture was filtered through a plug of glass wool and directly injected on RP-HPLC using MeCN/$H_2O$+0.05% $HCO_2H$, 30 min gradient from 25 to 41% MeCN. Fractions containing product was directly freezed in $N_2$ (l) after elution, the solvent was removed by lyophilization giving 3.7 mg 10 with a yield of 57%. $^1H$ NMR (acetone-$d_6$): 8.44 (8+1, unres ddd, J=8.6, 1.2, <0.9 Hz, 2H), 8.31 (3"+5", m, 0.2H), 7.90 (5+4, unres ddd, J=8.6, 0.9, <0.9 Hz, 2H), 7.72 (6+3, ddd, J=8.6, 6.6, 1.2 Hz, 2H), 7.43 (2"+6", m, 2H), 7.40 (7+2, ddd, J=8.6, 6.6, 0.9 Hz, 2H), 7.01 (amide, partially exchanged 1H), 4.00 (1', br t, J=Hz, 2H), 3.18 (7', m, 2H), 2.63 (13', t, J=7.4 Hz, 2H), 2.16 (5', t, J=7.3 Hz, 2H), 1.92 (2', m, 2H), 1.72 (12', m, 2H), 1.66 (4', m, 2H), 1.54-1.45 (3'+8', m, 4H), 1.45-1.27 (10'+11'+9', m, 6H). $^{13}C$ NMR (acetone-$d_6$): 172.8, 171.9, 156.8, 154.2, 147.3, 146.3, 131.7, 126.6, 125.9, 125.4, 123.9, 123.3, 117.0, 51.3, 39.6, 36.5, 34.5, 31.4, 30.4, 29.62, 29.58, 27.6, 27.2, 25.9, 25.3.

6-[8'-(9"-acridinylamino)octanoylamido]hexanoic acid p-nitrophenyl ester (11)

The TFA salt was removed by adding $K_2CO_3$ (2.8 mg, 2 equiv.) to 7 (6.8 mg, 1 equiv.) dissolved in ~5 mL MeOH followed by stirring for 5 min. The precipitate was filtered off and the solvent was removed by evaporation. MeCN (~10 mL) was added to the flask followed by addition of $Et_3N$ (1.5 µL, 1.1 eq). The reaction mixture was cooled to 0° C. 4-nitrophenyl chloroformate (2.8 mg, 1.1 equiv.) was added, after stirring for 5 min DMAP (0.4 mg, 0.2 equiv.) was added and the cooling bath was removed. The reaction was stirred at rt for 4.5 h. The reaction mixture was filtered through a plug of glass wool and directly injected on RP-HPLC using MeCN/$H_2O$+0.05% $HCO_2H$, 30 min gradient from 25 to 40% MeCN. Fractions containing product was directly freezed in $N_2$ (l) after elution, the solvent was removed by lyophilization giving 2.5 mg 11 with a yield of 38%. $^1H$ NMR (acetone-$d_6$): 8.35 (8+1, br ddd, J=8.7, 1.3, 0.6 Hz, 2H), 8.30 (3"+5", m, 2H), 7.87 (5+4, br ddd, J=8.7, 1.3, 0.6 Hz, 2H), 7.64 (6+3, ddd, J=8.7, 6.6, 1.3 Hz, 2H), 7.42 (2"+6", m, 2H), 7.34 (7+2, ddd, J=8.7, 6.6, 1.3 Hz, 2H), 6.96 (amide, partially exchanged 1H), 3.91 (1', br t, J=Hz, 2H), 3.18 (9', m, 2H), 2.64 (13', t, J=7.4 Hz, 2H), 2.07 (7', partially under solvent, 2H), 1.84 (2', m, 2H), 1.74 (12', m, 2H), 1.58-1.49 (6'+10', m, 4H), 1.48-1.40 (11'+3', m, 4H), 1.35-1.25 (5'+4', m, 2H). $^{13}C$ NMR (acetone-$d_6$): 172.7, 171.8, 152.9, 156.7, 149.0, 146.2, 130.6, 125.9, 125.1, 125.0, 123.9, 123.0, 117.8, 51.6, 39.4, 36.7, 34.5, 32.1, 30.2, 29.80, 29.79, 27.5, 27.0, 26.3, 25.1.

8-[8'-(9''-acridinylamino)octanoylamido]octanoic acid p-nitrophenyl ester (12)

The TFA salt was removed by adding $K_2CO_3$ (6.7 mg, 2 equiv.) to 8 (13.7 mg, 1 equiv.) dissolved in ~5 mL MeOH followed by stirring for 5 min. The precipitate was filtered off and the solvent was removed by evaporation. MeCN (~15 mL) was added to the flask followed by addition of $Et_3N$ (3.7 µL, 1.1 eq). The reaction mixture was cooled to 0° C. 4-nitrophenyl chloroformate (6.0 mg, 1.1 equiv.) was added, after stirring for 5 min DMAP (0.6 mg, 0.2 equiv.) was added and the cooling bath was removed. The reaction was stirred at rt for 3 h. The crude product was purified by RP-HPLC using $MeCN/H_2O+0.05\%$ $HCO_2H$, 25 min gradient from 25 to 50% MeCN. Fractions containing product was directly freezed in $N_2$ (l) after elution, the solvent was removed by lyophilization giving 4.4 mg 12 with a yield of 26%. $^1H$ NMR (DMSO-$d_6$): 8.43 (8+1, unres ddd, 2H), 8.28 (3''+5'', m, 2H), 7.86-7.75 (6+3+5+4, m, 4H), 7.69 (amide, br t, J=5.6 Hz, 1H), 7.44 (7+2, unres ddd, 2H), 7.41 (2''+6'', m, 2H), 3.95 (1', br t, 2H), 3.00 (9', dt, J=7.1, 5.6 Hz, 2H), 2.61 (15', t, J=7.4 Hz, 2H), 2.01 (7', t, J=7.4 Hz, 2H), 1.81 (2', m, 2H), 1.62 (14', m, 2H), 1.45 (6', m, 2H), 1.40-1.15 (3'+10'+4'+11'+12'+13'+5', m, 14H). $^{13}C$ NMR (DMSO-$d_6$): 171.8, 171.1, 155.3, 155.1, 144.9, 142.5, 133.0, 125.4, 125.2, 123.1, 122.6, 114.1, 49.4, 38.3, 35.4, 33.4, 29.6, 29.1, 28.5, 28.4, 28.30, 28.25, 26.20, 26.16, 25.2, 24.0.

Synthesis of Peptides

The peptides were synthesized on a Pioneer automated peptide synthesizer using standard fluorenylmethoxycarbonyl (Fmoc) chemistry with O-(7-benzotriazole-1-yl)-1,1,3,3-tetramethyluronium tetrafluoroborate (HBTU, Iris Biotech GmbH) and diisopropylethylamine (DIPEA, Aldrich) as activating agents. Fmoc deprotection of the amino terminal was performed using 20% piperidine in DMF. The synthesis was performed on a 0.2 mmol scale using Fmoc-glycine-polyethyleneglycol-polystyrene (Fmoc-Gly-PEG-PS) resin and a fourfold excess of amino acid in each coupling. The side chains of the amino acids (Calbiochem-Novabiochem AG, Iris Biotech GmbH) were protected by base-stable groups: tert-butyl ester (Asp, Glu), trityl (His, Asn, Gln) and 2,2,4,6,7-pentamethyldihydrobenzofuran-5-sulfonyl (Arg). Orthogonal protection of the lysine residues was used to enable selective deprotection followed by attachment of a fluorescent probe. The lysine residue where the fluorophore was to be conjugated was protected by an allyloxycarbonyl (Alloc) group, whereas the lysine residue where ligand was to be conjugated was protected by a tert-butoxycarbonyl (Boc) group. The N-termini were acetylated using 0.5 M acetic anhydride in DMF.

Deprotection of the Alloc group was performed by treating the resin with tetrakis(triphenylphosphine)palladium(0) (Pd (PPh$_3$)$_4$, 2 equiv.) in DCM, acetic acid and N-methylmorpholine (ratio 37:2:1 v/v; 10 mL per gram of resin) at room temperature under $N_2$ for 2 h. The resin was sequentially washed using 0.5% DIPEA in DMF and 0.5% v/v diethyldithiocarbamic acid in DMF. Coupling of 7-methoxycoumarin-3-carboxylic acid (3 equiv.) to the lysine residue was performed in DMF with gentle stirring at room temperature for 2 h. The coumarin was activated using a coupling cocktail consisting of DIPEA, 1-hydroxybenzotriazole (HOBt), diisopropyl carbodiimide (DIC), ratio 12:6:6. After two hours another aliquot of coupling cocktail was added and the reaction was left over night. In all cases the resins were washed with DMF and DCM between deprotections and couplings. Total deprotection and cleavage from the resin was achieved by adding TFA, water and TIS (95:2.5:2.5 v/v, 10 mL per gram of polymer) for 3 h at room temperature. After filtration and concentration the peptide was precipitated by addition of cold diethyl ether, centrifuged, washed in diethyl ether and dried in air.

The crude peptides were purified by reversed-phase HPLC using semi-preparative Hypersil C-18 Gold column (150×20 mm, pore size 175 Å, particle size 5 Å) or semi-preparative Kromasil C8 Hichrom column (250×21.2 mm, pore size 100 Å, particle size 10 Å) eluted with a shallow 35-55% acetonitrile gradient in water and 0.1% TFA as additive at a flow rate of 10 mL/min. Collected fractions were identified by MALDI-TOF mass spectrometry (Bruker Daltonics Ultraflex II TOF/TOF), concentrated and lyophilized twice.

The ligands were conjugated to the polypeptides by adding the corresponding ester (3-5 equiv.) dissolved in DMSO (~0.1 M) to a 2 mM polypeptide solution in DMSO with 1% DIPEA as additive. The reaction was left for 12 to 48 hours at rt followed by analytical HPLC and MALDI-TOF-MS. A Genesis C-18 column (250×4.6 mm, pore size 120 Å, particle size 4 Å) was used for the analytical HPLC. A gradient of 30-60% acetonitrile in water and 0.1% TFA as additive over 90 min at a flow rate of 1 mL/min was used. Conjugated polypeptides were used in the fluorescence screening without further purification, whereas in the case of further reaction steps (eg. Acm deprotection) they were purified by precipitation in cold methyl-tertbutyl ether, re-dissolved in trifluoroacetic acid and precipitated using cold diethyl ether, collected and dried in air.

Binders with an Acm protected cysteine in position 24 were synthesized to enable attachment to nanoparticles. The Acm group was removed by treatment with Silver triflate (AgOTf). The peptide (2 mg, 0.3 µmol) was dissolved in 0.5 mL of TFA/anisole (99:1). Silver triflate (10 mg, 100 equiv.) was added to the solution and the mixture was stirred at 0° C. for 1 hour followed by 2 to 12 hours stirring at room temperature. The peptide silver salt was precipitated using cold diethyl ether and centrifuged. The supernatant was removed and the remaining peptide silver salt was stirred with dithioeritriol (DTT) (50 equiv.) in 50% (v/v) acetic acid in water for 2 to 12 hours at room temperature. The mixture was centrifuged and the supernatant solution was purified by HPLC, followed by lyophilization.

Fluorescence Measurements.

Titration of the polypeptides with human AChE was made using a SpectraMax GeminiXPS platereader. NUNC™ polystyrene 384 plates were coated with Pluronic® F108NF Prill Poloxamer338 (BASF) and polypeptide before use; the plates were incubated in a 1% water solution of Pluronics over night followed by thorough washing by water, thereafter incubated with a 0.4 mg/mL blocking peptide solution. A polypeptide concentration of 500 nM in 90 µL was used and obtained by dilution from stock solutions (concentration 2 mM) with 50 mM potassium phosphate buffer pH 7.0. The polypeptides were titrated by adding aliquots of 1 and 2 equiv. of enzyme. After addition of enzyme the plate was let to equilibrate for 20 minutes. The coumarin fluorophore was excited at 350 nm and the emission was recorded at 370-450 nm. One blank was made for each polypeptide by adding the same volume of buffer instead of enzyme solution. One blank for each polypeptide was also made without adding anything.

Conjugation to Polystyrene Nanoparticles and Extraction from CSF.

Pluronic F108-PDS (Allvivo Inc.) was adsorbed to polystyrene latex nanoparticles (Bangs laboratories Inc.) by incubating a 2% (w/v) suspension of particles with 10 mg/mL of Pluronic F108-PDS over night at room temperature under constant shaking. After adsorption the excess surfactant was separated from the coated particles by centrifugation at 14000 rpm for 5 minutes using an Eppendorff tabletop centrifuge. The supernatant was removed and the particles were resuspended in 10 mM Hepes buffer pH 7.4. This washing procedure was repeated three times before adding the cystein deprotected polypeptide conjugates as a 1 mg/mL solution in 10 mM Hepes buffer pH 7.4. The reaction mixture was left with gentle shaking for 1 to 12 hours. The nanoparticles were then washed thrice with buffer and resuspended in 100 µL buffer and thereafter incubated with 200 to 500 µL Cerebrospinal fluid (from Uppsala University Hospital) at room temperature with gentle shaking. After one hour the mixture was centrifuged and the supernatant was removed and the particles were washed with buffer thrice. The nanoparticles were divided in two parts, where one part was used for ELISA (see below) and one part were treated as follows: the binders together with their captured proteins were cleaved from the particles by reductive cleavage using 50 mM DTT in Hepes buffer pH 7.4 followed by centrifugation (14000 rpm, 5 min.) to remove the particles from the samples. Aliquots of 8 µL of the supernatants were analyzed by gradient SDS-PAGE gels electrophoresis using NuPAGE® Novex Bis-Tris 4-12% (v/w) gel and MES running buffer (Invitrogen). After electrophoresis the gels were fixed in 100 mL fixation buffer (40% ethanol, 10% acetic acid) and silver stained using the SilverQuest™ silver staining kit (Invitrogen) or fixed in 100 mL fixation buffer (35% methanol, 10% acetic acid) and stained using Colloidal Blue staining kit (Invitrogen).

Preparation of Antibody-Enzyme Conjugates for ELISA

Aliquots of 10 µL of 20 mM Succinimidyl 6-(3-[2-pyridyldithio]-propionamido)hexanoate (LC-SPDP) (Thermo Scientific) were added to 0.5 mg Horseradish Peroxidase (HRP) (Sigma) and incubated at room temperature for 30 min. Excess reagent was removed by desalting using a NAP5 column (GE Healthcare). An additional 10 µL aliquot of LC-SPDP was added to 0.5 mL of anti-AChE sheep polyclonal IgG antibody (1 mg/mL, Abcam) and the mixture was incubated for 30 min followed by a desalting step using a NAP5 column. Part (0.5 mL) of the resulting solution was then reduced with DTT (25 µL of 0.25 M DTT at room temperature for 20 min), again desalted (NAP5 column) and immediately transferred to the LC-SPDP-modified HRP. The conjugation was allowed to proceed for 1 h at room temperature.

ELISA

The presence of captured hAChE from CSF by the binders immobilized on nanoparticles was also analysed in an ELISA. This was done by taking out 15 µL of the particle suspension after incubation in CSF and subsequent washing. As a reference the same amount of particles coated with Pluronic F108, but without the binders, was used. The diluted conjugates (20 µL) were added to the two particle suspensions and incubated for 20 min. Unbound conjugates were removed by washing the particles 4 times, as described in the section above, and the particles were finally resuspended in 100 µL PBS. After addition of 100 µL substrate (50/50 of luminol+ enhancer and peroxide, Thermo Fisher) the luminescence was red in a SpectraMax Gemeni XPS plate-reader at 425 nm.

Example 2

In Example 2, human Carbonic Anhydrase II (HCAII) was used as the target molecule.

Design and Synthesis.

The small molecule warhead used to bind HCA was benzenesulphonamidecarboxylic acid, an inhibitor of HCAI and HCAII with dissociation constant $K_d$ of 1.1-3.9 µM for HCAI (DeGrado, W. F., Summa, C. M., Pavone, V., Nastri, F. & Lombardi. A. Ann. Rev. Biochem. 68, 779-819 (1999). Jeckling, M. C.; Schauer, S.; Dumelin, C. E.; Zenobi, R. J. Mol. Recognit. 2009; 22: 319-329) and 1.3-1.5 µM for HCAII (Enander, K.; Dolphin, G. T.; Liedberg, B.; Lundström, I.; Baltzer, L Chem Eur J, 2004, 10, 2375-2385. Baltzer, L. Topics in Current Chemistry 2007, 277, 89-106. DeGrado, W. F., Summa, C. M., Pavone, V., Nastri, F. & Lombardi. A. Ann. Rev. Biochem. 68, 779-819 (1999)). It was linked to the polypeptide of the invention via an aminohexanoic acid spacer that has been shown previously to allow the benzenesulphonamide residue and the scaffold sequence KE2 to interact cooperatively with HCAII (Krebs, H. A. Biochem. J. 1948, 43, 525-528) (FIG. 3). It was assumed that the inhibitor benzenesulphonamide would bind to the active site of HCAII and that the polypeptide scaffold would bind to the surface of the protein. The folded polypeptide does not fit into the binding pocket of HCAII and has to interact with surface residues. When the small molecule and the polypeptide scaffold bind simultaneously the overall affinity is several orders of magnitude higher than that of the small molecule alone thus providing a convenient route to high-affinity binders for proteins The polypeptides were synthesized by automated solid phase peptide synthesis according to standard Fmoc protocols, purified by reversed phase HPLC and identified by MALDI-TOF mass spectrometry. Each polypeptide was pure according to HPLC, we estimate >95%, and the molecular masses of the purified peptides were all within one mass unit of the theoretical values. Each polypeptide was equipped with a 7-methoxycoumarin fluorescent probe, introduced on the solid phase at the side chain of a lysine residue after selective removal of an Alloc protection group by $Pd(PPh_3)_4$. The fluorophore was introduced to enable detection of binding to the target protein by the measurement of fluorescence intensities. In each sequence the fluorophore was introduced in the proximity of the ligand attachment site, i.e. in positions 15, 10, 25 and 37, with the small molecule ligands in positions 8, 17, 22 and 34 respectively. It was expected that the change in molecular environment upon binding would be the most pronounced in those positions and give rise to the largest changes in intensity. The design and structural analysis of similar sequences by NMR and CD spectroscopy as well as by analytical ultracentrifugation have been described in detail previously (Olofsson, S.; Johansson, G.; Baltzer, L. J. Chem. Soc., Perkin Trans. 2 1995, 2047-2056. Broo, K. S., Brive, L., Ahlberg, P. and Baltzer, L., J. Am. Chem. Soc. 1997, 119, 11362-11372). They fold into helix-loop-helix motifs and dimerise to form four-helix bundles with molten globule like properties.

The mean residue ellipticities at 222 nm, $[\theta]_{222}$, □ of the sixteen scaffold polypeptides were recorded at two concentrations, approximately 30 µM and approximately 1 µM, to characterize the state of aggregation, cf. Table 1.

TABLE 1

Mean residue ellipticity of inventive polypeptides in the library at low and high concentration. The experimental error is estimated to be ±1000 deg cm² dmol⁻¹

| Peptide | high concentration ($\mu$M) | $[\theta]_{222}$ at high concentration (deg cm² dmol⁻¹) | $[\theta]_{222}$ at low concentration (deg cm² dmol⁻¹) | low concentration ($\mu$M) |
|---|---|---|---|---|
| 1-C15L8 | 132 | −17800 | −25100 | 3 |
| 2-C15L8 | 147 | −24900 | −20800 | 3 |
| 3-C15L8 | 139 | −23400 | −19700 | 3 |
| 4-C15L8 | 143 | −22000 | −15300 | 3 |
| 1-C10L17 | 30 | −18200 | −11800 | 1 |
| 2-C10L17 | 230 | −23400 | −20400 | 5 |
| 3-C10L17 | 177 | −22400 | −20700 | 4 |
| 4-C10L17 | 121 | −19500 | −11800 | 2 |
| 1-C25L22 | 94 | −24800 | −18000 | 2 |
| 2-C25L22 | 155 | −25000 | −24800 | 3 |
| 3-C25L22 | 149 | −26400 | −23000 | 3 |
| 4-C25L22 | 160 | −23700 | −18200 | 3 |
| 1-C37L34 | 127 | −16900 | −11000 | 3 |
| 2-C37L34 | 150 | −23900 | −30300 | 3 |
| 3-C37L34 | 193 | −22500 | −22200 | 4 |
| 4-C37L34 | 148 | −19600 | −14900 | 3 |

The degree of helix formation is related to the monomer-dimer equilibrium since monomers are unordered with low helical content whereas dimers are highly helical. All sequences were highly helical at the higher of the two concentrations with mean residue ellipticities of around −20 000 deg cm² dmol⁻¹ and some showed partial dissociation at the lower of the two concentrations. All sequences therefore predominantly formed dimers at low $\mu$M concentrations. ¹H NMR spectra of selected sequences have been recorded previously and with one surprising exception, all showed the hallmarks of molten globules. The sequence KE2-C15 with a dansyl group attached to the side chain of Lys-15 showed a well-dispersed NMR spectrum, although the melting behavior was poorly defined. While the ¹H NMR spectra have not been recorded of all sequences and of all polypeptide conjugates, it is likely that the sequences presented here are best described as molten globules.

The synthesis of the spacered benzenesulphonamide and its active ester has been described previosuly (Winum, J.-Y.; Vullo, D. Casini, A.; Montero, J.-L.; Scozzafava, A.; Supuran, C. T. J. Med. Chem. 2003, 46, 2197-2204).

The N-hydroxysuccinimide ester of the benzenesulphonamide residue was reacted with each member of the 16-membered set in a one-step reaction in either buffer or DMSO solution to form the conjugate molecules.

The Affinity of Polypeptide Conjugate Binders for HCAII.

The affinity of each polypeptide conjugate for HCAII was estimated in a screening procedure where 1, 2 and 3 equiv. of HCAII were added to wells containing the polypeptide conjugates and analysed in a plate reader where the intensities of the coumarin fluorescence were compared to samples with no added protein. The experiment was designed to give final HCAII concentrations of 500 nM, 1 $\mu$M and 1.5 $\mu$M and a final binder concentration of 500 nM in 50 mM Hepes buffer at pH 7.4 containing 150 mM NaCl. All solutions were prepared in parallel in separate wells of a 384 microtiter plate, and the intensity of each well recorded simultaneously to avoid differences in intensity due to differences in incubation time. Fluorescence intensities at 280 to 500 nm after excitation at 350 nm were measured using a microtiter plate reader. Polystyrene plates were pre-coated with Pluronics® F-108NF Prill (1% solution in water) and a solution of a 42-residue peptide (0.4 mg/ml, 2 h, sequence 4-C15L8-Ac (i.e. AcNAADJEAKIRHLREKJAARGPRDAAQ-JAEQLARRFERFARAG-CONH₂) to avoid adhesion of binder and protein to the polystyrene surface. Fluorescence intensities (i.e. maximum at 410 nm) of protein-binder mixtures were compared to intensities of binders without protein and a significant change in fluorescence intensity in the presence of one equivalent of protein, in comparison to that of binder without protein, was interpreted as complexation of HCAII by the binder. The binders that showed a change in intensity in the presence of 500 nM HCAII but no further change in intensity in the presence of 1 $\mu$M HCAII were chosen for further studies. Thus the binder was assumed to be more than 90% complexed at 500 nM concentration of protein and 500 nM concentration of binder and under that assumption a dissociation constant, $K_d$, of 10 nM or less can be estimated according to the standard equation for a bimolecular complex: $K_d=[B]*[P]/[PB]$ In the set of sixteen candidate binders prepared and analyzed according to the above procedure three polypeptide conjugates 1-C10L17-B, 3-C15L8-B and 4-C37L34-B were chosen for further studies.

Figure 5:
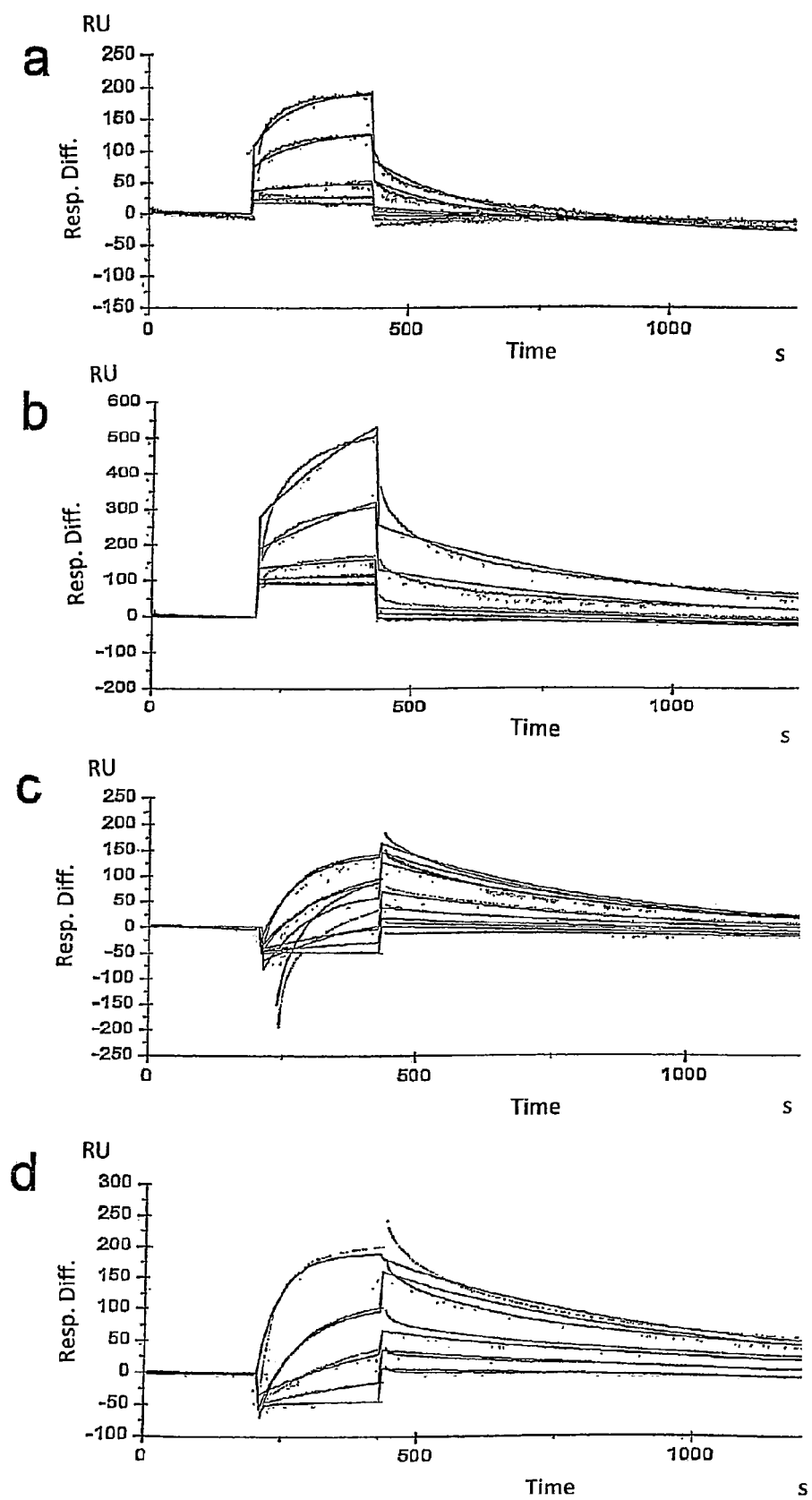
FIG. 5 shows the curves obtained in an SPR analysis of the binders 3-C15L8-B and 4-C37L34-B. Seven different concentrations (2.4 nM to 240 nM for 3-C15L8-B and 3.6 nM to 360 nM for 4-C37L34-B) of the two binders were flown over a CM5 chip with HCAI and HCAII immobilized in different flow cells. A: 3-C15L8-B flown over immobilized HCAI, B: 4-C37L34-B flown over immobilized HCAI, C: 3-C15L8 flown over immobilized HCAII, D: 4-C37L34-B flown over immobilized HCAII.

The affinities for HCAII of 1-C10L17-B, 3-C15L8-B and 4-C37L34-B were determined by fluorescence titration and by SPR analysis (FIG. 5). In order to be able to determine low nM dissociation constants with accuracy, measurements have to be carried out at concentrations of the same order of magnitude. 7-Methoxycoumarine is not sensitive enough to permit accurate titrations at around 10 nM or lower because the signal intensity is too weak. An acetamidomethyl (Acm) protected Cys residue was therefore introduced into the loop regions of 1-C10L17-B and 3-C15L8-B to allow the introduction of a more intense fluorphore. The Cys side chain was deprotected (Fuiji, N.; Otaka, A.; Watanbe, T.; Okamachi, A.; Tamamura, H.; Yajima, H.; Inagaki, Y.; Nomizu, M.; Asano, K. Chem. Soc., Chem. Commun. 1989, 283-284) and reacted with a fluorescein conjugated to maleimide via an aliphatic spacer to enable accurate measurement of affinity at around 50 nM or below in a plate reader, an order of magnitude lower than what was possible with the 7-methoxycoumarin. The fluorescence titrations were carried out using polypeptides conjugated to a dansyl group rather than a 7-methoxycoumarin to avoid overlap with fluorescein, but a fluorophore is present in each sequence of the scaffold library to simplify identification and quantification throughout synthesis and purification. All solutions were prepared in parallel in separate wells of a 384 microtiter plate, and the intensity of each well recorded simultaneously to avoid differences in intensity due to differences in incubation time. Fluorescence intensities after excitation at 420 nm were measured using a microtiter plate reader and polystyrene plates pre-coated as described above. Fluorescence intensities of protein-binder mixtures were compared to intensities of binders without protein. The analysis was performed in 50 mM Hepes buffer at pH 7.4 containing 150 mM NaCl. HCAII was added in 25 steps over a concentration range from 20 pM to 1 $\mu$M to the binder at 50 nM concentration and the results analyzed by curve fitting. While there are differences in structure between dansyl and 7-methoxycoumarin, the differences are relatively small and we assume that the effect on the measured affinities is small. The highest measured affinity was that of 1-C10L17-B with a $K_d$ of 5±3 nM, whereas 3-C15L8-B was found to have a $K_d$ of 29±10 nM. The sequence 4-C37L34-B conjugated to a fluorescein probe was poorly soluble in buffer and was not titrated.

The sixteen polypeptide conjugates were also characterized by SPR biosensor analysis (Biacore®, GE Healthcare), using a Biacore® 2000 instrument, Biacore® CM-5 chip and HBS-EP buffer pH 7.4 (Biacore®, GE Healthcare) with addition of 1% DMSO for the interaction studies. Peptide solutions were prepared by dilution in buffer from 20 µM stock solutions in DMSO. HCAII was immobilized on the chip using standard EDC/NHS coupling in Acetate buffer pH 5.5. The binders were allowed to flow over the chip at 7 concentrations in the range from 1 nM to 500 nM and the interactions were evaluated using a 1:1 binding model (BiaEvaluation).

The affinities of 3-C15L8-B and 4-C37L34-B for HCAII determined by SPR biosensor analysis were 43 nM and 15 nM, respectively, in broad agreement with the affinity reported for KE2-D(15)-6[5]. The dissociation constants differ somewhat between determinations with different methods and between binders equipped with different fluorophores. However, there is in general an agreement between measurements and we conclude that the conjugation of the benzenesulphonamide group to polypeptide scaffolds gives rise to binders with affinities that are more than two orders of magnitude higher than those of the small molecule warhead. In the determination of affinity by SPR analysis the binder 1-C10L17-B was found to have a Kd of 80 nM and it was not considered further for evaluation of selectivity.

Selectivities of Candidate Binders.

The selectivities for HCAII of the binders 3-C15L8-B and 4-C37L34-B were investigated in the complex medium of blood. The selected binders were resynthesized with an Acm-protected Cys residue in position 24. After removal of the Acm group the binders were immobilized on polystyrene nanoparticles coated with Pluronic® F108-PDS, by incubation for 1 hour in 10 mM Phosphate buffer at pH 7.4 containing 150 mM NaCl. The coating material forms monolayers of PEG equipped with activated disulfide groups that spontaneously react with free thiols under the release of 2-mercaptopyridine (Fromell, K., Hulting, G., Ilichev, A., Larsson, A. & Caldwell, K. C. Analytical Chemistry 79, 8601-07 (2007)).

Approximately 60 µL of freshly drawn blood was lysed by dilution in 240 µL of distilled water followed by centrifugation to remove cell debris. HCAII resides in the red blood cells and in order to access the protein, cells have to be lysed. The supernatant was isolated and incubated with the functionalized nanoparticles for 30 minutes to allow them to capture HCAII. The particles were washed three times in PBS, and centrifuged after each wash. The binders and the captured proteins were cleaved from the particles using dithiothreitol and separated from the particles by centrifugation. The supernatant was applied to the electrophoresis gel and after electrophoresis the gel was developed by silver staining (FIG. 4). Three bands were found and identified as a hemoglobin subunit, HSA and human Carbonic Anhydrase by mass spectrometry. The hemoglobin subunit and HSA are both present in the lines of the control beads that have no binders attached and are therefore non-specifically adsorbed by the polystyrene nanoparticles and not extracted by the polypeptide binders. The binder molecules 3-C15L8-B and 4-C37L34-B therefore extract Carbonic Anhydrases predominantly.

The extraction of HCAII was confirmed in an ELISA where the functionalized nanoparticles were used to capture HCAII and an antiHCAII antibody conjugated to HRP was used for detection (data not shown).

There are two isoforms of human Carbonic Anhydrase, HCA I and HCAII, in blood. These two isoforms have nearly identical molecular weights and an overall sequence identity of 60% while the identity for surface accessible residues are slightly lower at 45%. HCAI and HCAII cannot be separated by SDS-PAGE and from the gel (FIG. 4) it is not possible to conclude whether it is HCAI or HCAII or both that have been extracted by 3-C15L8-B and 4-C37L34-B from blood. The bands from the gel were cut, cryptically digested and analysed by MALDI-TOF-MS, displaying that the bands contained both isoforms. HCAI is present in excess over HCAII by a factor of 5-7 in humans, and in order to specifically bind HCAII an affinity difference of several orders of magnitude would be required. Both isoforms bind the benzenesulphonamide inhibitor with a $K_d$ around 1-4 µM, and any differences in affinity for the two isoforms would have to be the result of differences in interactions between the polypeptide and the two proteins. There are numerous ways to design binders for either HCAI or HCAII by using small molecule inhibitors that are specific for the desired isoform, the question addressed here is what difference in discrimination between two isoforms of human Carbonic Anhydrase can be achieved by the polypeptide. It represents a critical test of the level of selectivity that can be achieved by this new class of protein binders, and a further analysis of the discriminating power of the synthetic binder was therefore undertaken by SPR biosensor (Biacore) analysis.

HCAI and HCAII were immobilized in different flowcells on a CM-5 (Biacore) chip using standard EDC/NHS coupling in Acetate buffer at pH 5.5. Measurements of affinities for 3-C15L8-B and 4-C37L34-B were carried out using binder concentrations in the range from 1 nM to 500 nM all with 1% DMSO present and the best fit to the experimental results of an equation describing a 1:1 interaction model was used to determine dissociation constants. The results are shown in Table 2.

TABLE 2

| | Affinity data from SPR analysis | | | | | |
|---|---|---|---|---|---|---|
| | HCAI | | | HCAII | | |
| Ligand-polypeptide conjugate | $K_{off}$ [s$^{-1}$] | $K_{on}$ [M$^{-1}$s$^{-1}$] | $K_d$ [M] | $K_{off}$ [s$^{-1}$] | $K_{on}$ [M$^{-1}$s$^{-1}$] | $K_d$ [M] |
| 3-C15L8-B | 1.4E+04 | 5.5E−03 | 3.9E−07 | 4.2E+04 | 2.5E−03 | 6.0E−08 |
| 4-C34L37-B | 4.4E+03 | 2.1E−03 | 4.7E−07 | 8.2E+04 | 1.4E−03 | 1.7E−08 |

The polypeptide conjugate 3-C15L8-B binds with a dissociation constant of 390 nM for HCAI and 60 nM for HCAII, whereas 4-C37L34-B shows dissociation constant of 470 nM for HCAI and 17 nM for HCAII. The binder molecule 4-C37L34-B is thus capable of discriminating between HCAI and HCAII by a factor of approximately 30, more than an order of magnitude. Although there is cross reactivity and the binders are not completely specific, the demonstrated discrimination is remarkable in view of the simplicity of the binder molecules. Both HCAI and HCAII bind benzensulphonamide and the differential binding of the polypeptide conjugates is clearly due to the interactions with the polypeptide. An clue to why the interactions with the protein surfaces are different is obtained by mapping the electrostatic potentials of the surfaces, FIG. 4. The surface exposed residues are only 45% identical and the area surrounding the active site of HCAII is more hydrophobic and less positively charged than that of HCAI. Although the more negatively charged surface of HCAI would be expected to interact more strongly with the slightly more positively charged polypeptide 4-C37L34 it appears that the hydrophobic interactions dominate favoring the interaction between HCAII and 4-C37L34-B.

Conclusion.

In this Example, it is shown that a polypeptide according to the invention and a small organic molecule with moderate affinity for HCAII can be combined to form a specific high-affinity binder for the protein. In particular, the specificity of the synthetic binder molecule is comparable to that of a monoclonal antibody, as only human Carbonic Anhydrases are extracted by the binder molecules from blood. The observed extraction of a hemoglobin subunit and HSA is due to non-specific adsorption on the polystyrene beads. The discrimination between isoforms of proteins with 60% homology presents a considerable challenge and the achieved affinity difference of almost an order of magnitude is a powerful demonstration of the discriminatory capacity of this type of binder molecules. The use of a small set of polypeptides which are varied in a systematic manner and encoded with elements of affinity and selectivity contrasts with the typical procedures well established in molecular biology where huge libraries of binder candidates are used in the search for good binder molecules. The size of the polypeptide conjugate shown to bind HCAII is less than 1/30 of an IgG monoclonal antibody and not preorganized to form a surface that is shape and charge complementary to the target protein. In spite of these seemingly negative features of the binder molecules presented here they perform extremely well in the recognition and binding of proteins even in the complex environment of human blood. The use of a small set of polypeptide scaffolds in the search for specific high-affinity binders for proteins provides an efficient route to specificity and high affinity, and reduces the search for binders to the search for medium affinity small molecules or peptides. In this study with HCAII we have $[\theta]_{222}$ demonstrated a fast route to several binders with high affinity and this method can thus also be used to construct an array of binders for the measurement of concentration on chip.

The screening procedure depends on the assumption that there is a change of molecular environment surrounding the fluorophore, and that a change in fluorescence reflects binding to the target protein. This may not be true in every case as one cannot predict the structure of the protein-binder complex. However, the procedure described here has allowed the identification of three candidate binders with high affinities and thus the screening protocol shows great promise in the identification of tight binders. From the set of 16 polypeptides three were identified as hits and the possibility that good binders escaped identification is acceptable in view of the fact that the time taken to search the binder candidate set would otherwise take too long to be practical.

The most demanding aspect of protein recognition is that of specificity in complex biological environments, where huge numbers of biomolecules compete for binding. The synthetic polypeptide conjugate 4-C37L34-B has proven good specificity, not only by discriminating not only between Carbonic Anhydrases and other proteins but also between the two isoforms HCAI and HCAII. This suggests that chemically generated binder molecules offer improved performance over those generated by the methods of molecular biology and can be expected to have many advantages in diagnostic as well as pharmaceutical applications.

Experimental

General

HCAI and HCAII were purchased from Sigma as lyophilized powders, solutions were prepared directly before use.

Synthesis of Ligand

The Benzenesulphonamide ligand was synthesized as described previously (Winum, J.-Y.; Vullo, D. Casini, A.; Montero, J-L.; Scozzafava, A.; Supuran, C. T. J. Med. Chem. 2003, 46, 2197-2204).

Synthesis of Peptides.

The peptides were synthesized on a Pioneer automated peptide synthesizer using standard fluorenylmethoxycarbonyl (Fmoc) chemistry with O-(7-benzotriazole-1-yl)-1,1,3,3-tetramethyluronium tetrafluoroborate (HBTU, Iris Biotech GmbH) and diisopropylethylamine (DIPEA, Aldrich) as activating agents. Fmoc deprotection of the amino terminal was performed using 20% piperidine in DMF. The synthesis was performed on a 0.2 mmol scale using Fmoc-glycine-polyethyleneglycol-polystyrene (Fmoc-Gly-PEG-PS) resin and a fourfold excess of amino acid was used in each coupling. The side chains of the amino acids (Calbiochem-Novabiochem AG, Iris Biotech GmbH) were protected by the base-stable groups tert-butyl ester (Asp, Glu), trityl (His, Asn, Gln) and 2,2,4,6,7-pentamethyldihydrobenzofuran-5-sulfonyl (Arg). The lysine residue to be coupled to a fluorophor was orthogonally protected by an allyloxycarbonyl (Alloc) group whereas the lysine where ligand was to be conjugated was protected by a tert-butoxymethyl (Boc) group. The N-terminus was acetylated using 0.5 M acetic anhydride in DMF.

Deprotection of the Alloc group was performed by treating the resin with tetrakis(triphenylphosphine)palladium(0) (Pd(PPh$_3$)$_4$, 2 eq) in DCM, acetic acid and N-methylmorpholine (ratio 37:2:1 v/v; 10 ml per gram of resin) at room temperature under N$_2$ for 2 h. The resin was sequentially washed using 0.5% DIPEA in DMF and 0.5% v/v diethylditiocarbamic acid in DMF. Coupling of 7-methoxycoumarin-3-carboxylic acid (3 eq) to the lysine residue was performed in DMF with gentle stirring at room temperature for 2 h. The coumarin was activated using a coupling cocktail consisting of DIPEA, 1-hydroxybenzotriazole (HOBt), diisopropyl carbodiimide (DIC), ratio 12:6:6. After two hours another aliquot of coupling cocktail was added and the reaction was left over night. In all cases the resins were washed with DMF and DCM between deprotection and coupling. Total deprotection and cleavage from the resin was achieved by adding TFA, water and triisopropylsilane (TIS) (95:2.5:2.5 v/v, 10 ml per gram of polymer) for 3 h at room temperature. After filtration and concentration the peptide was precipitated by addition of cold diethyl ether, centrifuged, washed in diethyl ether and dried in air.

The crude peptides were purified by reversed-phase HPLC using semi-preparative Hypersil C-18 Gold column (150×20 mm, pore size 175 Å, particle size 5 Å) or semi-preparative Kromasil C8 Hichrom column (250×21.2 mm, pore size 100 Å, particle size 10 Å) eluted with a shallow 35-55% acetonitrile gradient in water and 0.1% TFA as additive at a flow rate of 10 ml/min. Collected fractions were identified by MALDI-TOF mass spectrometry (Bruker Daltonics Ultraflex II TOF/TOF), concentrated and lyophilized twice.

The ligands were conjugated to the polypeptides by adding the corresponding ester (4 eq) dissolved in DMSO (~0.1 M) to a 30 µl 2 mM polypeptide solution in DMSO with 1% DIPEA. The reaction was left over night at rt and the degree of functionalization was confirmed by analytical HPLC and MALDI-TOF-MS. A Genesis C-18 column (250×4.6 mm, pore size 120 Å, particle size 4 Å) was used for the analytical HPLC. A gradient of 30-60% acetonitrile in water and 0.1%

TFA as additive over 90 min at a flow rate of 1 ml/min was used. The reaction mixtures were used without further purification for fluorescence screening experiments (diluted to 10 µM stock solutions in 50 mM TRIS buffer, pH 7 containing 150 mM NaCl).

The binders 4-C37L34-B and 3-C15L8-B (where "-B" indicates that the polypeptide is attached to a ligand for the selected molecule) were synthesized and purified with an Acm protected cystein residue in the loop region, C37L34-B-Cys24 and 3-C15L8-B-Cys24.

The binders 1-C10L17-B and 3-C15L8-B for fluorescence titration experiments were conjugated to the benzenesulphonamide residue and the Acm group deprotected.

A typical labeling experiment was performed as follows. The Acm deprotected polypeptide was dissolved in 0.1 M sodium phosphate buffer, containing 6M guanidium hydrochloride, pH 7.5, to a final concentration of 1.0 mM. Three molar equivalents of N-(5-Fluoresceinyl)maleimide (Sigma-Aldrich) was pre-dissolved in a minimum amount of DMSO and directly added to the reaction mixture. The reaction was monitored by analytical HPLC, and it was essentially complete after 4 h. The product was purified by HPLC and the product mass was identified with MALDI-MS.

The binders 4-C37L34-B and 3-C15L8-B for final SPR experiments and the binders 4-C37L34-B-Cys24 and 3-C15L8-B-Cys24 for selectivity studies were conjugated to the benzenesulphonamide residue on a 5 mg scale, and purified by reversed-phase HPLC using semi-preparative Hypersil C-18 Gold column (150×20 mm, pore size 175 Å, particle size 5 Å) eluted with a shallow 30-60% acetonitrile gradient in water and 0.1% TFA as additive at a flow rate of 10 ml/min. Collected fractions were identified by MALDI-TOF mass spectrometry (Applied Biosystem Voyager PRO), concentrated and lyophilized. Stock solutions of 4-C37L34-B and 3-C15L8-B were prepared in DMSO and analyzed by quantitative amino acid analysis. The concentrations of the stock solutions of 4-C37L34-B and 3-C15L8-B were 35 µM and 24 µM respectively.

Deprotection of the Acm group was performed by dissolving the lyophilized peptide (1 µmol) in 0.50 mL of TFA containing 2% (v/v) of anisole. The solution was cooled to 0° C. and a solution of AgOTf (26 mg, 0.1 mmol, 100 equiv) in 0.5 mL TFA was added. The reaction mixture was stirred at 0° C. for 1 h and, allowed to reach ambient temperature and stirred for 2 hours at ambient temperature. The silver salt of the peptide was precipitated from the reaction mixture by adding cold diethyl ether and isolated by centrifugation. The precipitate was dissolved in 0.5 mL distilled water and a solution of dithiothreitol (8 mg, 0.05 mmol, 50 equiv) in 0.5 mL glacial acetic acid was added to the solution of the peptide. The mixture was allowed to stir for 2 hours and centrifuged. The peptide contained in the supernatant solution was purified by HPLC.

Fluorescence Measurements.

Fluorescence spectra were recorded using a GeminiXPS platereader. NUNC™ polystyrene 384 plates were coated with Pluronic® F108NF Prill Poloxamer338 (BASF) before use, the plates were incubated in a 1% aqueous solution of Pluronic over night followed by thorough washing by water and then coated with 0.4 mg/ml peptide solution for 2 hours and washed with water 10 times. A polypeptide concentration of 500 nM in 95 µL was used and obtained by dilution from 10 µM stock solutions with 50 mM TRIS buffer, pH 7 containing 150 mM NaCl. HCAII was added from a 14 µM stock solution to the wells of the mictrotiter plate. The concentration was determined by UV spectroscopy at 280 nm, using an extinction coefficient of 54 000 $M^{-1}$ $cm^{-1}$.

The coumarin probe was excited at 350 nm and the emission was recorded in the interval 380-500 nm. All measurements were performed at room temperature and were made in triplicates. The wells were read after 5 min and after 30 min.

SPR Measurements

SPR measurements were performed on a Biacore® 2000 instrument, with the proteins immobilized on a Biacore® CM-5 sensor chips (GE Healthcare). All interaction studies were performed in Biacore® HSB-EP buffer with the addition of 1% (v/v) DMSO. HCAII (Sigma, lyophilized powder) was dissolved in Acetate buffer pH 5.5 to a 2 mg/mL solution. HCAII were conjugated to the surface by EDC/NHS coupling reactions in Acetate buffer pH 5.5. Solutions of the polypeptide binders were prepared in HBS-EP buffer from stock solutions of 20 µM in DMSO and allowed to flow over the surface at 20 µL/min, with blank injections after every series. All samples were adjusted to contain 1% (v/v) DMSO. Injections were made for 30 s and dissociation was allowed to proceed for 3000 s. Evaluation was performed using a 1:1 binding model.

Conjugation to Polystyrene Nanoparticles and Extraction from Blood

Pluronic F108-PDS (Allvivo Inc.) was adsorbed to polystyrene latex nanoparticles (Bangs laboratories Inc.) by incubating a 2% (w/v) suspension of particles with 10 mg/mL of Pluronic F108-PDS over night at room temperature under constant shaking. After adsorption the excess surfactant was separated from the coated particles by centrifugation at 14000 rpm for 5 minutes using an Eppendorff tabletop centrifuge. The supernatant was removed and the particles were resuspended in 10 mM Hepes buffer at pH 7.4. This washing procedure was repeated three times before addition of the cystein deprotected polypeptide conjugates as a 1 mg/mL solution in 10 mM Hepes buffer at pH 7.4. The reaction mixture was incubated under gentle shaking for 1 to 12 hours. The nanoparticles were washed three times with buffer and resuspended in 100 µL buffer. Fresh blood (drawn from one of us) was lysed by addition of the double volume of Milli-Q grade water and gently shaken for 15 minutes. The lysed blood was centrifuged and the supernatant was collected. The resuspended nanoparticles conjugated to binders were incubated with 100 to 500 µL lysate at room temperature with gentle shaking. After one hour the mixture was centrifuged and the supernatant was removed and the particles were washed with buffer three times. The binders together with their captured proteins were cleaved from the particles using 50 mM DTT in Hepes buffer pH 7.4 followed by centrifugation (14000 rpm, 5 min.) to remove the particles from the samples. Aliquots of 8 µL of the supernatants were analyzed by gradient SDS-PAGE gels electrophoresis using NuPAGE® Novex Bis-Tris 4-12% (v/w) gel and MES running buffer (Invitrogen). After electrophoresis the gels were fixed in 100 mL fixation buffer (40% ethanol, 10% acetic acid) and silver stained using the SilverQuest™ silver staining kit (Invitrogen) or fixed in 100 mL fixation buffer (35% methanol, 10% acetic acid) and stained using Colloidal Blue staining kit (Invitrogen).

Example 3

This Example is directed to the use of the molecular tool of the invention in the development of binders for phosphorylated proteins.

Protein phosphorylation plays a key role in driving and directing essential functions of life. Phosphorylation is a reversible covalent modification controlled by kinases and phosphatases and acts as a "molecular trigger" for signal transduction cascades, apoptotic progression, metabolic changes and gene expression. Whenever abnormal phosphorylation occurs, mutagenic, neuropathogenic or cancerogenic activities are initiated and kinases are important drug targets. The monitoring of phosphorylation is of vital importance to understanding many complex biological functions as well as to understanding the effect of pharmaceuticals in drug development.

Protein phosphorylation is the most extensively studied of all post-translational modifications and methods for selective detection and analysis of phosphorylated proteins are in high demand, prompted to a large extent by recent advances in phosphoproteomics. Phospho-specific antibodies are routinely used to recognize the phosphorylated epitope for immunoprecipitation or Western blotting and although antiphosphotyrosine antibodies show satisfactory efficiency antiphosphoserine and antiphosphothreonine antibodies are as a rule only moderately specific. Non-specific capturing of phosphate groups are used in combination with mass spectrometry. In immobilized metal ion chromatography, IMAC, positively charged metal ions attract negatively charged species such as phosphate groups via electrostatic interactions. Metal oxides such as $TiO_2$ are used to enrich phosphorylated proteins in complex samples prior to quantitative or qualitative analysis. Methods of indirect phosphate detection are also used where the idea is to substitute the phosphate moiety with a more stable group that is easier to detect. These methods typically require that the proteins are digested by trypsin before capture and mass spectrometric analysis.

The interest in phosphotyrosines stems from their involvement in cell signalling and therefore e.g. in cancer research but phosphoserines and phosphothreonines are approximately 2000-fold more abundant. Phosphorylation of serines and threonines occurs downstream from that of tyrosines and is of considerable interest. The relatively poor performance of anti-phosphoserine and anti-phosphothreonine antibodies suggest that there is a need for high-affinity, selective, robust and efficient binders for proteins phosphorylated at the side chains of serines and threonines to allow improved monitoring of downstream phosphorylation events. Access to powerful binders will make it possible to widen the horizons in understanding the biological functions and mechanisms of protein phosphorylation as well as developing in vitro diagnostics. To be of use as a bioanalytical tool the binder should not only exhibit specificity and high affinity but should also show long term stability under storage and physiological conditions, minimal toxicity and ease of preparation.

While it is often desirable to have access to highly specific binder molecules, a general reagent for the identification and quantification of groups of phosphorylated proteins is of considerable interest in bioanalytical applications, especially as an immobilized high-affinity reagent for enrichment of phosphorylated proteins in combination with mass spectrometry and for detection of phosphorylated proteins on electroforetic gels e.g. in Western blots. The concept behind polypeptide conjugate binder molecules is that the small molecule warhead dominates the interactions between binder and protein, and the polypeptide enhances affinity as well as selectivity, in addition to introducing the properties described above. Under the condition that the small molecule warhead is selective for a specific functional group rather than a specific protein the resulting binder molecules are expected to be capable of recognizing a large fraction of the proteins carrying such functional groups, possibly all. We have addressed the problem of group-specific recognition of phosphorylated amino acid side chains and the binding of phosphorylated proteins, and in a proof-of-principle demonstration applied the binder concept to the model proteins α-casein, β-casein and ovalbumin. For this purpose, the molecular tool of the invention has been used to prepare binder molecules by conjugating the small molecule PP1, known to bind phosphate groups.

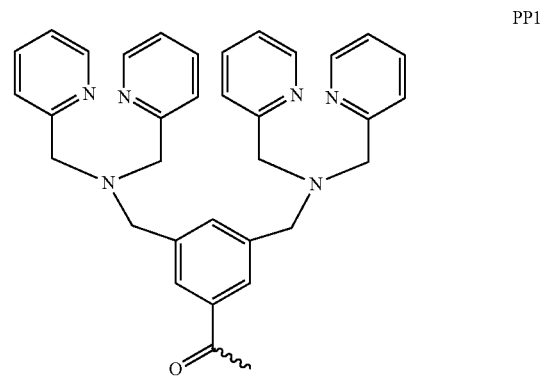

PP1

Here, the set of polypeptides used consisted of eight out of sixteen polypeptides shown in FIG. 1, viz. the polypeptides with total charges of −1 (i.e. the 3-series), and +2, (i.e. the 4-series) respectively, were used. The binders were evaluated with regard to affinity, binding mechanism and selectivity in media of variable complexity. The results suggest that these binder molecules are strong candidates for diagnostic applications in the cases where phosphorylation events play important roles.

Results and Discussion

Binder Design.

Figure 6:
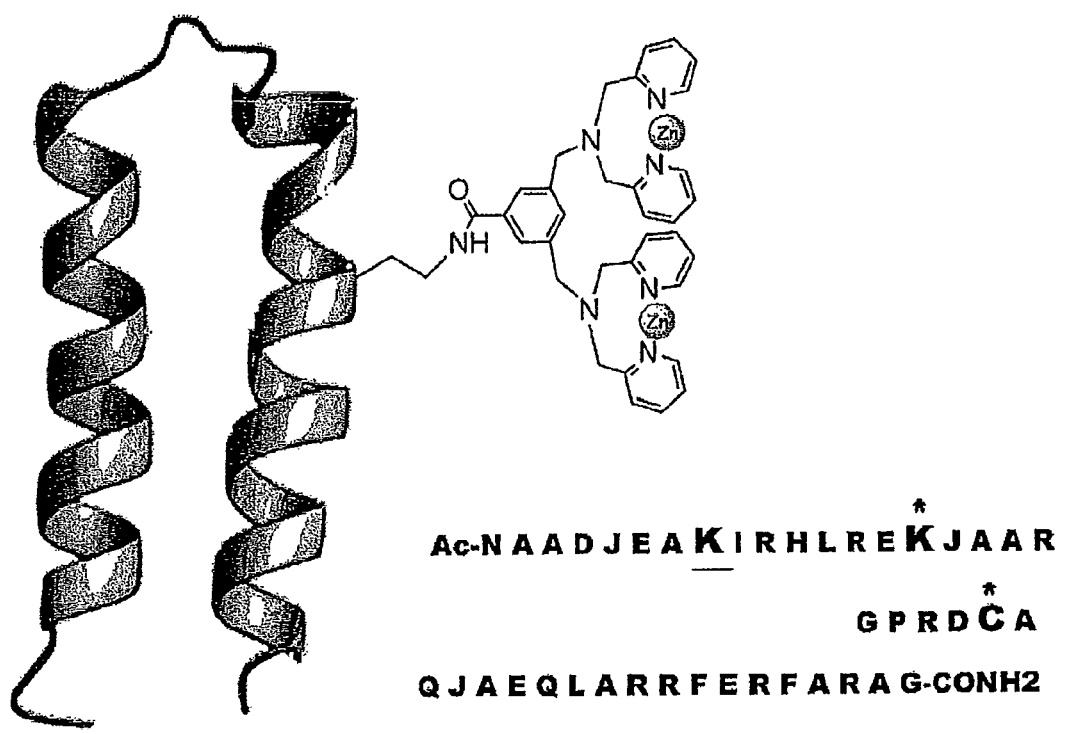
FIG. 6 shows a ligand-polypeptide of the invention, 4-C15L8-PP1 (SEQ ID NO:3), prepared in Example 3, and the amino acid sequence of the polypeptides indicating the position of zinc ions chelated by Dpa groups. The small molecule PP1 was attached to the side chain of lysine 8 (underlined). The fluorophor was attached to the side chain of lysine 15.

The lysines used as sites of attachment for the ligand and the reporter group, respectively, were protected using orthogonal protection groups. A cysteine was substituted for alanine in position 24 for immobilization or attachment of further functional groups. Modifications can be performed both on the solid phase during peptide synthesis and in solution after cleavage and purification. An illustration of the folded structure and the amino acid sequence of the binder 4-C15L8-PP1 is shown in FIG. 6.

Among many available molecules that show selectivity towards the phosphate group (Aoki, S., Kimura, E., Rev. Mol. Biotechnol. 2002, 90, 129-155) it was decided to use a Zn(II)-2,2'-dipicolylamine (Dpa) complex reported previously by Hamachi et al. to bind the phosphate anion (Ojida, A., Inoue M., Mito-oka Y., Hamachi I., J. Am. Chem. Soc. 2003, 125, 10184-10185. Ojida A., Inoue M., Mito-oka Y., Tsutsumi H., Sada K., Hamachi I., J. Am. Chem. Soc. 2006, 128, 2052-2058. Ojida A., Mito-oka Y., Sada K., Hamachi I., J. Am. Chem. Soc., 2004, 126, 2454-2463. Ishida, Y., Inoue, M., Inoue, T., Ojida, A., Hamachi, I., Chem. Commun. 2009, 2848-2850). An alternative selective phosphate recognition unit, the Phos-tag, was reported by Kinoshita et al. to have high affinity for phosphorylated peptides and proteins (Kinoshita, E., Yamada, A., Takeda, H., Kinoshita-Kikuta, E., Koike, T., J. Sep. Sci. 2005, 28, 155-162. Kinoshita, E., Takahashi, M., Takeda, H., Shiro, M., Koike T., Dalton Trans. 2004, 1189-1193. Kinoshita, E., Kinoshita-Kikuta, E., Takiyama, K., Koike T., Mol. Cell. Proteomics 2006, 5, 749-757). A molecule composed of two Dpa groups linked by dimethylbenzoic acid (PP1) was selected for binder development. It has been used previously in the construction of phosphate receptors and binds two $Zn^{2+}$ ions that coordinate to the phosphate oxygens. It has been reported to bind phosphopeptides with dissociation constants in the μM range (Yamaguchi, S., Yoshimura, I., Kohira, T., Tamaru, S., Hamachi, I., J. Am. Chem. Soc. 2005, 127, 11835-11841. Mangalum, A., Smith, R. C, Tetrahedron 2009, 65, 4298-4303).

Figure 7:
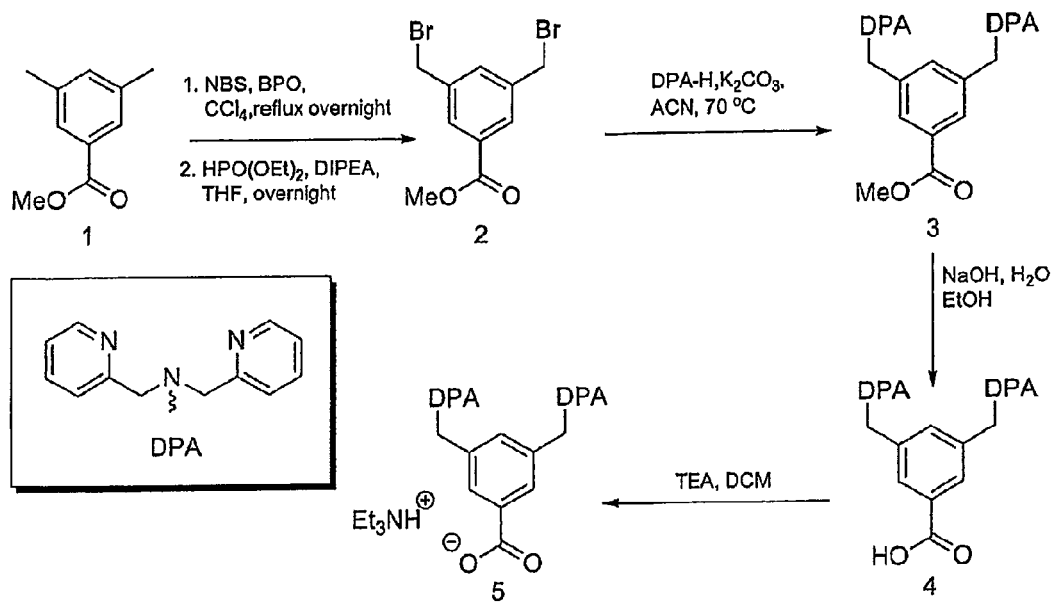
FIG. 7 schematically shows the synthesis of the phosphate binder PP1 as ligand used in Example 3.

The synthesis of PP1 is shown schematically in FIG. 7. Initially, compound 1 was subjected to radical debromination using NBS followed by treatment with diethyl phosphite in order to remove unwanted excessively brominated compounds (Liu, P., Chen, Y., Deng, J., Tu, Y., Synthesis 2001, 14, 2078-2080). Next step comprised a nucleophilic attack with Dpa-H fragments on 2 to yield compound 3 which was further hydrolyzed to form carboxylic acid 4. Due to the difficult purification of such a polar compound, the carboxylic acid 4 was purified by partitioning between water and organic phase and in the end was transformed into the corresponding TEA salt which was easy to take to the organic phase due to the hydrophobic nature of the counter ion. The above synthesis route was optimized and the target compound was produced in very good yield compared to those reported in the literature.

Phosphorylation takes place on the surface of folded proteins and in this case no spacer was included, the PP1 warhead was conjugated directly to the side chain of lysine 8.

Structural Characterization.

In order to determine whether the introduction of PP1 and $Zn^{2+}$ ions affected the solution conformation of the polypeptides the binder molecule 4-C15L8-PP1 at various stages of assembly was investigated by circular dichroism spectroscopy at 1, 10 and 50 μM concentration in 10 mM HEPES buffer at pH 7.2, Table 3.

TABLE 3

Mean residue ellipticities at 222 nm of 4-C15L8 at various stages of assembly in 10 mM HEPES buffer, 150 mM NaCl and pH 7.2 at 298 K.

| | Peptide concentration | | |
|---|---|---|---|
| | 50 μM | 10 μM | 1 μM |
| | Mean residual ellpticity $[\theta]_{222}$ [deg cm² dmol⁻¹] | | |
| 4-C15L8Cys24[a] | −13011 | −11439 | −10650 |
| 4-C15L8Cys24-PP1[b] | −12874 | −11960 | −12970 |
| 4-C15L8Cys24-PP1[c] | −13254 | −12545 | −13336 |
| 2Zn(4-C15L8Cys24-PP1)[d] | −10610 | −9013 | −8661 |

[a]4-C15L8 with Tfa amide at side chain of Lys15 and free amino group at side chain of Lys8.
[b]4-C15L8 with Tfa at side chain of Lys15 and PP1 at side chain of Lys8.
[c]4-C15L8 with 7-methoxycoumarin-3-amide at side chin of Lys15 and PP1 at side chain of Lys8.
[d]4-C15L8 with Tfa at side chain of Lys15 and $Zn^{2+}$ chelate of PP1 at side chain of Lys8.

The concentrations of peptides were estimated from weight and may be associated with large errors, but relative measurements are accurate since solutions were prepared from stock solutions. $Zn(NO_3)_2$ was added in 20% excess of peptide concentration.

All peptides showed helical signatures with minima at 209 and 222 nm suggesting that they are at least partly dimerised to form four-helix bundles at these concentrations. The parent peptide 4-C15L8 and the fully decorated 4-C15L8 carrying the $Zn^{2+}$ complex of PP1 showed a modest concentration dependence indicating a monomer-dimer equilibrium whereas 4-C15L8 functionalized with PP1 did not show concentration dependence in the absence of $Zn^{2+}$. It is concluded that regardless of modification the polypeptides fold into helix-loop-helix motifs that dimerise to four helix bundles at concentrations in the μM range, and that the solution structure is not strongly affected by the introduction of the functional groups.

Binder Affinity.

In a proof-of-concept demonstration the binding of the model proteins α-casein, β-casein and ovalbumin was studied. The most widely investigated and well characterized phosphoprotein is probably α-casein. It has between 8 and 13 phosphate groups whereas β-casein has 5 and ovalbumin one. In these proteins phosphorylation occurs at the side chain of serine. They are readily available from commercial sources and therefore suitable for systematic investigations. Both caseins and ovalbumin have isoelectric points of around 5, with an IEP of 4.6 for α-casein, 5.1 for β-casein, and 4.6 for ovalbumin.

For the determination of affinity two fluorescent probes were employed that were expected to respond with altered quantum yield upon a change of the environmental hydrophobicity resulting from binding.

Figure 8:
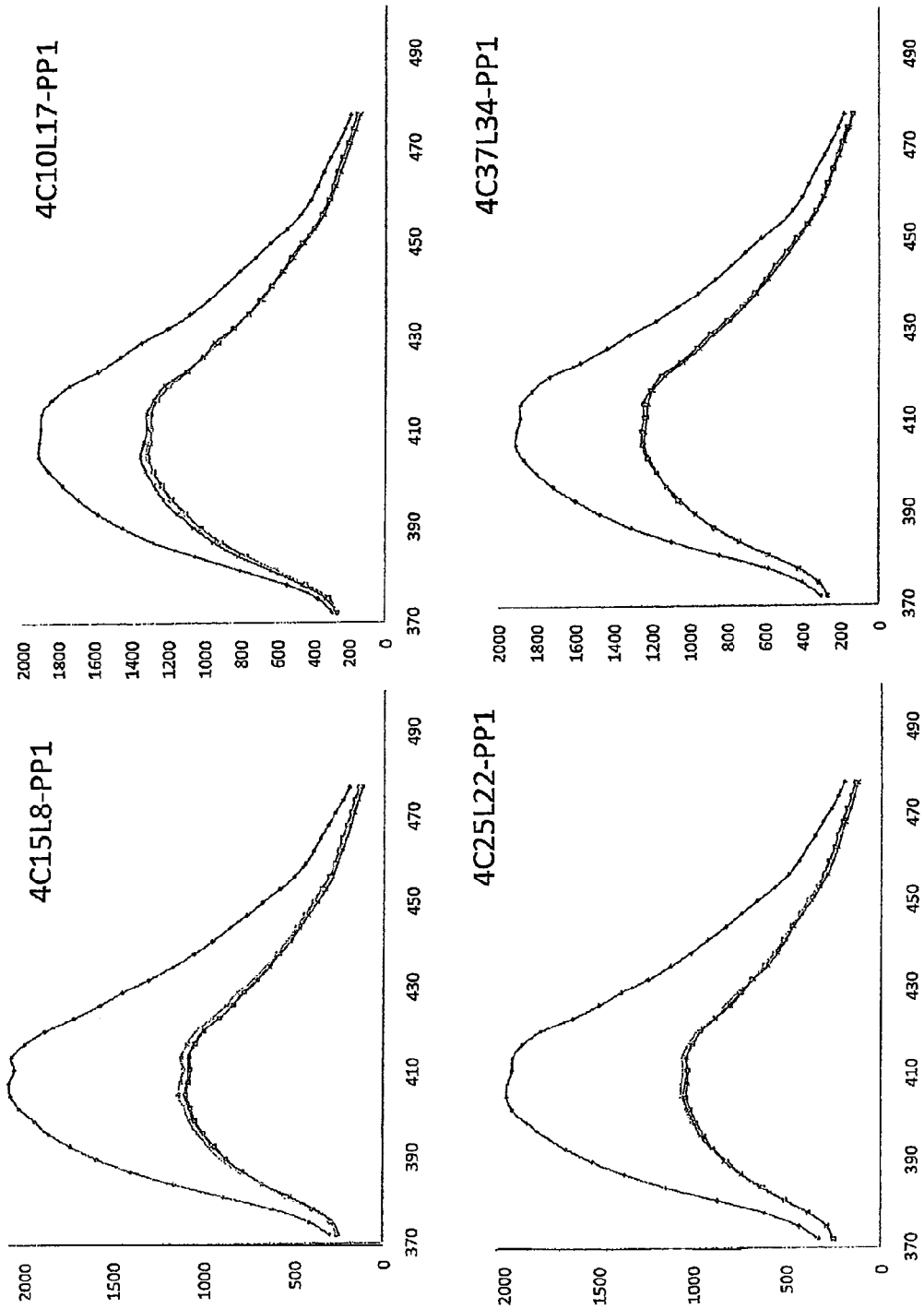
FIG. 8. Identification of high-affinity binders for α-casein from 4-series of polypeptides using three-step titration. 7-Methoxycoumarin-3-carboxylic acid was conjugated to each polypeptide to act as the fluorescence probe. Emission spectra of 500 nM binder is shown without α-casein (curves having maximum at about) 2000, and in the presence of 500 nM, 1000 nM and 1500 nM α-casein (curves having maximum at about 1000-1200). Intensity is decreased as a consequence of binding and binding is saturated at 500 nM concentration in the presence of 500 nM protein, suggesting strong binding with $K_d$ in the low nM range or lower.

In a preliminary and simple assay executable in microtitre plate format, each of the eight binder candidates at a concentration of 500 nM in 10 mM HEPES buffer and 150 mM NaCl at pH 7.2, equipped with the fluorophor 7-methoxycoumarin-3-carboxylic acid, were titrated with α-casein in three steps (FIG. 8). Concentrations of peptides were determined from the absorbance of the coumarine probe and stock solutions at concentrations of 5 μM were prepared from which aliqiuots were transferred to the microtitre plate. $Zn(NO_3)_2$ was added to a final concentration of 12 μM. The fluorescence emission spectre were recorded in the absence of protein, and in the presence of 500 nM, 1000 nM and 1500 nM protein to determine in a qualitative way whether or not binding was saturated at 500 nM concentration of both binder and protein. Saturation within experimental error at those concentrations is compatible with low nM affinity and tight binding.

The intensities of the fluorescence emission of the binders of the 4-series were found to decrease in the presence of α-casein as a result of binding, (FIG. 8). In contrast, the fluorescence emission intensities of the binders from the 3-series were found to increase in the presence of α-casein. There is no relationship between binding strength and relative change in fluorescence emission intensity as the different responses are due to differences in relative hydrophobicity surrounding the fluorophore in the bound and free states. It does not even indicate different structures of the complexes with α-casein since it could be due to different interactions within the unbound polypeptide conjugates.

Figure 9:
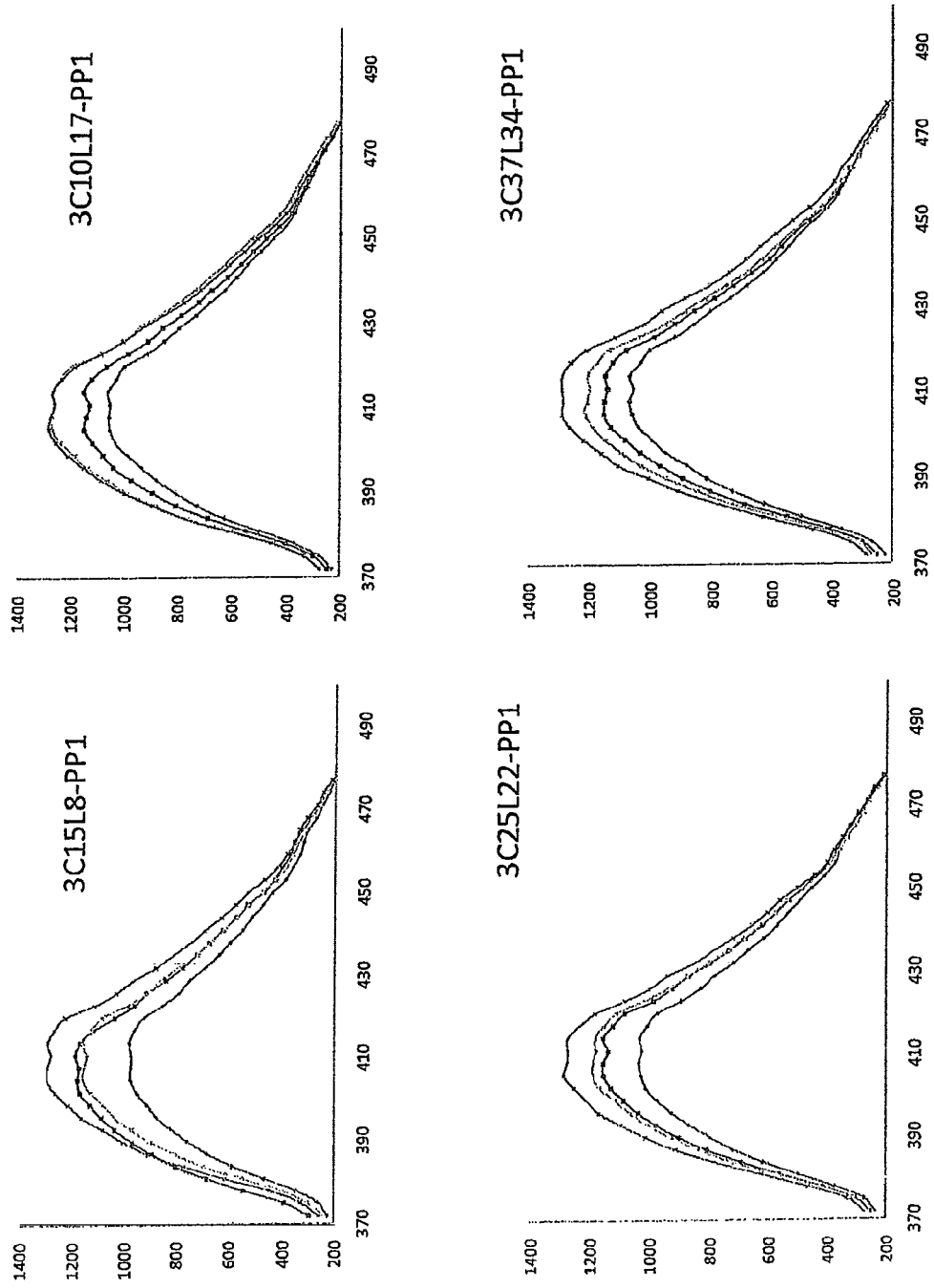
FIG. 9. Identification of high-affinity binders for α-casein from 3-series of polypeptides using three-step titration. 7-Methoxycoumarin-3-carboxylic acid was conjugated to each polypeptide to act as the fluorescence probe. Emission spectra of 500 nM binder is shown without α-casein (lowest intensity curves), and in the presence of 500 nM (intermediary intensity curves), 1000 nM (intermediary intensity curves) and 1500 nM (highest intensity curves) α-casein. Intensity is increased as a consequence of binding and binding is increased with increasing amounts of α-casein, without reaching saturation, suggesting weak binding with $K_d$ in the high nM to µM range. The binder 3-C10L17-PP1 appears to be saturated at a concentration of 1000 nM of α-casein, indicating a dissociation constant of 60 nM.

In contrast, the differences in relative responses to increased concentrations of α-casein are related to differences in affinity. The 4-series of binder molecules showed nearly identical fluorescence emission spectra regardless of the concentration of α-casein suggesting that binding is saturated at 500 nM concentration of binder and protein. Under the assumption that the experimental error is 10% or less one can estimate that the concentration of the binder-protein complex is 450 nM and the concentrations of free protein and free binder are 50 nM each. From those numbers an apparent affinity of 5 nM can be calculated. Obviously the estimate is a rough one, the experimental error is probably larger than 10%, and it only provides an upper limit to the dissociation constant (lower limit to affinity). Nevertheless, it is a quick and informative experiment. From the fluorescence titrations the 4-series of binder candidates was estimated to have dissociation constants of around 5 nM or lower. In contrast, the intensities of the 3-series binders increased with increasing α-casein concentration and did not reach saturation under the experimental conditions, with the possible exception of 3C10L17-PP1, (FIG. 9). It is concluded that the 3-series binders have dissociation constants in the high nM to the μM range. The nearly identical affinities within the 3-series and within the 4-series is probably fortuitous.

As negative controls the unmodified polypeptide 4-C17L10 and 4-C10L17-PP1 in the absence of $Zn^{2+}$ ions were titrated with α-casein (FIG. 10). No effect on the fluorescence emission spectrum was observed and PP1 as well as $Zn^{2+}$ ions are shown to be required for binding. The polypeptide affinity for α-casein is low but from the published dissociation constants of PP1 one can conclude that conjugation of the polypeptide to PP1 gives rise to a polypeptide conjugate that binds orders of magnitude better than PP1. Consequently, the polypeptide contributes significantly to binding in the conjugate as one would expect from the general binder concept.

Competition experiments were carried out in order to further probe the interactions between binder and α-casein, and analysed by pull-down experiments followed by SDS-PAGE analysis. Pluronic was adsorbed to polystyrene latex nanoparticles by incubating a 2% suspension of particles with 10 mg/mL of Pluronic F108-PDS over night at room temperature under constant shaking. The binder 4-C15L8-PP1 with a deprotected thiol was coupled via a disulfide bridge to the surface of the polystyrene particles by reaction with the immobilized Pluronic equipped with the pyridyldisulfide (PDS) end groups. Particles thus prepared were incubated in solutions of proteins and after repeated washing and centrifugation treated with DTT to release captured proteins from the beads. The resulting supernatants were applied to the gels for electroforetic analysis.

Figure 11:
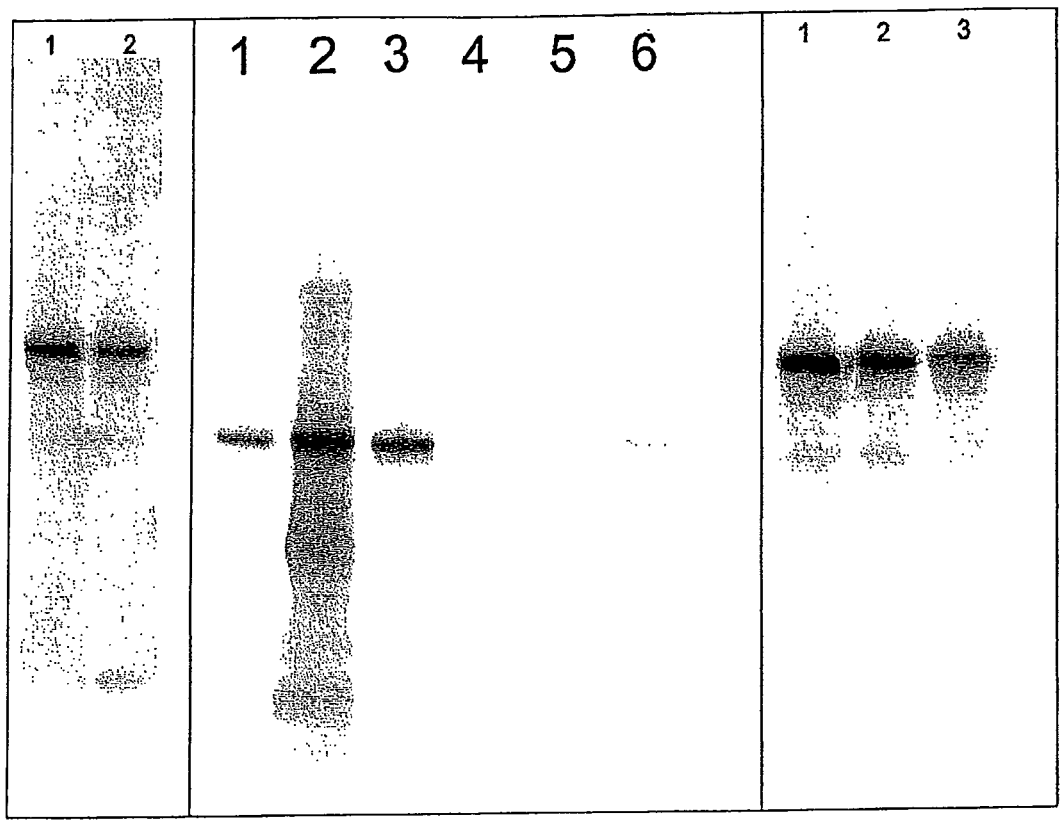
FIG. 11. Pull-down of α-casein by 4-C15L8-PP1 in competition with phosphate anion (10 mM PBS buffer, 150 mM NaCl, pH 7.2) (A) and control peptide PhosPep with one phosphotyrosine in sequence (B). Pull-down of phosphate depleted α-casein (C).

Although PP1 chelated with $Zn^{2+}$ was designed to bind phosphorylated amino acid side chains through coordination to the phosphate group, 10 mM PBS buffer corresponding to an excess of phosphate anions over phosphoserines by three orders of magnitude, did not inhibit the capture of α-casein at a protein concentration of 500 nM, FIG. 11. This opens up a wide range of applications for diagnostic purposes where the concentration of phosphate anions is high (Rapoport, S., Guest, G. M., J. Biol. Chem. 1941, 138, 269-282. Lehman, E. P., J. Biol. Chem. 1921, 48, 293-303 Gustin, P., Detry B., Cao M. L., Chenut F., Robert A., Ansay M., Frans A., Clerbaux, T., J Appl Physiol, 1994, 77, 202-208). Competition for the binder between 500 nM α-casein and a synthetic peptide with a phosphotyrosine side chain. PhosPep, at a concentration of 400 µM clearly favoured α-casein. Only when the concentration of α-casein was decreased to 100 nM and the concentration of the peptide remained at high µM level, was the binding event suppressed. Commercially available α-casein dephosphorylated to a level of 20% was also readily extracted by the binder. The results provide strong evidence that the binder provides high affinity for α-casein through synergies between polypeptide and PP1.

For a more accurate determination of the dissociation constant, titration with protein at a binder concentration of 100 nM in 10 mM HEPES buffer and 150 mM NaCl at pH 7.2 was carried out (FIG. 12). At this concentration a more strongly emitting probe was required and fluorescein was attached to the side chain of Cys-24 by reacting the maleimide group with the free thiol of the polypeptide after removal of the acetamidomethyl (Acm) protection group. The binder concentration was kept constant at 100 nM and a series of samples were prepared where only the concentration of α-casein was varied. The best fit of an equation describing the dissociation of a 1:1 complex to the experimental results gave an apparent dissociation constant of 17 nM, although a number of dissociation constants are probably involved. The description of the complex dissociation behaviour of α-casein and one or more copies of 4-C15L8-PP1 in terms of a single dissociation constant is obviously an oversimplification. It is not known how many binder molecules bind to the phosphate groups of α-casein, and it is not known if they are associated with different affinities, most likely they are.

The measured value is probably an underestimate of the true Kd. In order to obtain the most reliable value of a dissociation constant, the measurements need to be carried out at a concentration that is similar to the value of the dissociation constant. In this case it was not feasible since the changes in fluorescence emission were not strong enough to permit measurements at or below 17 nM with the required accuracy. Also the concentration of α-casein is lower than the concentration of 4-C15L8-PP1 at around the inflexion point and below, and the change in fluorescence emission therefore underestimates binding strength. The apparent dissociation constant shows that the hybrid binder molecule binds α-casein tightly and we conclude that 17 nM is an underestimate of the binder's efficiency. Unfortunately due to the practical limitations, we are unable to establish more accurate values of $K_d$.

Binder Selectivity.

The analysis of extracts from a protein mixture containing 500 nM each of α-casein and ovalbumin as well as the non-phosphorylated proteins lysozyme, phosphorylase B and b-galactosidase is shown in FIG. 13. Three negative controls were used, beads coated with Pluronic for determination of unspecific binding, beads coated with Pluronic and immobilized 4-C15L8 where the lysine at position 8 was acetylated for determination of unspecific binding to the peptide scaffold and beads coated with Pluronic and immobilized 4-C15L8-PP1 without $Zn^{2+}$ ions. To make sure that $Zn^{2+}$ ions were removed from the complex the experiment was carried out in the presence of 1 mM EDTA.

The binder 4-C15L8-PP1 extracts α-casein selectively from the mixture, with insignificant non-specific uptake although a band corresponding to the non/phosphorylated protein phosphorylase B is observed. Control experiments show that phosphorylase B binds non-specifically to the Pluronic coated bead (results not shown). An important outcome is the demonstration that zinc is essential for binding α-casein.

To evaluate binding also of phosphoproteins with a lower lever of phosphorylation than α-casein the extraction of β-casein from a 100 nM solution was demonstrated (FIG. 14). This protein has approximately half the number of phosphate groups of α-casein. The mono-phosphorylated protein ovoalbumine at 100 nM concentration could, however, not be extracted. The difference may be due to differences in affinity, since the avidity for polyphosphorylated proteins is expected to be higher than for a mono-phosphorylated one. It may also be due to less optimal interactions between polypeptide and protein, and could possibly be improved by selecting a different polypeptide.

The selectivity of 4-C15L8-PP1 in more complex media was evaluated by pull-down experiments in bovine milk and human serum (FIG. 15). Bovine milk in addition to very many other proteins, contains a number of caseins where α-casein is the most abundant. Human serum contains thousands of different proteins and extraction from human serum provides a critical evaluation of binder selectivity of relevance to the measurement of phosphorylated proteins in biomedical applications. Human serum was selected as the medium although it does not contain α-casein, which had to be added. Pull-down of α-casein from bovine milk was cleanly achieved and accompanied only by a minor band corresponding to β-casein. Pull-down of a-casein from spiked 100-fold diluted human serum was successfully demonstrated and pull-down from spiked neat human serum was successful although several bands appeared on the gel. It is not possible to avoid non-specific uptake by the beads in the complex medium of neat human serum and thus not possible to clearly define the level of selectivity of 4-C15L8-PP1 in neat serum. However, it is demonstrated that a-casein is extracted in competition with thousands of proteins by the synthetic binder molecule 4-C15L8-PP1.

The binders reported here show high affinity and selectivity for the model phosphoproteins α-casein and b-casein in buffer as well as in milk and serum and further illustrate that the set of polypeptide sequences used to develop the binders is of general applicability in developing binders for virtually any protein. The concept is different from that of biological binders such as antibodies and aptamers where highly complex and preorganized structures with high molecular weights are required and offer an alternative for capturing and detecting phosphoproteins, in solution as well as on solid support especially for monitoring phosphorylation events involving serine and threonine. This type of binder is highly suitable for a wide range of applications in biotechnology and biomedicine where robust capturing technologies are of great interest. It can be stored without special precautions at room temperature and is easily derivatized using well established chemical methods and reagents. Enrichment of biological samples prior to mass spectrometric analysis is an attractive application for this technology bearing in mind that phosphorylated proteins are less ionizable in comparison to the corresponding non-phosphorylated ones. The binder also performs very well in "pull-down" experiments and is expected to have a large number of applications in monitoring cellular phosphorylation events as a result of exposure to pharmaceuticals. We believe that the binder will be capable of acting as an imaging agent, in vitro and in vivo, due to the flexibility with which organic molecules can be covalently attached without perturbing binding performance. The possibility of conjugating fluorescent probes and radionuclides site specifically makes the technology highly flexible and adaptable. Finally it is a small binder molecule in comparison with typical antibodies.

Experimental Section
Synthesis of Small Molecules
General Information

All reagents were purchased from commercial sources and were used without further purification. For thin layer chromatography (TLC), precoated 0.25 mm silica gel and aluminum oxide plates (Merck) were used and spots were visualized with UV light ($\lambda$=254 nm). $^1$H NMR spectra were recorded on a 500 MHz (499.9 MHz) spectrometer and $^{13}$C NMR spectra were recorded on 400 MHz (100.6 MHz) spectrometer. Spectra were recorded at 25° C. using deuterated chloroform or as solvent. Chemical shifts (δ) in ppm are reported using residual chloroform as an internal reference (1H δ 7.26, 13C δ 77.0) and coupling constants (J) are reported in Hz. Low resolution mass spectra were recorded on Perkin Elmer SCIEX API 150EX spectrometer using positive ion mode.

Methyl 3,5-bis(bromomethyl)-benzoate (2)

Step 1

3,5-dimethylbenzoate (5 g, 30 mmol) was dissolved in of $CCl_4$ (50 mL) followed by addition of NBS (16.2 g, 90 mmol) and benzoyl peroxide (0.2 g, 0.8 mmol) in three equal portions during 1 h. The reaction mixture was refluxed overnight. The precipitate (succyimide) was filtered off and washed with DCM. Combined filtrates were washed with saturated solution of $NaHCO_3$ and brine. Solvent was evaporated under reduced pressure resulting a yellow oil which was used without further work-up to the next step.

Step 2

The product from Step 1 was dissolved in dry THF (20 mL), cooled to 0° C. and diethyl phosphite (12.6 g, 90 mmol) and DIPEA (11.78 g, 90 mmol) were added. The solution was gradually warmed to rt and stirring was continued overnight. The mixture was evaporated to approx half of the volume and was poured on the ice/water mixture and extracted with the $Et_2O$ (2×50 mL). The organic layer was washed with 1M HCl and brine and evaporated. Crude product which was purified by means of flash chromatography (Silica gel: AcOEt/n-pentane 1:9) resulting a white powder. Yield: 5.5 g (56%). $^1$H NMR (500 MHz, $CDCl_3$) δ 8.00 (d, J=1.7 Hz, 2H), 7.62 (s, 1H), 4.50 (s, 4H), 3.94 (s, 3H). $^{13}$C NMR (101 MHz, $CDCl_3$) δ 165.8, 138.9, 138.5, 133.7, 133.3, 131.3, 129.9, 129.5, 52.4, 45.0, 31.8, 31.8.

MS (ESI, m/z): calculated: 321.9 observed: 344.2 [M+Na]$^+$.

Methyl 3,5-bis[[bis(2-pyridylmethyl)amino]methyl]benzoate (3)

Methyl 3,5-bis(bromomethyl)-benzoate (500 mg, 1.6 mmol) and di-(2-picolyl)-amine (800 mg, 725 μL, 4 mmol) were dissolved in ACN followed by the addition of dry $K_2CO_3$ (1.1 g, 7.9 mmol). The reaction mixture was refluxed overnight under reflux condenser equipped with a $CaCl_2$ tube. The reaction mixture was filtered and filtrate was evaporated under reduced pressure. Yellow residue was purified by flash chromatography ($Al_2O_3$ neutral, firstly AcOEt was used to elute impurities and then MeOH/AcOEt=1:9 (v/v)) affording a pure product as a yellow oil. Yield: 850 mg (95%). $^1$H NMR (500 MHz, $CDCl_{33}$) δ 8.51 (m, 4H), 7.94 (d, J=1.5 Hz, 2H), 7.70 (s, 1H), 7.61 (m, 8H), 7.12 (m, 4H), 3.92 (s, 3H), 3.81 (s, 8H), 3.73 (s, 4H). $^{13}$C NMR (101 MHz, $CDCl_3$) δ 197.9, 167.1, 159.5, 148.9, 139.7, 136.2, 133.8, 130.2, 128.7, 122.8, 121.9, 60.1, 58.2, 52.0. MS (ESI, m/z): calculated: 558.7 observed: 559.5 [M+H]$^+$.

3,5-Bis[[bis(2-pyridylmethyl)amino]methyl]benzoic acid * TEA salt/PP1 (4)

Methyl 3,5-bis[[bis(2-pyridylmethyl)amino]methyl]benzoate (1 g, 1.8 mmol) was dissolved in MeOH (50 mL) and 10% solution of NaOH (5 mL) was added. The reaction mixture was refluxed for 2 h (reaction progress was monitored by TLC, $Al_2O_3$, MeOH/AcOEt 1:9 (v/v)). The reaction mixture was cooled to 0° C. followed by the addition of 10M HCl until pH=2 was reached followed by solvent evaporation under reduced pressure. Obtained yellow oily suspension was redissolved in water (50 mL) and TEA (3.6 g, 36 mmol) was added dropwise. Aqueous solution was extracted with DCM (2×50 mL) and organic layers were combined, evaporated and dried under high vacuum to obtain a product as a viscous oil. Yield: 1.1 g (95%). $^1$H NMR (500 MHz, $CDCl_3$) δ 8.50 (m, 3H), 7.99 (d, J=1.3 Hz, 2H), 7.66 (d, J=8.7 Hz, 1H), 7.59 (m, 8H), 7.11 (m, 4H), 3.82 (s, 8H), 3.70 (s, 4H), 3.06 (q, J=7.3 Hz, 6H), 1.29 (t, J=7.3 Hz, 9H). $^{13}$C NMR (101 MHz, $CDCl_3$) δ 170.2, 159.4, 148.9, 148.6, 138.8, 136.6, 136.5, 133.4, 132.7, 129.1, 122.9, 122.0, 77.3, 76.7, 60.1, 59.8, 58.5, 45.0, 8.5.

Peptide Synthesis and Post-Peptide-Synthesis Modification
General Information

The synthesis of the peptide was carried out using automated, solid-phase methodology on Applied Biosystems 433A peptide synthesizer employing standard Fmoc (9-Fluorenylmethyloxycarbonyl) chemistry using Fast Moc synthesis program. The synthesis was performed on 0.1 mmol scale and $H_2N$-RinkAmide-ChemMatrix (PCAS BioMatrix Inc) resin with a loading of 0.54 mmol $g^{-1}$ was used as a solid support. All the coupling steps were conducted with HCTU/6Cl-HOBt/DIPEA (Iris Biotech GmbH and Pepnet Inc.) activation cocktail. All reagents used in the peptide synthesis were prepared according to the manufacturer's protocols without modifications. The side chains of the amino acids (Iris Biotech GmbH and Pepnet Inc.) were protected by base-stable groups: tert-butyl ester (Asp, Glu), trityl (His, Asn, Gln) and 2,2,4,6,7-pentamethyldihydrobenzofuran-5-sulfonyl (Arg). To allow flexible orthogonality in attaching the binding subunit, fluorescent probe or attaching to the polystyrene beads backbones of Lys15 and Lys8 were protected with trifluoracetyl and 4-methyltrityl. Cys side chain was protected with acetyl-aminomethyl. HPLC purifications of the peptides were performed by HPLC (semi-preparative hypersil C-18 column 250×20 mm, 5 μm particle size) using two set of solvents: A (10% ACN/90% $H_2O$/0.1% TFA), B (90% ACN/10% $H_2O$/0.1% TFA). Details about the mobile phase composition are included in the following procedures. Identification of the peptide was done by MALDI-TOF MS (Applied Biosystems, Voyager-DE PRO) using α-cyano-4-hydroxy-cinnamic acid as a matrix. CD spectroscopy (JASCO J-810) was done at 25° C. using peptide concentrations of 50 μM to 1 μM in 5 mM HEPES buffer. The pH was set to 7.2 prior to measuring. All CD measurements were performed in 1 mm and 10 mm quartz quvettes.

Mtt Cleavage:

After the synthesis in order to deprotect Mtt on the Lys 8, peptide-containing resin was washed two times with mixture containing TFA/DCM (3:97 (v/v)) in 10 min cycles. The resin was washed with DCM and dried in vacuo.

The Incorporation of the PP1 (4) onto the Peptide Scaffold:

Approx. ¼ of the peptide-containing resin (0.025 mmol of the peptide) was immersed in NMP (1.5 mL) solution of 4 (80 mg, 0.125 mmol), PyBOP (65 mg, 0.125 mmol) and DIPEA (32 mg, 0.25 mmol) and incubated overnight. Resin was washed with DMF (3 times) and DCM (3 times). Peptide was cleaved from the resin using a mixture containing TFA/triisopropylsilane/$H_2O$ (95:2.5:2.5 v/v) for three hours and precipitated using subsequently chilled MTBE. Peptide lump was redissolved in minimal amount of TFA and precipitation was repeated using cold $Et_2O$. The peptide was dissolved in water, freeze-dried and then purified by means of HPLC using mobile phase gradient (30% B to 45% B in 17 minutes, flow: 8 mL/min).

Acm Deprotection:

The peptide (1 μmol) was dissolved in 0.50 mL of TFA containing 2% (v/v) of anisole. The solution was cooled to 0° C. and a solution of AgOTf (26 mg, 0.1 mmol, 100 equiv) in 0.5 mL TFA is added to it. The reaction mixture was stirred at 0° C. for 1 h and then allowed to attain rt. The stirring was continued for 12 hours at rt. The silver salt of the peptide was precipitated from the reaction mixture by adding cold diethyl ether and centrifuged. The supernatant solution is discarded and the residue is dissolved in 0.5 mL distilled water. A solution of DL-Dithiothreitol (8 mg, 0.05 mmol, 50 equiv) in 0.5 mL glacial acetic acid is added to the solution of the peptide. The mixture is allowed to stir for 2 h and centrifuged. The residue is discarded and the peptide contained in the supernatant is purified using Sep-Pak Plus (C-18 cartridges, Waters) and HPLC solvents A and B. The sample was diluted to 10 mL with HPLC solvent A and loaded on the SEP-PACK cartridge. The cartridge was washed with gradually increasing polarity of the mobile phase. The collected fractions were analyzed by MALDI and these containing the desired product were combined and freeze-dried.

Tfa Deprotection:

The peptide (1 μmol) was dissolved in water (1 mL) and the solution was cooled to 0° C. To the stirred solution, piperidine (200 μL, 2 mmol) was added and stirring was continued for 2 h at 0° C. The solution was neutralized by addition of cold TFA (154 μL, 2 mmol) and purified using Sep-Pak Plus (C-18 cartridges, Waters) and HPLC solvents A and B. The sample was diluted to 10 mL with HPLC solvent A and loaded on the SEP-PACK cartridge. The cartridge was washed with gradually increasing polarity of the mobile phase. The collected fractions were analyzed by MALDI and these containing the desired product were combined and freeze-dried.

Fluorescence Experiments

General Information

All fluorescence experiments were conducted in 96 well polystyrene plates. All readings were performed by plate reader Molecular Devices Spectra max GEMINI XPS at 25° C. Each plate contained 300 μL of analyte. All polystyrene plates were specially prepared prior the measurements in order to minimize the unspecific binding of the analyte. All wells were filled with 1% aqueous solution of Pluronic and left overnight. After thorough washing the wells were filled with the solution containing peptide (0.3 mg/mL) structurally similar to the peptide used in the further experiments. The plates were incubated overnight and then thoroughly washed and dried.

Preliminary Fluorescence Screening:

Three solutions were prepared: first one contained 500 nM of PP1_4-C15L8Cys24 in HEPES buffer (pH=7.2, 10 mM HEPES, 150 mM NaCl), second one contained 500 nM of PP1_4-C15L8Cys24 and 500 nM α-casein in HEPES buffer (pH=7.2, 10 mM HEPES, 150 mM NaCl), third one contained 500 nM of PP1_4-C15L8Cys24 and 1000 nM α-casein in HEPES buffer (pH=7.2, 10 mM HEPES, 150 mM NaCl). Each solution was prepared in the well just before the measurement. Each series of the three solutions was triplicated and the mean value was taken. The fluorescence of the solution containing only protein dissolved in the buffer was registered but the response was only at the noise level (not reported).

Affinity Determination with Fluorescence Spectroscopy:

A series of solutions were prepared. Each of the solutions, contained binder 4-C15L8-PP1* in concentration of 100 nM and the concentration of α-casein was varied form 1 nM up to 10 μM. All solutions were prepared in HEPES buffer (pH=7.2, 10 mM HEPES, 150 mM NaCl). The fluorescence at 525 nm was observed as a function of total protein concentration and the dissociation constant $K_d$ was determined by fitting the equation (1)

$$F_{obs} = \frac{F_{bound}[\alpha C] + F_{free} K_d}{[\alpha C] + K_d}. \quad \text{Equation 1}$$

In the Equation 1, $F_{obs}$ is the observed fluorescence intensity, $F_{bound}$ is the fluorescence of the peptide-binder bound to the α-casein, $F_{free}$ is the fluorescence of the free peptide and $[\alpha C]$ is the concentration of the free α-casein. $[\alpha C]$ can be derived from the Equation 2, where $[P]_{tot}$ is the total concentration of peptide and $[\alpha C_{tot}]$ is the total concentration of the α-casein.

$$[\alpha C] = -\frac{[P]_{tot} + K_d - [\alpha C]_{tot}}{2} + \sqrt{\left(\frac{[P]_{tot} + K_d - [\alpha C]_{tot}}{2}\right)^2 + K_d[\alpha C]_{tot}}.$$ Equation 2

Numerical fitting was done with IGOR Pro 4.03 (WaveMetrics Inc.).

Pull-Down Experiments and Fluorescence Experiments
General Information:

Polystyrene Beads (nominal diameter: 1 µm) were purchased as a suspension in water from Bangs Laboratories, Inc. Pluronic was purchased from BASF and Pluronic F108-PDS was supplied by Allvivo Inc. (Lake Forest, Calif., USA). All proteins were purchased form Sigma Aldrich. All reagents and gels used for gel electrophoresis were from Invitrogen. SDS-PAGE electrophoresis was conducted using NuPAGE® Novex 4-12% Bis-Tris Gel 1.5 mm. Gel development was conducted in MES buffer. All gels were stained using silver staining kit SilverQuest™ kit.

Pluronic adsorption to the polystyrene particles: Polystyrene Beads (1 µm, 10 mg) were washed once with miliQ-water and then centerfuged (14,000 rpm for 7 min). The particles were resuspended in aqueous solution of F108-PDS (1 mL, 2%) and shaken end-over-end for 24 h. Pluronic-coated particles were then separated from the excess of surfactants by means of centrifugation (14,000 rpm for 7 min). Beads were subsequently resuspended in HEPES buffer (pH=7.2, 10 mM HEPES, 150 mM NaCl, 1 mM EDTA), sonicated and centrifuged again. The procedure was repeated three times.

Polypeptide Immobilization on the Polystyrene Beads:

Pluronic-PDS-coated Polystyrene Beads (1 µm, 10 mg) were washed with HEPES buffer (pH=7.2, 10 mM HEPES, 150 mM NaCl, 1 mM EDTA) purged with nitrogen. Thereafter beads were immersed in 1 mL solution containing peptide with free cysteine (0.5 mg) dissolved in nitrogen saturated aqueous solution of HEPES buffer (pH=7.2, 10 mM HEPES, 150 mM NaCl, 1 mM EDTA). All manipulations were conducted under oxygen-free conditions. After incubation for 12 h beads were washed with aqueous solution of HEPES buffer (pH=7.2, 10 mM HEPES, 150 mM NaCl) (three times) followed by washing with aqueous solution of TRIS buffer (pH=8) containing Zn ions (pH=8.2, 10 mM TRIS, 5 mM Zn(NO$_3$)$_2$). The beads were washed and resuspended in HEPES buffer (pH=7.2, 10 mM HEPES, 150 mM NaCl).

Pull-Down Experiments:

Polystyrene beads coated as described above (0.5 mg-1 mg) were incubated with buffer, milk or serum (0.5 mL-1 mL). The suspension was shaken end-over-end for 90 min and centrifuged (14,000 rpm for 7 min). The bead lump was washed at least 4 times by means of sequential resuspension in 1 mL of HEPES buffer (pH=7.2, 10 mM HEPES, 150 mM NaCl), and centrifugation (14,000 rpm for 7 min). In between the washing procedure an occasional sonication was conducted in order to diminish unspecific binding to the surface. After the washing procedure, the beads were centrifuged and the lump was resuspended in the DTT solution (1 mM in HEPES buffer (pH=7.2, 10 mM HEPES, 150 mM NaCl) (20 µL) and incubated for 1 h with occasional sonication. Thereafter, a suspension was centrifuged and supernatant was analyzed by SDS-PAGE and stained using Silver Staining. Samples for gel electrophoresis were prepared according to the manufacturer instructions.

Example 4

In Example 4, the selected target molecule was thymidine kinase (TK).

TK is responsible for the phosphorylation of 2-deoxythymidine to 5'-monophosphate-2'-deoxythymidine. An insight into the binding pocket of TK from Ureaplasma urealyticum is given in FIG. 16.

Higher organisms have two isozymes, that are chemically very different, TK1 and TK2. TK1 is present in the cytoplasm only in anticipation of cell division, whereas TK2 is located in mitochondria and is cell cycle-independent.

TK1 levels are increased in poorly differentiated and highly proliferating cells (e.g. cancer cells). TK1 has thus been an attractive target for anti-cancer drug design as well as for diagnostic applications. Tight TK1 binders that are furthermore able to discriminate between TK1 forms of different species (e.g. between human TK1 and bacterial) are of great interest.

Nucleosides are glycosylamines consisting of a nucleobase bound to a ribose or deoxyribose sugar (FIG. 17). Most importantly they serve as building blocks for DNA and RNA strands. They are furthermore involved in a number of cellular processes in the different forms of mono-, di-, or triphosphates.

A binder for thymidine kinases was synthesized from deoxy-thymidine as illustrated in Scheme 3.

Scheme 3:

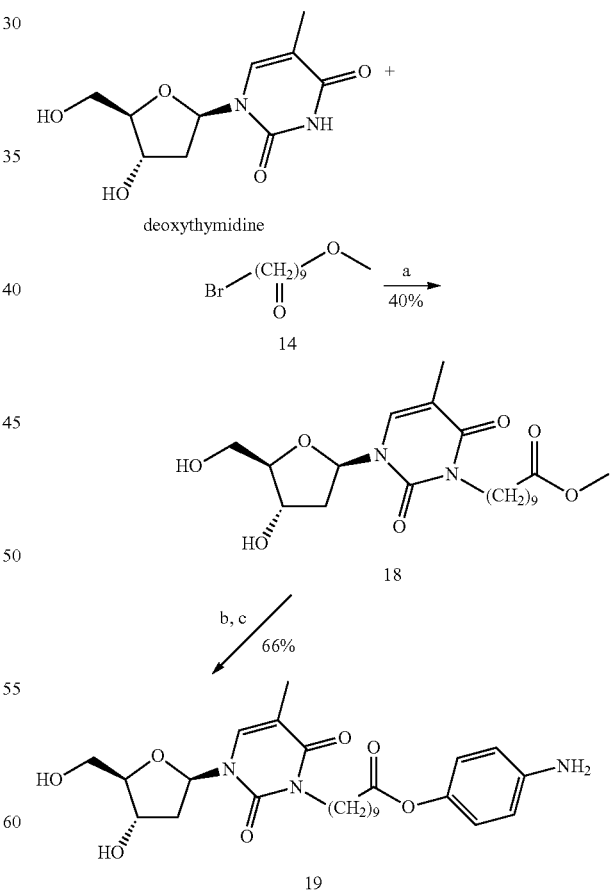

Conditions: a: 14 (1.5 eq.), NaH (1.5 eq.) DMF, rt, 20 h, b: 1M NaOH MeOH/H$_2$O, 0° C., 1 h. c: p-nitrophenol (2.5 eq.), DIPCDI (3 eq.), pyridine, rt, 2 h.

10-Bromodecanoic acid methyl ester was coupled to the N³-position of the nucleobase using again sodium hydride conditions in moderate yield. TLC reveals that the linker also attaches to other positions, though as minor by-products. The structure of 18 was verified by a COSY NMR experiment (see Experimental Part). Subsequent saponification and introduction of the p-nitrophenol yielded the deoxy-thymidine probe 19 in good yield.

In order to study thymidine kinase (TK) the deoxy-thymidine (dT) probe 19 was conjugated to 2D10L17 in a test study and HPLC showed approximately 80% conversion to the desired conjugate after 2 hours. For a quick-screening experiment dT was conjugated to eight (Table 4) of the library peptides in Tris-buffer and for 3 hours (see Experimental Part for details).

TABLE 4

The polypeptides used in the screening are written in bold.

| 1-C15L8 | 2-C15L8 | 3-C15L8 | 4-C15L8 |
|---|---|---|---|
| 1-C10L17 | 2-C10L17 | 3-C10L17 | 4-C10L17 |
| 1-C25L22 | 2-C25L22 | 3-C25L22 | 4-C25L22 |
| 1-C37L34 | 2-C37L34 | 3-C37L34 | 4-C37L34 |

Fluorescence Binding Studies with TK

Estimating that at least 60% of the peptides were then bearing the ligand, the solution was diluted to 2 μM concentration and the protein TK was added. The fluorescence response was screened after 15 min, 45 min, 2 hrs, and 20 hrs. A maximal response was seen after 2 hours of incubation time.

The four peptides 3-C15L8-dT, 2-C10L17-dT, 4-C10L17-dT and 3-C25L22-dT were identified as "hits" as addition of a second equivalent of TK led to no further increase in fluorescence intensity. The $K_d$ is estimated to be 20 nM or less.

The other four screened peptides 4-C15L8-dT, 3-C10L17-dT, 4-C25L22-dT and 2-C37L34-dT showed an increase in intensity when two equivalents of TK was present compared to no TK or one equivalent of TK and are therefore not considered to be tight binders.

Binding Studies with TK in the Presence of ATP

The fluorescence intensities were measured in presence of 1, 2 and 3 eq. TK in buffer with and without ATP. The introduction of ATP represents a realistic measurement situation as it is present in biological samples and is likely to react with the probe in the presence of TK. Data were collected 15 min, 45 min and 2 hrs after adding the enzyme. The samples for MALDI-TOF were collected appr. 5 mins, 45 mins and 2 hours after adding the enzyme to measure the change in masses.

3-C15L8-dT

Intensities for 3-C15L8-dT in the presence of ATP are higher than without ATP. The peptide was found by MALDI-TOF mass spectrometry to be fully phosphorylated after 45 minutes when ATP is present whereas the mass analysis showed a large peak for non-phosphorylated peptide after 5-10 minutes. The actual binder is therefore the phosphorylated form of 3-C15L8-dT. Binding affinity is good but not as good as for 4-C10L17-dT. See FIGS. 18 and 19.

4-C10L17-dT

Intensities for 4-C10L17-dT in the presence of ATP differed greatly from those without ATP. In the presence of ATP, similar intensities in all TK concentrations show full saturation levels. The mass analysis showed a large peak for phosphorylated dT-binder and a smaller peak for non-phosphorylated peptide after 5-10 minutes, and after 45 minutes essentially only phosphorylated binder existed. The results indicate strong binding affinity of phosphorylated 4-C10L17-dT to TK. The fluorescence spectra for 4-C10L17-dT are shown in FIGS. 20 and 21.

4-C25L22-dT

The difference in the intensity of 4-C25L22-dT regardless of whether ATP is present suggests generally good binding affinity to TK. However, the intensities vary between different TK concentrations giving the highest value in 1 eq. of TK. In the presence of ATP, the peptide was found to be fully phosphorylated after 5-10 minutes, which was the fastest phosphorylation rate but no large differences in intensities were observed during the measurements. The fluorescence spectra for 4-C25L22-dT are shown in FIGS. 22 and 23.

Competition Experiments with dT on the "Good" Binders

In a follow-up experiment to the fluorescence-screen, we tried to out-compete the peptide-binder with the natural substrate of TK, namely deoxy-thymidine (dT). For this purpose two assays were done in which 1, 10, 100, and 1000 equivalents of dT were added to the mixture relative to the peptide binder. In Assay I, the protein was first incubated with the "good" peptide binders for 1 hour then the dT was added. There was no decrease observed in fluorescence in any of the cases, indicating, that the peptide-binder can not be outcompeted with dT. In Assay II, the protein was incubated with different concentrations of dT first, then the binder-peptides were added. Immediately, a fluorescence change was observed, again indicating, that the peptide-probe conjugate binds tighter to TK than dT.

In FIGS. 24, 25, 26 and 27 the fluorescence spectra are depicted from both assay I and assay II. The blue curves represent the fluorescent extinction of the peptides containing deoxy-thymidine, the pink curves correspond to the fluorescent extinction measured for the peptide-dT conjugate with one equivalent of TK. Green curves are the results from assay I while or angle curves are the results from assay II.

Experimental Part

General

Instrumentation

Chromatography

Thin Layer Chromatography (TLC):

Silica gel thin layer chromatography was performed using Silica gel (fluorescence indicator at 254 nm, 0.2 mm layer aluminum cards) form Fluka. Visualization was done by UV light (254 nm) and/or staining the plates with anisaldehyde (10 ml p-anisaldehyde, 10 ml $H_2SO_4$ conc., 2 ml acetic acid conc., 180 ml ethanol).

Flash Chromatography (FC):

Flash chromatography (FC) was performed using silica gel (Matrex silica gel 60 Å, 35-70 μm Amicon).

High Performance Liquid Chromatography (HPLC):

HPLC purification of oligonucleotides was performed on an Varian ProStar system using analytical and/or preparative C-18 columns for reversed phase. Solvent A: 90% $H_2O$+10% ACN+0.1% TFA. Solvent B: 90% ACN+10% $H_2O$+0.1% TFA.

NMR Spectroscopy

All NMR spectra were measured at room temperature on a Varian Unity 400 MHz spectrometer. Chemical shifts (δ) are reported in ppm relative to the undeuterated residual solvent peak (7.27 ppm for $CHCl_3$, 3.35 ppm for $CHD_2OD$ and to 2.49 ppm for $d_6$-DMSO). Coupling constants J are given in Hz. Multiplicities are abbreviated as follows: s=singlet, d=doublet, t=triplet, q=quartet, m=multiplet, br=broad.

Signal assignments were done by COSY experiments.

$^{13}C$ NMR spectra were recorded at 101 MHz. Chemical shifts (δ) are reported in ppm relative to the middle solvent peak (77.0 ppm for $CDCl_3$).

Mass Spectrometry

Electrospray ionization mass spectra (ESI) were recorded on a Perkin Elmer API 150 EX machine.

MALDI-TOF-MS

MALDI-TOF-MS spectra of the peptides were recorded on a Voyager-DE PRO system by Applied Biosystems.

Fluorescence Spectroscopy

Fluorescence measurements were carried out using a GeminiXPS platereader and NUNC™ polystyrene 96- or 384 well plates. The plates were coated with Pluronic® F108NF Prill Poloxamer338 (BASF) before use.

SDS-PAGE

SDS-PAGE Gel electrophoresis was done using a NuPAGE MES-SDS-Kit from Invitrogen. The gel was stained using SilverQuest Silverstaining Kit Version F, Invitrogen.

Reactions, Chemicals, Peptides and Proteins

All reactions were performed in heated glassware under $N_2$. Solvent concentrations were performed at reduced pressure (bath temperature <40° C.). Solvents for reactions were purchased as crown cap—bottles from Aldrich (DMSO, DMF, pyridine). Solvents for extractions and FC were distilled before use. All chemicals were purchased from Aldrich (highest quality available).

$N^3$-decanoicacid-methylester-2'-deoxythymidine 18

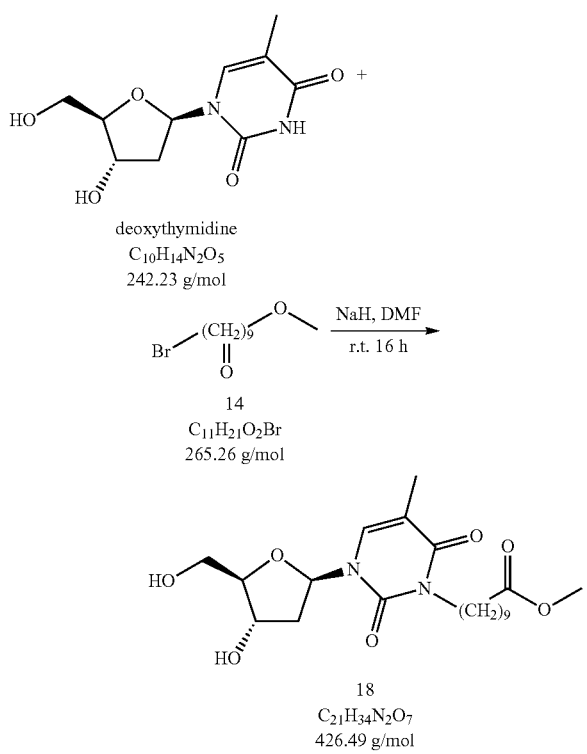

2'-deoxythymidine (500 mg, 2.06 mmol) and the bromodecanoicacid methyl ester 14 (800 mg, 3.09 mmol, 1.5 eq.) were dissolved in anhydrous DMF (5 ml) and cooled to 0° C. NaH (50-60% in oil, 148.6 mg, 3.09 mmol, 1.5 eq.) was slowly added. The suspension was stirred under $N_2$ and at 0° C. for 15 min, then allowed to warm to rt. The reaction was quenched after 16 h by the addition of sat. brine. The aqueous phase was extracted with EtOAc (3×) and the organic phase was then dried over $MgSO_4$, filtered, and concentrated. Purification by FC (silica gel, pure $CH_2Cl_2$ to 93:7 $CH_2Cl_2$/MeOH) yielded the title compound 18 (colourless oil, 358.1 mg, 0.84 mmol, 40.7%) as the major product.

TLC (silica gel, 97:3 $CH_2Cl_2$/MeOH): $R_f$ 0.21.

LR-ESI$^+$-TOF-MS (methanol): calc. for $C_{21}H_{34}O_7N_2Na$: 449.49. found: 449.0.

$^1$H-NMR (400 MHz, DMSO-$d_6$, δ(ppm)): 7.75 (s, 1H, H—C(6)), 6.20 (t, 1H, J=6.6, H—C(1')), 5.21 (d, br, 1H, J=4.0, OH—C(3')), 5.01 (t, br, 1H, J=4.8, OH—C(5')), 4.24 (m, 1H, H—C(3')), 3.76 (m, 2H, —$CH_2$), 3.58 (m, 2H, H—C(5')), 3.56 (s, 3H, —$OCH_3$), 2.26 (t, 2H, J=7.0, —$CH_2$), 2.01 (t, 2H, J=5.8, H—C(2')), 1.81 (s, 3H, —C(5)-$CH_3$), 1.48 (d, 4H, J=6.8, 2× —$CH_2$), 1.23 (s, 10H, 5× —$CH_2$).

$^{13}$C-NMR (101 MHz, DMSO-$d_6$, δ (ppm)): 173.1, 162.4, 150.2, 134.5, 108.3, 87.2, 84.6, 70.1, 61.1, 50.9, 33.1, 28.4, 26.8, 26.1, 24.2, 12.7.

$N^3$-decanoicacid-p-nitrophenyl ester-2'-deoxythymidine 19

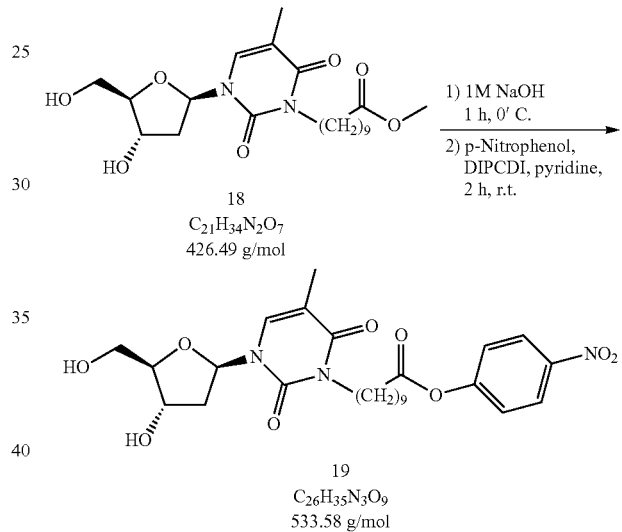

2'-deoxythymidine-derivative 18 (260 mg, 0.61 mmol) was dissolved in 1 M NaOH (2 ml, 1:1 $H_2O$/MeOH) and stirred at 0° C. for 1 h. The solution was then neutralized by the addition of 1.25 M HCl-solution (in MeOH) until pH 5 was reached. The solvents were evaporated (do not heat over 25° C.) and the remains were lyophilized over night. The residue was taken up in anh. pyridine (3 ml) and p-nitrophenol (212.3 mg, 1.53 mmol, 2.5 eq.) and diisopropylcarbodiimide (0.28 ml, 1.83 mmol, 3 eq.) were added. The yellow solution was stirred under $N_2$ and at rt for 2 h then quenched by the addition of brine. Extraction with $CH_2Cl_2$ followed by drying the organic phase over $MgSO_4$, filtration and concentration yielded the crude product. Purification by FC (silica gel, $CH_2Cl_2$ to 90:10 $CH_2Cl_2$/MeOH) yielded the title compound 19 (213.4 mg, 0.400 mmol, 65.6%) as yellow oil.

TLC (silica gel, 97:3 $CH_2Cl_2$/MeOH): $R_f$ 0.12.

LR-ESI$^+$-TOF-MS (methanol): calc. for $C_{26}H_{35}O_9N_3Na$: 556.58. found: 556.4.

$^1$H-NMR (400 MHz, CDCl$_3$, δ(ppm)): 8.27 (d, 2H, J=8.8, p-nitrophenol), 7.30 (m, 2H, p-nitrophenol), 7.29 (s, 1H, H—C(6)), 6.17 (dt, 1H, J=6.8, 3.6, H—C(1')), 4.60 (m, 1H), 4.01 (m, 1H), 3.92 (m, 2H), 3.66 (m, 2H, —$CH_2$), 2.59 (t, 1H, J=7.2), 2.44 (t, 2H, J=6.8), 2.30 (t, 3H, J=7.2, H—C(2')), 1.93 (s, 3H, —C(5)-CH$_3$), 1.76 (t, 2H, J=6.8, —CH$_2$), 1.23 (m, 10H, 5× —CH$_2$).

Conjugation of Nucleoside-Probe to Peptide Scaffold

General Procedure for dT-Binder Coupling in DMSO

The polypeptides (3 mg, 0.52 mmol) were dissolved in DMSO (1 ml) containing 10% pyridine and the AMP- or dT-binder (3 eq.) was added. DIPEA (3 µl) was added and the solution was stirred at rt for 4-20 h. The reaction was monitored by analytical HPLC. The reaction was stopped by slow addition of cold diethyl ether. After spinning down, the precipitated peptide was dissolved in water (containing 0.01% TFA), then lyophilized. The crude peptide was purified by semi-preparative HPLC to yield approximately 2 mg of the target peptide. The purified fractions were analyzed by MALDI-TOF-MS.

Analytical HPLC: C-18 column, 10-60% B in 30 min or 20-80% B in 40 min.

Preparative HPLC: semi-prep C-18 column, 10-50% B in 40 min, or 20-90% B in 40 min.

General Procedure for Acm Deprotection

Silver triflate (100 eq) was dissolved in TFA/anisole (99:1) and 1 ml was added to the acm-protected polypeptides at 0° C. The reaction was allowed to warm to rt after 2 h and then stirred overnight. The peptide was precipitated with cold diethyl ether, centrifuged and decanted. The silversalt was taken up in 50% (v/v) acetic acid together with DTT (50 eq) and stirred at rt overnight. The acm-deprotected peptide was lyophilized and purified by HPLC (10-70% B in 30 min.).

General Procedure for dT-Binder Coupling in Buffer

The polypeptides (0.5 mg, 0.1 mmol) were dissolved in Tris-buffer (see 0, 97.5 µl) to a concentration of 1 mM and the AMP- or dT-binder (2 eq.) and DIPEA (0.5 µl) were added. Probes for fluorescence screening were taken after 2 to 4 h.

Fluorescence-Experiments

Binding Studies with TK

A NUNC™ polystyrene 384 well plate (100 µl-volume) and pipette-tips were coated with Pluronic® overnight, then washed with H$_2$O and dried. The fluorescence-measurement was carried out in Tris-buffers (Buffer for TK-studies: 20 mM Tris/HCl, 0.4 M NaCl, 0.3 M imidazole, 2 mM DTT, 50% glycerol, pH 7.6). Assuming that at least 60% of the dT-binder was conjugated to the polypeptides (see 0), stock-solutions were prepared with a concentration of 60 µM. The concentration of the TK stock solution was 0.10 mM. A polypeptide concentration of 2 µM in 95 ml was used. The protein was added to wells containing the peptide conjugates to give final TK concentrations of 2 or 4 µM. Fluorescence intensities of protein-binder mixtures were compared to intensities of binders without protein and a significant change in fluorescence intensity in the presence of one equivalent of protein, in comparison to that of binder without protein, was interpreted as complexation of target protein by the binder. Binders showing a change in intensity in the presence of 2 µM protein but no further change in intensity in the presence of 4 µM protein were considered "hits". Assuming that more than 90% of the binder is complexed at 2 µM concentration of the protein the $K_d$ is estimated to be 20 nM or less ($K_d$=[P][B]/[PB]).

The dansyl probe was excited at 335 nm and emission was recorded 420-600 nm. All measurements were performed at room temperature and were made in triplicates. The wells were read after 15 min, 45 min and 2 hours.

Pull-Down Experiment

Polystyrene latex nanoparticles (0.96 µM, Bangs laboratories Inc.) were washed with 1 ml MQ three times then incubated with Pluronic F108-PDS (Allvivo Inc.) overnight and at room temperature under constant shaking. After adsorption the excess surfactant was separated from the coated particles by centrifugation at 14000 rpm for 10 min. The beads were then washed with 300 µl of MQ, followed by washing twice with 300 µl HEPES-buffer 1 (10 mM HEPES, 10 mM KCl, 1 mM EDTA, pH 7.9). The beads were then taken up in 300 µl HEPES-buffer 1 and the acm-deprotected polypeptide 2-C10L17-AMP (approx 25 µg) was added and let to react for 1 h. After spinning down, the beads were washed three times with HEPES-buffer 2 (10 mM HEPES, 10 mM KCl, pH 7.9). The blocking peptide (100 µl, 0.4 mg/ml, 4-C15L8 K24 Tfa) was added and incubated for 1 h. After spinning down and washing three times in 200 µl of HEPES 2, the beads were taken up in 200 µl HEPES 2. Nuclear—resp. cytosolic HeLa-extract (BIOTECH) (150 µl) was added the beads were incubated for 1 h. The beads were spun down and washed 6 times with HEPES 2 (300 µl each), then resuspended in 100 mM DTT (100 µl) and incubated for 20 min to cleave the polypeptide-protein conjugates. The beads were spun down at 14000 rpm for 10 min and the supernant was collected (K. Fromell, Hulting G., Ilichev A., Larsson A., Caldwell K. D., *Anal. Chem.* 2007, 79, 86019). The samples were analyzed py SDS-PAGE loading 5 µl of the sample buffer and 15 µl of the probes to the wells. The gel was run for 35 min at 200 V.

Example 5

In this Example, Vitamin D binding protein was used as target molecule.

The vitamin D family of molecules is associated with the regulation of calcium and phosphorous metabolism in higher organisms, and various vitamin D derivatives have been shown to affect disease conditions such as rickets, osteoporosis, breast cancer, prostate cancer, psoriasis, and Alzheimers disease. The influences of vitamin D derivatives on these and other diseases have spurred a wide range of research efforts where a large number of vitamin D derivatives have been synthesized and biologically evaluated. Biological evaluations of vitamin D derivatives have involved both in vivo and in vitro studies, the latter often investigating the ability of various vitamin D derivatives to bind to receptor proteins. Two extensively studied such receptor proteins are the vitamin D receptor (VDR) and the vitamin D binding protein (DBP). The latter is the major carrier of vitamin D and its metabolites in serum, and as such it is an important regulator of vitamin D levels in the body. Considering the importance of vitamin D in health and disease, it is not surprising that abnormal serum DBP levels have been correlated to disease conditions (Finehout, E. J.; Franck, Z.; Choe, L. H.; Relkin, N.; Lee, K. H. Ann Neurol 2007, 61, 120-129. Zhang, J.; Sokal, I.; Peskind, E. R.; Quinn, J. F.; Jankovic, J.; Kenney, C.; Chung, K. A.; Millard, S. P.; Nutt, J. G.; Montine, T. J. Am. J Clin Pathol 2008, 129, 526-529. Liu, X.-D.; Zeng, B.-F.; Xu, J.-G.; Zhu, H.-B.; Xia, Q.-C. Proteomics 2006, 6, 1019-1028). It would be highly interesting to use DBP levels in body fluids as biomarker for Alzheimers disease, ALS, and Parkinsons disease. Accurate and fast measurement of DBP is then an essential requirement, and in one application of the molecular tool of the present invention, peptide conjugates of vitamin D derivatives that could potentially, by way of their increased binding strength and multifunctionality are provided. It is contemplated that the polypeptide conjugates thus provided will be important tools in measurements of DBP levels in body fluids as biomarker for Alzheimers disease, ALS, and Parkinsons disease and for any other disorder connected to the DBP level in body fluids.

The synthesis of the small molecule ligand equipped with a spacer has been published, recently (Q.; Zhang, T.; Norberg, J.; Bergquist, L.; Baltzer. Tetrahedron 2010, 66, 4577-4586). The synthesis route to the most successful small molecule ligand 25OHVD₃ (i.e. Vitamin D hydroxylated on carbon atom 25) is outlined in Scheme 4

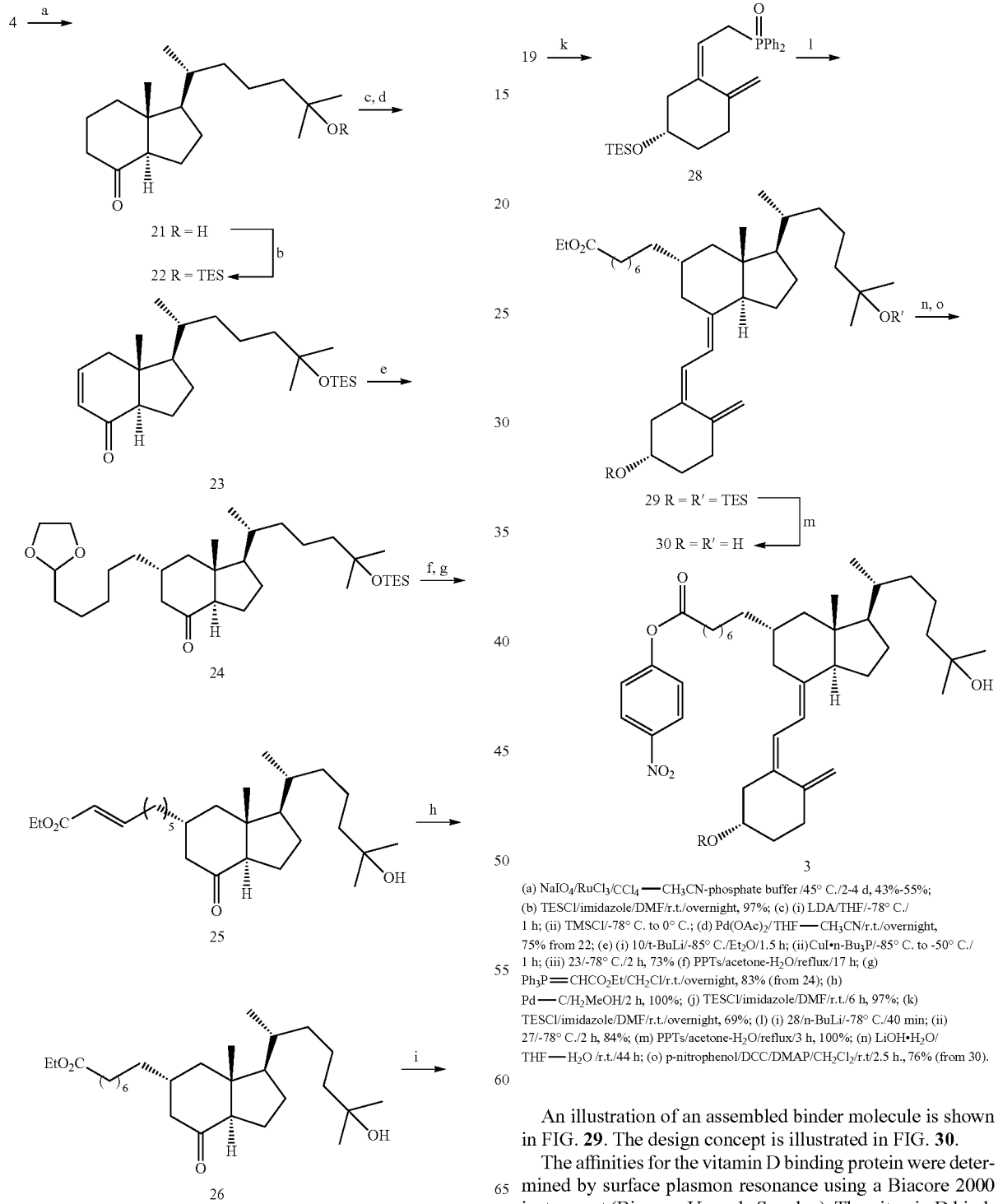

(a) NaIO₄/RuCl₃/CCl₄—CH₃CN-phosphate buffer /45° C./2-4 d, 43%-55%;
(b) TESCl/imidazole/DMF/r.t./overnight, 97%; (c) (i) LDA/THF/-78° C./1 h; (ii) TMSCl/-78° C. to 0° C.; (d) Pd(OAc)₂/ THF—CH₃CN/r.t./overnight, 75% from 22; (e) (i) 10/t-BuLi/-85° C./Et₂O/1.5 h; (ii) CuI•n-Bu₃P/-85° C. to -50° C./1 h; (iii) 23/-78° C./2 h, 73% (f) PPTs/acetone-H₂O/reflux/17 h; (g) Ph₃P=CHCO₂Et/CH₂Cl/r.t./overnight, 83% (from 24); (h) Pd—C/H₂MeOH/2 h, 100%; (j) TESCl/imidazole/DMF/r.t./6 h, 97%; (k) TESCl/imidazole/DMF/r.t./overnight, 69%; (l) (i) 28/n-BuLi/-78° C./40 min; (ii) 27/-78° C./2 h, 84%; (m) PPTs/acetone-H₂O/reflux/3 h, 100%; (n) LiOH•H₂O/ THF—H₂O /r.t./44 h; (o) p-nitrophenol/DCC/DMAP/CH₂Cl₂/r.t/2.5 h., 76% (from 30).

An illustration of an assembled binder molecule is shown in FIG. 29. The design concept is illustrated in FIG. 30.

The affinities for the vitamin D binding protein were determined by surface plasmon resonance using a Biacore 2000 instrument (Biacore, Uppsala Sweden). The vitamin D binding protein was immobilized by amine coupling to the surface of a CM5 sensor chip (Biacore). Immobilization and interaction studies were conducted at 25° C. in 10 mM Hepes buffer at pH 7.4, containing 150 mM NaCl, 3 mM EDTA, and 0.005% surfactant P20 (polyoxyethylenesorbitan) (HBS-EP buffer, Biacore) with addition of 5% v/v DMSO as running buffer. Binders were diluted in the running buffer and injected for 3 min over the immobilized protein in a concentration series of 10-85 nM at a flow rate of 30 µL/min. An injection of 10 mM sodium acetate buffer at pH 4, effectively regenerated the protein sensor surface. Experiments were repeated at least three times.

The values of dissociation constants obtained by fitting the equations for a 1:1 interaction model to the experimental results are shown in Table 5. The highest affinity was found for 4-C15L8-6C-25OHVD$_3$ (i.e. a ligand-polypeptide conjugate wherein the polypeptide is 4-C15L8, the ligand is vitamin D3 hydroxylated on carbon 25 and is attached to the polypeptide via a 6-carbon spacer). The overall variation in the series is a factor of 40 showing clearly the effect of the polypeptide conjugation on affinity.

TABLE 5

Dissociation constants for binder molecules bound to immobilized vitamin D bindig protein determined by SPR biosensor analysis.

| Polypeptide | Reporter group | Ligand* | Spacer length | $K_d$ (nM) |
|---|---|---|---|---|
| 1-C15L8 | Dansyl | 25OHVD$_3$ | 8C | 290 |
| 2-C15L8 | Dansyl | 25OHVD$_3$ | 8C | 480 |
| 3-C15L8 | Dansyl | 25OHVD$_3$ | 6C | 1300 |
| 3-C15L8 | Dansyl | 25OHVD$_3$ | 8C | 1100 |
| 4-C15L8 | Dansyl | VD$_3$ | 6C | 1800 |
| 4-C15L8 | Coumarin | 25OHVD$_3$ | 6C | 50 |
| 4-C15L8 | Dansyl | 25OHVD$_3$ | 8C | 110 |
| 3-C10L17 | Dansyl | 25OHVD$_3$ | 8C | 1200 |
| 4-C10L17 | Dansyl | VD$_3$ | 6C | 890 |
| 4-C25L22 | Dansyl | VD$_3$ | 6C | 1300 |
| 4-C25L22 | Dansyl | 25OHVD$_3$ | 6C | 750 |
| 4-C37L34 | Dansyl | VD$_3$ | 6C | 900 |
| 4-C37L34 | Dansyl | 25OHVD$_3$ | 6C | 190 |

*VD$_3$ is Vitamin D3; 25OHVD$_3$ is a derivative of Vitamine D$_3$ having a hydroxyl group at carbon 25.

Example 6

In Example 6, the selected target molecule was the D-dimer protein and the ligand was the GPRP peptide.

The process of coagulation in human blood is a cascade of molecular events, including the enzymatic cleavage of fibrinogen to form fibrin which aggregates into proteofibrils that upon crosslinking at the D fragment site forms an insoluble gel and subsequently blood clots. (Furie, B., and Furie, B. C. (2005) Thrombus formation in vivo. J. Clin. Invest. 115, 3355-3362. Davie, E. W. (1964) Waterfall sequence for intrinsic blood clotting. Science 145, 1310-1312.) Enzymatic degradation of the clots release crosslinked D fragments, known as D-dimers, which are normally not present in blood unless coagulation has occurred and the D-dimer therefore serves as a biomarker for thrombosis. (Lippi, G., Cervellin, G., Franchini, M., and Favaloro, E. J. (2010) Biochemical markers for the diagnosis of venous thromboembolism: the past, present and future. *J. Throm. Thrombolysis* 30, 459-471. Wada, H., and Sakuragawa, N. (2008) Are fibrin-related markers useful for diagnosis of thrombosis? *Semin. Thromb. Hemost.* 34, 33-38.) The measurement of D-dimer concentration in blood is a recognized and common diagnostic test, it is commonly used to exclude the possibility of thromboembolic disease. (Linkins, L.-A., Bates, S. M., Ginsberg, J. S., and Kearon, C. (2004) Use of different D-dimer levels to exclude venous thromboembolism depending on clinical pretest probability. *J. Throm. Haemost.* 2, 1256-1260.)

Specific, high-affinity binders for the D-dimer protein are required for the measurement of D-dimer levels in bioanalytical applications, especially within the field of in vitro diagnostics. In diagnostic applications monoclonal antibodies are the golden standard and recognize specific epitopes on protein surfaces to which they bind with high affinity and selectivity. Recently, we reported on an alternative strategy for protein recognition and binding based on the conjugation of small organic molecules to 42-residue polypeptides, a technology shown to provide small and robust binder molecules that performance equal to or better than average antibodies. (Baltzer, L. (2011) *Crossing borders to bind proteins-a new concept in protein recognition based on the conjugation of small organic molecules or short peptides to polypeptides from a designed set. Anal. Bioanal. Chem.* 400, 1653-1664.) The organic molecules are required to have only modest affinities and selectivities for the protein and the polypeptides are selected from a set with only sixteen members designed to boost the affinity and selectivity for any protein. The small molecule ligands and the polypeptides were shown after conjugation to bind cooperatively to proteins such as the C-reactive protein (CRP) and human Carbonic Anhydrase II (HCAII). (Tegler, L. T., Nonglaton, G., Buttner, F., Caldwell, K., Christopeit, T., Danielson, U. H., Fromell, K., Gossas, T., Larsson, A., Longati, P., Norberg, T., Ramapanicker, R., Rydberg, J. and Baltzer, L. (2011) Powerful Protein Binders from Designed Polypeptides and Small Organic Molecules—A General Concept for Protein Recognition. Angew Chemie Int Ed. 50, 1823-1827. Enander, K., Dolphin, G., and Baltzer, L. (2004) Designed, functionalized helix-loop-helix motifs that bind Human Carbonic Anhydrase II: a new class of synthetic receptor molecules. J. Am. Chem. Soc. 126, 4464-4465. Tegler, L. T., Fromell, K., Jonsson, B.-H., Viljanen, J., Winander, C., Carlsson, J. and Baltzer, L. (2011) Polypeptide conjugate binders that discriminate between two isoforms of human Carbonic anhydrase in human blood. ChemBioChem. 12, 559-566. Andersson, T., Lundquist, M., Dolphin, G. T., Enander, K., Jonsson, B-H., Nilsson, J. W. and Baltzer, L. (2005) The binding of Human Carbonic Anhydrase II by functionalized folded polypeptide receptors. Chem. Biol. 12, 1245-1252.) Affinities of the binders were on the order of two to four orders of magnitude higher than those of the small molecules, although the polypeptides did not have any previous relationship to CRP or HCAII and did not bind strongly enough to be measured independently. The molecular weights of the polypeptide conjugates are in the range of 5-6 kD, and therefore approximately 1/30 of a IgY. They do not have ordered structures and adapt to the surface of the biological target. The concept is different from that of biologically generated binder molecules. While the use of small organic molecules as functional groups is an attractive strategy in the design of high-affinity binders for proteins because of their robustness and lack of recognition by natural enzymes, the pool of available peptides is essentially endless, considering the number of sequences that can be identified, for example, from phage display techniques. (Smith, G. P., and Petrenko, V. A. (1997) Phage display. *Chem. Rev.* 97, 391-410.) It is therefore of considerable interest to determine whether tight binders can also be obtained by conjugating short peptides instead of small organic molecules as this would expand the accessible pool of binder candidates dramatically.

The development of binders for the D-dimer is an attractive goal for a proof-of-concept demonstration of a peptide based polypeptide conjugate as it is a validated biomarker and because there is a short peptide, GPRP, that is well-characterized and known to bind the D-dimer with a Kd of 25 μM. (Laudano, A. P., and Doolittle, R. F. (1980) Studies on synthetic peptides that bind to fibrinogen and prevent fibrin polymerization. Structural requirements, number of binding sites, and species differences. Biochemistry 19, 1013-1019. Laudano, A. P., and Doolittle, R. F. (1981) Influence of calcium ion on the binding of fibrin amino terminal peptides to fibrinogen. Science 212, 457-459.) The GPRV sequence of the E domain of fibrinogen is involved in the aggregation of activated fibrinogen to form fibrin and subsequently higher aggregates, and known to bind specifically to a binding site on the D-domain. (Olexa, S. A., and Budzynski, A. Z. (1980) Evidence for four different polymerization sites involved in human fibrin formation. Proc. Natl. Acad. Sci. USA, 77, 1374-1378. Pratt, K. P., Cote, H. C. F., Chung, D. W., Stenkamp, R. E., and Davie, E. W. (1997) The primary fibrin polymerization pocket: three-dimensional structure of a 30-kDa C-terminal γ chain fragment complexed with the peptide GLy-Pro-Arg-Pro. Proc. Natl. Acad. Sci. USA. 94, 7176-7181.) The GPRP sequence was developed and found to bind with higher affinity than GPRV to the D-dimer. The structure of the complex between the D-dimer and GPRP has been solved and the N-terminal Gly residue has been shown to be involved in hydrogen bonding to amino acid residues in the GPRP binding crevice. (Spraggon, G., Everse, S. J., and Doolittle, R. F. (1997) Crystal structures of fragment D from human fibrinogen and its crosslinked counterpart from fibrin, Nature 389, 455-462. Everse, S. J., Spraggon, G., Veerapandian, L., Riley, M., and Doolittle, R. F. (1998) Crystal structure of fragment double-D from human Fibrin with two different bound ligands. Biochemistry 37, 8637-8642.)

In this Example, it is shown that the GPRP peptide, linked to polypeptides from the set of designed 42-residue sequences according to the present invention form powerful binders for the D-dimer (FIG. 31).

Results and Discussion
Design

The 16-membered set of polypeptides used was as shown in FIG. 1.

As noted herein above, an important aspect of binder development is the selection of spacer. The size of the spacer controls to what extent the protein surface is accessible to the polypeptide. Intuitively, one would expect that selectivity decreases with increased spacer length whereas affinity might increase. Experience suggests that alifatic spacers generate the highest affinities perhaps because of added hydrophobic contacts with the protein whereas polyethyleneglycol spacers show weaker binding. (Gao, J., Qiao, S., and Whitesides, G. M. (1995) Increacing binding constants of ligands to carbonic anhydrase by using "greasy tails". J. Med. Chem. 38, 2292-2301. Jain, A., Huang, S. G., and Whitesides, G. M. (1994) Lack of effect of the length of oligoglycine- and oligo(ethylene glycol)-derived para-substituents on the affinity of benzenesulfonamides for carbonic anhydrase II in solution. J. Am. Chem. Soc. 116, 5057-5062.) In the design of binders for the D-dimer a hexacarbon spacer was introduced for the attachment of GPRP to the polypeptides based on an analogy with the C-reactive protein.

The binding of GPRP to the D-dimer was analyzed from the crystal structure of the complex and most importantly the N-terminal Gly was found to be involved in binding. The spacer therefore had to be attached to the C-terminal Pro residue. In addition, to attach the spacered small molecule ligand to the peptide a Gly residue was incorporated at the carboxylic group of the spacer, mainly for ease of synthesis, as the most suitable resin for solid phase peptide synthesis of the short peptide was provided with a preloaded Gly.

Synthesis.

The synthesis of the polypeptides followed standard SPPS Fmoc protocols and has been reported in detail, previously. (Tegler, L. T., Nonglaton', G., et al. (2011), vide supra). They were purified by semi-preparative reversed-phase HPLC and identified by MALDI-TOF mass spectrometry. GPRP equipped with a caprylic acid spacer extended by a Gly residue transformed into a p-nitrophenyl ester was also synthesized on the solid phase and purified as well as identified as described below in the Experimental section. The conjugation reaction was carried out in DMSO in an essentially quantitative reaction and the final binder molecules were purified and identified as the peptides described above, see Experimental section.

Selection of Binders

The 16-membered set of binder candidates obtained by conjugation of each of the polypeptides to the spacered GPRP was evaluated in a Biacore assay where the D-dimer was immobilized on the chip and the binder molecules were allowed to flow over the chip at concentrations of 0, 1, 10 and 100 nM in standard running buffer. The preliminary results obtained demonstrated that the binders 4D15L8-GPRP, 4D10L17-GPRP, 4D25L22-GPRP bound strongly to the D-dimer. For sensorgrams and estimated dissociation constants describing the interactions between the D-dimer protein and 15 polypeptide conjugates, cf. Table 6 and FIG. 32. At 100 nM concentration the uptake was considerable and some uptake was also observed at 10 nM concentration whereas no binding was observed for the 1 nM solutions. In the interest of efficiency, the binder solutions were prepared from weighing the peptides and reported concentrations in error of 20-30% are possible. This does not affect conclusions about which binders are the tightest since the titration steps were large, but may give rise to incorrect ranking of the best binders. Seven binders were therefore selected for further binding analysis based on the largest uptake but also on Kd values obtained from the best fit of a 1:1 binding model to the experimental data. Whereas the fit of the 1:1 model is far from excellent and the obtained Kd's should be taken with considerable caution, the combined ranking from estimates of uptake from Biacore and the Kd "values" were in reasonable agreement. For estimated dissociation constants, cf. Table 6.

TABLE 6

Dissociation constants (Kd) for the D-dimer protein and binders by measured by SPR interaction analysis

| Binder | Kd (uM) | Binder | Kd (uM) |
|---|---|---|---|
| 1D15L8_GPRP | NA | 1D25L22_GPRP | NA |
| 2D15L8_GPRP | 10.4 | 2D25L22_GPRP | 16.1 |
| 3D15L8_GPRP | 0.161 | 3D25L22_GPRP | 1.89 |
| 4D15L8_GPRP | 0.477 | 4D25L22_GPRP | 0.778 |
| 1D10L17_GPRP | NA | 1D37L34_GPRP | 5.07 |
| 2D10L17_GPRP | 10.3 | 2D37L34_GPRP | 13.6 |
| 3D10L17_GPRP | 1.85 | 3D37L34_GPRP | 1.15 |
| 4D10L17_GPRP | 0.603 | 4D37L34_GPRP | ND |

Dissociation constants, Kd, were obtained by using the Biaevaluation program version 3.2 (Biacore) and assuming a simple 1:1 Langmuir binding mechanism.

Binders with an uptake of more than 100 RU in the Biacore screening experiment that also had apparent Kd's of less than 1 μM were considered medium to tight binders whereas those with an uptake of less than 100 RU and Kd's of higher than 1 μM were considered weak binders and not considered further.

The interactions between the D-dimer protein and the seven selected binders were studied at higher resolution, as binders at concentrations of 0 nM (pure buffer), 5 nM, 10 nM, 20 nM, 40 nM, 80 nM and 160 nM were used for SPR interaction analysis, FIG. 33A, and concentrations were determined by quantitative amino acid analysis. The sensorgrams show that the binders from the 4-series bind with higher affinity than those from the 3-series, suggesting that more positively charged polypeptides bind better to the surface area of the D-dimer in the vicinity of the binding site. In order to show that the binder molecule binds according to design competition experiments were carried out using Biacore where GPRP over a range of concentrations was included in the running buffer to inhibit binding to the D-dimer, FIG. 34. As a control GPRP binding was also monitored. Binding of 100 nM 4-D10L17-GPRP was completely inhibited by 1 mM GPRP in standard running buffer, and decreased as a function of GPRP concentration with a 50% inhibition observed at a GPRP concentration of approximately 50 µM corresponding to a 500-fold higher affinity of the binder in comparison to GPRP. The results show that the GPRP residue is critical for binding, that the binder molecule binds specifically to the GPRP binding site and that the polypeptide boosts the affinity of GPRP by nearly three orders of magnitude, all according to design. In order to determine a dissociation constant in solution unaffected by surface effects, a fluorescein fluorophore was conjugated to the Cys side chain of the binder 4-C15L8-GPRP. The corresponding binder molecule was carefully titrated with the D-dimer protein followed by data analysis where the best fit of an equation describing the dissociation of a 1:1 complex to the experimental results was determined, FIG. 35. The dissociation constant was found to be 3 nM, or four orders of magnitude larger than that of the solution affinity of the GPRP tetrapeptide. (Laudano, A. P., and Doolittle, R. F. (1980), vide supra)

In order to further boost the binding performance the binders of the 4-series were dimerized by reacting deprotected Cys residues in the loop region of the helix-loop-helix motifs with a bifunctional linker to form polyethyleneglycol linked helix-loop-helix dimers. The seven binders from the 3- and 4-series shown to be the strongest binders were dimerized and their binding to the D-dimer analyzed by Biacore, FIG. 33B. In comparison with the monomeric binder molecules increased binder performance was in general observed for all binders based on the observation of increased uptake. It is difficult from the Biacore data to determine quantitatively actual increases in affinity from decreased dissociation constants because of the poor fits of the 1:1 Langmuir model to the experimental data. However, the uptake was clearly increased and the dissociation constants obtained by fitting the 1:1 Langmuir model to the experimental data suggested relative affinity increases by factors of 2-4 as a result of dimerization, cf. Table 7.

TABLE 7

Dissociation constants, Kd, for D-dimer binding of binders from SPR interaction analysis

| Two-PEG linked Binder | Kd (nM) | Binder | Kd (nM) |
|---|---|---|---|
| 3D15L8_GPRP-PEG | 11.3 | 3D15L8-GPRP | 42.0 |
| 3D10L17_GPRP-PEG | 23.8 | 3D10L17-GPRP | 95.1 |
| 3D25L22_GPRP-PEG | 4290 | 3D25L22-GPRP | 36.4 |
| 3D37L34_GPRP-PEG | 32.4 | 3D37L34-GPRP | 15.4 |
| 4D15L8_GPRP-PEG | 12.6 | 4D15L8-GPRP | 5.79 |

TABLE 7-continued

Dissociation constants, Kd, for D-dimer binding of binders from SPR interaction analysis

| Two-PEG linked Binder | Kd (nM) | Binder | Kd (nM) |
|---|---|---|---|
| 4D10L17_GPRP-PEG | 2.17 | 4D10L17-GPRP | 6.56 |
| 4D25L22_GPRP-PEG | 3.41 | 4D25L22-GPRP [2] | 9.46 |

Dissociation constants, Kd, were obtained by using the Biaevaluation program version 3.2 (Biacore) and assuming a simple 1:1 Langmuir binding mechanism.

For the binder 4-C2522-GPRP a disulfide bridge gave better performance than the PEG spacer and a further affinity boost by a factor of two, and thus a total of nearly an order of magnitude. The simple chemical procedure of dimerising the binder molecules was thus shown to further increase affinities by a factor of 5-10, enabling the development of peptide based binder molecules with high pM affinities from low to medium µM affinity peptides that are readily available from early phase phage display generation of peptides. Attaching more well developed phage display peptides to the designed polypeptides is expected to give rise to proportionally higher affinity binder molecules.

The sensorgrams obtained from binding of the D-dimer are similar to those obtained from sensor analysis of other proteins in that they do not show saturation and application of stand- and kinetic models to the experimental results do not give good fits. In contrast, fluorescence titration experiments of binding as well as Rifs, reflectance interference spectroscopy (Albrecht, C., Fechner, P., Honcharenko, D., Baltzer, L., and Gauglitz, G. (2010) A new assay design for clinical diagnostics based on alternative recognition elements. *Biosens. Bioelectron.* 25, 2302-2308) show the expected behaviour and the reason for the poor fits obtained from Biacore measurements are not yet clear. The kinetic curves clearly do not show single exponential behaviour but very complex models are needed to elucidate the binding kinetics. Nevertheless, the data show strong uptake and tight binding of binders based on the GPRP peptide.

Experimental Section

All reagents and solvents were purchased from commercial sources and were used without further purification. Thin layer chromatography (TLC) was performed on 60 $F_{254}$ silica and 60 F254 aluminum oxide plates (Merck) and spots were visualized with UV light (λ=254 nm). $^1$H NMR spectra were recorded on Varian Inova 500 MHz (499.9 MHz) spectrometer and $^{13}$C NMR spectra were recorded on Varian Unity 400 MHz (100.6 MHz) spectrometer. Spectra were recorded at 25° C. using deuterated chloroform as solvent. Chemical shifts (δ) in ppm are reported using TMS as an internal reference (1H δ0.0) and residual chloroform signal (13C δ 77.0) and coupling constants (j) are reported in Hz. Low resolution mass spectra were recorded on Perkin Elmer SCIEX API 150EX spectrometer in the positive ion mode. The human D-dimer protein was obtained from Abcam Inc. UK.

Peptide Synthesis.

The peptides were synthesized on a Pioneer automated peptide synthesizer using standard fluorenylmethoxycarbonyl (Fmoc) protocols with O-(7-benzotriazole-1-yl)-1,1,3,3-tetramethyluronium hexafluorophosphate (HBTU, Iris Biotech GmbH) and diisopropylethylamine (DIPEA, Aldrich) as activating agents. The Fmoc protection groups were removed by 20% piperidine in dimethyl formamide (DMF). The synthesis was performed on a 0.1 mmole scale with a Fmoc-glycine-polyethyleneglycol-polystyrene (Fmoc-Gly-PEG-PS) or a Fmoc-PAL-PEG-PS (Applied biosystems) resin, and a fourfold excess of amino acid in each coupling. The side chains of the amino acids (Calbiochem-Novabiochem AG, Iris Biotech GmbH) were protected by the base-stable groups: tert-butyl ester (Asp, Glu), trityl (His, Asn, Gln), tert-butoxymethyl (Lys) and 2,2,4,6,7-pentamethyldihydrobenzofuran-5-sulfonyl (Arg). Orthogonal protection of the lysine residues 15, 10, 25 and 34 by an allyloxycarbonyl (Alloc) group in the sequences C15L8, C10L17, C25L22 and C37L34, respectively, enabled the site specific introduction of a fluorescent probe in each polypeptide. Deprotection of the allyloxcarbonyl group was performed by treatment of the resin with tetrakis(triphenylphosphine)palladium(0) (Pd $(Ph_3)_4$) in trichloromethane, acetic acid and N-methylmorpholine (ratio 37:2:1 v/v; 10 mL per gram of resin) at room temperature, under $N_2$ during 2 h. The resin was washed sequentially with 0.5% DIPEA in DMF and 0.5 diethyldithiocarbamic acid in DMF, DMF and DCM and desiccated.

Coupling of 7-methoxycoumarin-3-carboxylic acid to the amino group of the lysine side chain was performed in DMF during 2 hours with gentle stirring at room temperature with two-fold excess of acid activated by a coupling cocktail consisting of N—N-Diisopropylethylamine (DIPEA), 1-Hydroxy benzotriazole (HOBt), Diisopropyl carbodiimide (DIC) in the ratio 12:6:6. After two hours, an additional aliquot of coupling cocktail was added and the reaction was left over night. For each peptide, deprotection and cleavage from the resin was achieved by treatment with a mixture of trifluoroacetic acid (TFA), water and triisopropylsilane (95:2.5:2.5 v/v, 10 mL per gram of polymer) for 2 hours at room temperature. After filtration and concentration the peptide was precipitated by addition of cold diethyl ether, centrifuged, washed in diethyl ether and dried in air. The crude peptides were purified by reversed-phase HPLC on a semi-preparative Hypersil C-18 Gold column pore size 175 Å, particle size 5A, or a semi-preparative Kromasil C8 Hichrom column pore size 100 Å, particle size 10 Å, eluted with a shallow 35-55% acetonitrilee gradient in water and 0.1% TFA as additive at a flow rate of 10 mL/min. Collected fractions were identified by MALDI-TOF mass spectrometry (Bruker Daltonics Ultraflex II TOF/TOF), concentrated and lyophilised twice.

Synthesis of the GPRP Ligand with a Spacer (FIG. 36)

Preparation of the Hexapeptide Ligand

A 6 carbon spacer for the GPRP ligand was synthesized by attaching a 6-aminocaproic acid residue to the proline residue at the C-terminus. The synthesis of the peptide was done in 0.5 mmol scale using manual SPPS (Fmoc/$^t$Bu strategy using PyBOP for activation, 2 fold excess of amino acids and the coupling reagent was used), on a chlorotrityl resin preloaded with glycine (0.75 mmol/g). The arginine side chain and the N-terminus glycine were protected as Pbf and Boc groups respectively. The hexapeptide obtained from SPPS was cleaved from the resin by treating with 1.5% TFA in $CH_2Cl_2$ (10 mL) for 5 minutes. The resin was washed with 1% TFA in $CH_2Cl_2$ (2×5 mL) to ensure complete cleavage of the peptide. The peptide solution was washed with saturated citric acid to remove any free amines (formed by the deprotection of Pbf or Boc group) present in the solution and was dried over $MgSO_4$ and concentrated. The crude residue was directly used for the preparation of the active ester.

Preparation of the Active Ester for Conjugation

The crude hexapeptide was dissolved in anhydrous $CH_3CN$ (10 mL) and was stirred at 0° C. Pyridine (2 mL), DIC (0.3 mL, 4 equiv) and p-nitrophenol (0.28 g, 4 equiv) was added to the peptide solution and the stirring was continued for 15 h (overnight). The reaction mixture was concentrated under vacuum, the residue was dissolved in $CH_2Cl_2$ (50 mL) and was washed with saturated citric acid (2×50 mL). The $CH_2Cl_2$ solution of the active ester was dried over $MgSO_4$ and the solution volume was reduced to 10 mL by evaporation. The crude product was purified by silica gel (60-90 mesh) column chromatography by eluting with 0 to 100% acetone in $CH_2Cl_2$. The active ester of the peptide was obtained as a white solid (150 mg, 30% overall yield).

Biacore Measurements.
Immobilization.

Before immobilization, the storage buffer for the D-dimer protein was changed to 10 mM NaOAc at pH 4.6 with NAP5 (GE Healthcare Bio-Sciences, Uppsala, Sweden). The protein was then further diluted with 10 mM NaOAc at pH 4.6 to give a concentration of about 32 µg/mL. The D-dimer protein was covalently immobilized on the sensor chip surface by amine coupling with HBS-EP (10 mM HEPES, pH 7.4, 150 mM NaCl, 3 mM EDTA and 0.005% P20) (GE Healthcare Bio-Sciences, Uppsala, Sweden) as a running buffer. The CM5 sensor chip surface was activated for 7 min by injecting a solution of EDC/NHS (200 mM 1-ethyl-3-(3-dimethylaminopropyl)-carbodiimide hydrochloride/50 mM N-hydroxysuccinimide) (GE Healthcare Bio-Sciences, Uppsala, Sweden). The D-dimer protein was injected for 1.5 min at flow rate of 5 uL/min over the activated surface and followed by 7-min pulse of 1M ethanolamine at pH 8.5 to deactivate remaining active ester. The final immobilization levels were between 6000 and 7500 resonance units (RU).

Interaction Analysis.

The interactions between the D-dimer protein and binders as well as surface competition experiments were studied using a Biacore 2000 instrument (GE Healthcare Bio-Sciences, Uppsala, Sweden), equilibrated at 25° C. The CM5 sensor chip (Research grade, Biacore) and reagents were from GE Healthcare Bio-Sciences, Uppsala, Sweden. For direct interaction studies between immobilized D-dimer protein and polypeptide conjugates, HBS-EP was used as running buffer. The polypeptide conjugates were diluted in the running buffer and injected over the immobilized protein in concentration series of 5-160 nM, or 1-100 nM, for initial screening, using 3 min contact time. For minimum sample dispersion, the samples were injected at a flow rate of 50 uL/min. After 10 min of dissociation the surface was regenerated by 30 s pulse injection of 10 mM glycine at pH 3.0. All injections were serial and first passed over the deactivated dextran surface and then over the immobilized surfaces. Blank injections were included for each measurement series and subtracted from the data. Experiments were performed at least twice, unless stated otherwise. In the surface competition assay, a series of mixtures of the binder 4-D10L17-GPRP (100 nM) and a number of concentrations of GPRP in the range 0-1 mM was injected over the immobilized D-dimer protein. The dissociation constants, Kd, were obtained using the Biaevaluation program version 3.2 (Biacore) and assuming a simple 1:1 Langmuir binding mechanism.

Coupling of Fluorescein to 4-D15L8-GPRP 1.27 mg (22.0 µmol) 4-D15L8-GPRP, containing a free cysteine in the loop region, was dissolved in 210 µL $N_2$(g) bubbled 6M GuHCl in 0.1 M NaPi, pH 7.3 (1 mM), and incubated with 4 molar equivalents (0.38 mg) of Fluorescein-5-maleimide (Pierce Biotechnology), pre-dissolved in 10 µL DMSO, for 4 h at r.t. The reaction was followed by analytical reversed phase HPLC using a GraceVydac, MS $C_{18}$ column (4.6×150 mm) with a shallow gradient of ACN:$H_2O$ from 30 to 55% ACN. The identity of the product was confirmed with MALDI-MS (Voyager PRO, Applied Biosystems) using a mixture of α-cyano-4-hydroxycinnamic acid and 2-(4-hydroxy-phenylazo)-benzoic acid as matrix with detection in the positive mode. After completion of the reaction the fluorescein-peptide conjugate was purified by reversed phase HPLC and the pooled fractions was evaporated and lyophilized.

Affinity Determination with Fluorescence Spectroscopy

Fluorescence spectra were recorded on a Fluoromax Gemini XPS microplate reader at 25° C. The excitation wavelength was 495 nM and the emission was monitored in the range 510-600 nM. Prior to the experimental setup, all plastics (tubes, tips and the microplate) were coated with 1% aqueous solution of Pluronic® F108NF Prill Polaxamer 338 (BASF) for 12 h, followed by thorough wash with water in order to minimize unspecific surface interactions. For the affinity determination, samples of 100 nM fluorescein-labeled 4-D15L8-GPRP in N$_2$(g) bubbled phosphate buffered saline (50 mM NaH$_2$PO$_4$, 150 mM NaCl, pH 7.5) were set up in a 384-well black microplate (Nunc). Aliquots from solutions of D-dimer (Abcam Inc. UK, 3.0 µM, 0.6 µM, 0.1 µM and 10 nM) was then added to the wells in the range 1.0 nM to 1.5 µM. The 0.6 µM to 10 nM solutions were diluted from the 3.0 µM stock solution with phosphate buffered saline. The total volume in all wells was 100 µL and was compensated by the buffer volume. The fluorescence intensity at 525 nm was monitored as a function of total protein concentration and the dissociation constant $K_d$ was determined by fitting the following equation to the experimental results under the assumption of a 1:1 binding model:

$$F_{obs} = \frac{F_{bound} \cdot [Ddim] + F_{free} \cdot K_d}{[Ddim] + K_d}$$

$F_{obs}$ is the observed fluorescence intensity, $F_{bound}$ is the fluorescence of the peptide bound to D-dimer, $F_{free}$ is the fluorescence of free peptide, and [Ddim] is the concentration of free D-dimer. [Ddim] can be derived from $$[Ddim] = -\frac{[P]_{tot} + K_d - [Ddim]_{tot}}{2} + \sqrt{\left(\frac{[P]_{tot} + K_d - [Ddim]_{tot}}{2}\right)^2 + K_d \cdot [Ddim]_{tot}}$$

where $[P]_{tot}$ is the total concentration of peptide and $[Ddim]_{tot}$ is the total concentration of D-dimer. Fitting was done with the IGOR Pro 6.0 software (WaveMetrics Inc.).

---

The invention claimed is:

1. A molecular tool for use in a method of providing a molecule that is capable of binding a target molecule, said tool comprising a plurality of polypeptides according to any one or several of SEQ ID NOs 1-32, each polypeptide having a ligand capable of binding a target molecule, attached by an amide bond to an amino acid in a position selected from positions 8, 17, 22, and 34 of the polypeptide sequence, and a reporter group for detecting binding to a target molecule, attached by an amide bond to an amino acid in a position selected from positions 15, 10, 25 and 37 of the polypeptide sequence.

2. A molecular tool according to claim 1, wherein the polypeptides are according to at least 2 different SEQ ID NOs selected from SEQ ID NOs 1-32.

3. A molecular tool according to claim 1, wherein the ligand of each polypeptide is attached to an amino acid 8, 17, 22, or 34 independently selected from lysine, ornithine and 2,4-diaminobutyric acid and the reporter group of each polypeptide is attached to an amino acid in position 15, 10, 25 or 37 independently selected from lysine, ornithine and 2,4-diaminobutyric acid.

4. A method of screening for a ligand-polypeptide conjugate capable of binding a target molecule, comprising
providing at least one conjugate molecule comprising a polypeptide having a sequence selected from SEQ ID NOs 1-32, said polypeptide having a ligand for the target molecule attached by an amide bond to an amino acid capable of forming an amide bond with the ligand, said amino acid being at a position in the polypeptide sequence selected from positions 8, 17, 22, and 34, and said polypeptide having a reporter group attached by an amide bond to an amino acid capable of forming an amide bond with the reporter group, said amino acid being at a position in the polypeptide sequence selected from positions 15, 10, 25 and 37;
bringing the target molecule in contact with the conjugate molecule; and
detecting a signal from the reporter group.

5. A method according to claim 4, comprising providing a set of from 2 to 16 conjugate molecules having differing polypeptide sequences selected from SEQ ID NOs 1-32.

6. An isolated polypeptide having a sequence selected from SEQ ID NOs 1-32.

7. An isolated polypeptide according to claim 6, wherein a ligand capable of binding a target molecule is attached by an amide bond to an amino acid capable of forming an amide bond with the ligand, said amino acid being in a position selected from positions 8, 17, 22, and 34 of the polypeptide sequence.

8. An isolated polypeptide according to claim 7, wherein the target molecule is a protein or polypeptide.

9. An isolated polypeptide according to claim 6, wherein a reporter group for detecting binding to a target molecule is attached by an amide bond to an amino acid capable of forming an amide bond with the reporter group, said amino acid being in a position selected from positions 15, 10, 25 and 37 of the polypeptide sequence.

10. An isolated polypeptide that is a dimer of two polypeptides independently selected from the isolated polypeptides according to claim 6.

11. A plurality of isolated polypeptides comprising at least two different isolated polypeptides according to claim 6.

12. A plurality of isolated polypeptides according to claim 11, comprising isolated polypeptides having different SEQ ID NOs selected from SEQ ID NOs 1-32.

13. A molecular tool according to claim 2, wherein the ligand of each polypeptide is attached to an amino acid 8, 17, 22, or 34 independently selected from lysine, ornithine and 2,4-diaminobutyric acid and the reporter group of each polypeptide is attached to an amino acid in position 15, 10, 25 or 37 independently selected from lysine, ornithine and 2,4-diaminobutyric acid.

* * * * *